United States Patent
Shabb et al.

(10) Patent No.: US 9,470,693 B2
(45) Date of Patent: Oct. 18, 2016

(54) METHOD FOR QUANTIFYING PROTEINS AND ISOFORMS THEREOF

(71) Applicant: University of North Dakota, Grand Forks, ND (US)

(72) Inventors: John B. Shabb, Grand Forks, ND (US); Aaron Mehus, Hatton, ND (US); Wallace Muhonen, Grand Forks, ND (US); Donald A. Sens, Grand Forks, ND (US); Scott Garrett, Grand Forks, ND (US)

(73) Assignee: University of North Dakota, Grand Forks, ND (US)

( * ) Notice: Subject to any disclaimer, the term of this patent is extended or adjusted under 35 U.S.C. 154(b) by 0 days.

(21) Appl. No.: 14/401,770

(22) PCT Filed: May 17, 2013

(86) PCT No.: PCT/US2013/041651
§ 371 (c)(1),
(2) Date: Nov. 17, 2014

(87) PCT Pub. No.: WO2013/173756
PCT Pub. Date: Nov. 21, 2013

(65) Prior Publication Data
US 2015/0126402 A1   May 7, 2015

Related U.S. Application Data

(60) Provisional application No. 61/649,118, filed on May 18, 2012.

(51) Int. Cl.
*G01N 33/68* (2006.01)
*G01N 33/58* (2006.01)

(52) U.S. Cl.
CPC .......... *G01N 33/6848* (2013.01); *G01N 33/58* (2013.01); *G01N 2333/825* (2013.01); *G01N 2458/15* (2013.01); *G01N 2560/00* (2013.01); *G01N 2800/709* (2013.01); *G01N 2800/7028* (2013.01)

(58) Field of Classification Search
None
See application file for complete search history.

(56) References Cited

U.S. PATENT DOCUMENTS

2002/0147138 A1   10/2002   Firestone et al.
2010/0240665 A1    9/2010   Eckhardt et al.

FOREIGN PATENT DOCUMENTS

| NO | WO-98/13059 A1 | 4/1998 |
|----|----------------|--------|
| WO | WO-03016861 A2 | 2/2003 |
| WO | WO-2009/108215 A1 | 9/2009 |
| WO | WO-2013173756 A1 | 11/2013 |
| WO | WO-2013173756 A8 | 11/2013 |

OTHER PUBLICATIONS

Sechi et al. Anal. Chem. 1998, 70, 5150-5158.*
"International Application Serial No. PCT/US2013/041651, International Preliminary Report on Patentability mailed Nov. 27, 2014", 9 pgs.
Arriaga, Juan M., et al:, "Metallothionein expression in colorectal cancer: relevance of different isoforms for tumor progression and patient surival", *Human Pathology*, 43, (2012), 197-208.
Bylander, John E. et al., "Exposure of human proximal tubule cells to cytotoxic levels of $CdCl_2$ induces the additional expression of metallothionein 1A mRNA", *Toxicology Letters*, 76(3), (1995), 209-217.
Bylander, John E., et al., "Induction of metallothionein mRNA and protein following exposure of cultured human proximal tubule cells to cadmium", *Toxicology Letters*, 71(2), (1994), 111-122.
Datta, Jharna, et al., "Metallothionein Expression is Suppressed in Primary Human Hepatocellular Carcinomas and is Mediated through Inactivation of CCAAT/Enhancer Binding Protein α by Phosphatidylinositol 3-Kinase Signalling Cascade", *Cancer Research*, 67(6), (2007), 2736-2746.
Desiere, Frank, et al., "Integration with the human genome of peptide sequences obtained by high-throughput mass spectrometry", *Genome Biol.*, 6(1): R9, (2004), 12 pgs.
Desiere, Frank, et al., "The PeptideAtlas project", *Nucl Acids Res.* 34, (2006), D655-D658.
Friedline, John A., et al., "Differntial Expression of the MT-1E Gene in Estogen-Receptor-Positive and -Negative Human Breast Cancer Cell Lines", *Am J Pathol*, 152(1), (1998), 23-27.
Garrett, Scott H., "Exposure of Human Proximal Tubule Cells to $Cd^{2+}$, $ZN^{2+}$, and $Cu^{2+}$ Induces Metallothionein Protein Accumulation but not Metallothionein Isoform 2 mRNA", *Environ Health Perspect*, 106, (1998), 587-595.
Garrett, Scott H., et al., "Metallothionein Isoform 1 and 2 Gene Expression in the Human Prostate: Downregulation of MT-1X in Advanced Prostate Cancer", *Prostate*, 43(2), (2000), 125-135.
Ghesquiere, Bart, et al., "Redox Proteomics of Protein-bound Methionine Oxidation", *Molec Cell Proteomics*, 10, (2011), 1-12.
Gurel, Volkan, et al., "Post-Transcriptional Regulation of Metallothionein Isoform 1 and 2 Expression in the Human Breast and the MCF-10A Cell Line", *Toxicol. Sci*, 85, (2005), 906-915.
Hoey, John G., et al., "Expression of MT-3 mRNA in human kidney, proximal tubule cell cultures, and renal cell carcinoma", *Toxicology Letters*, 92(2), (1997), 149-160.
Jin Rongxian, et al., "Metallothionein 1F mRNA Expression Correlates with Histological Grade in Breast Carcinoma", *Breast Cancer Re Treatment*, 66(3), (2001), 265-272.
Jin, Rongxian, et al., "Metallothionein 2A expression is associated with cell proliferation in breast cancer", *Carcinogenesis*, 23(1), (2002), 31-86.

(Continued)

*Primary Examiner* — Jacob Cheu
(74) *Attorney, Agent, or Firm* — Schwegman Lundberg & Woessner, P.A.

(57) ABSTRACT

A method for quantifying metallothionein protein isomers is described herein. Such metallothionein isomer protein quantification is useful for detecting and monitoring disease. As illustrated herein, protein quantification is a more accurate measure of metallothionein induction than is mRNA quantification.

15 Claims, 46 Drawing Sheets

(56) References Cited

OTHER PUBLICATIONS

Kissling, Margrit M., et al., "Primary structure of human hepatic metallothionein", *FEBS Lett*, 82(2), (1977), 247-250.
Kojima, Yutaka, et al., "Amino-acid sequence of equine renal metallothionein-1B", *Proc. Natl. Acad. Sci. USA*, 73(10), (1976), 3413-3417.
Landon, Michael, "Cleavage at Aspartyl-Prolyl Bonds", *Meth Enzymol, 47—Enzyme Structure*, (1977), 145-149.
Ryan, Michael J., et al., "HK-2: an immortalized proximal tubule epithelial cell line from normal adult human kidney", *Kidney Int*, 45(1), (1994), 48-57.
Sens, Mary Ann, et al., "Metallothion Isoform 3 Overexpression is Associated with Breast Cancers Having a Poor Prognosis", *Am J. Pathol.*, 159(1), (2001), 21-26.
Sens, Mary Ann, et al., "Metallothionein Isoform 3 as a Potential Biomarker for Human Bladder Cancer", *Environmental Health Perspectives*, 108(5), (2000), 413-418.
Somji, S., et al., "Metallothionein isoform 1 and 2 gene expression in the human bladder: evidence for upregulation of MT-1X mRNA in bladder cancer", *Cancer Detect Prev.*, 25(1), (2001), 62-75.
Tai, S. K., et al., "Differential Expression of Metallothionein 1 and 2 Isoforms in Breast Cancer Lines with Different Invasive Potential: Identification of a novel nonsilent metallothionein-1H mutant variant", *Am J. Pathol.*, 163(5), (2005), 2009-2019.
Tan, Own J.-K., et al., "Differential expression of metallothionein isoforms in nasopharyngeal cancer and inhibition of cell growth by antisense down-regulation of metallothionein-2A", *Oncology Reports*, 13, (2005), 127-131.
"International Application Serial No. PCT/US2013/041651, International Search Report mailed Aug. 21, 2013", 5 pgs.
"International Application Serial No. PCT/US2013/041651, Written Opinion mailed Aug. 21, 2013", 7 pgs.
Cherian, M. G., et al., "Metallothioneins in human tumors and potential roles in carcinogenesis", Mutation Research, 533, (2003), 201-209.
Hustoft, Hanne Kolsrud, "A Critical Review of Trypsin Digestion for LC-MS Based Proteomics", Integrative Proteomics, (Feb. 24, 2012).
Lai, Y., et al., "Targeting Metallothionein for Prognosis and Treatment of Breast Cancer", Recent Patents on Anti-Cancer Drug Discovery, 6, (2011), 178-185.
Mounicou, S, et al., "Identification of Metallothionein Subisoforms in HPLC Using Accurate Mass and Online Sequencing by Electrospray Hybrid Linear Ion Trap-Orbital Ion Trap Mass Spectrometry", Analytical Chemistry, vol. 82, No. 16, (Aug. 15, 2010), 6947-6957.
Nakamura, et al., "Mass spectrometry-based quantitative proteomics", Biotechnology and Genetic Engineering Reviews, vol. 24, No. 1, (Jan. 1, 2007), 147-164.
Pedersen, M. O., et al., "The roleofmetallothioneininoncogenesisandcancerprognosis", Progress in Histochemistry and Cytochemistry, 44, (2009), 29-64.
Sanz-Nebot, V, et al., "Characterization of metallothionein isoforms from rabbit liver by liquid chromatography coupled to electrospray mass spectrometry", Journal of Chromatography B: Biomedical Sciences & Applications, vol. 796, No. 2, (Nov. 5, 2003), 379-393.
Vaudel, Marc, et al., "Peptide and protein quantification: A map of the minefield", Proteomics, vol. 10, No. 4, (Feb. 1, 2010), 650-670.
Wang, Rongying, et al., "Simple Method for Identification of Metallothionein Isoforms in Cultured Human Prostate Cells by MALDI-TOF/TOF Mass Spectrometry", Analytical Chemistry, vol. 79, No. 12, (Jun. 1, 2007), 4433-4441.
Wanic, et al., "Metallothioneins and metallothionein-like proteins as biomarkers of environmental contamination: Techniques for extraction, separation and quantification—a review", Brazilian Journal of Analytical Chemistry, vol. 1, No. 4, (Jan. 1, 2011), 206-221.

\* cited by examiner

| | | | |
|---|---|---|---|
| P04731 | MT-1A | AC-MDPN-CSCAT-GGSCTCTGSCKCKECKCTSCKKSCCSCCPMSCAKCAQGCICKGAS------EKCSCCA | 2 |
| Q93083 | MT-1L | AC-MDPN-CSCAT-GGSCSCASSCKCKCKCTSCKKSCCSCCPMGCAKCAQGCVCKGAS------EKCSCCA | 2 |
| P04732 | MT-1E | AC-MDPN-CSCAT-GGSCTCAGSCKCKECKCTSCKKSCCSCCPVGCAKCAQGCVCKGAS------EKCSCCA | 2 |
| P13640-1 | MT-1G | AC-MDPN-CSCAAAGVSCTCASSCKCKECKCTSCKKSCCSCCPVGCAKCAQGCICKGAS------EKCSCCA | 1 |
| P13640-2 | MT-1G | AC-MDPN-CSCAA-GVSCTCASSCKCKECKCTSCKKSCCSCCPVGCAKCAQGCICKGAS------EKCSCCA | 1 |
| P04733 | MT-1F | AC-MDPN-CSCAA-GVSCTCAGSCKCKECKCTSCKKSCCSCCPVGCSKCAQGCVCKGAS------EKCSCCD | 2 |
| P02795 | MT-2 | AC-MDPN-CSCAA-GDSCTCAGSCKCKECKCTSCKKSCCSCCPVGCAKCAQGCICKGAS------DKCSCCA | 2 |
| P80294 | MT-1H | AC-MDPN-CSCEA-GGSCACAGSCKCKKCKCTSCKKSCCSCCPLGCAKCAQGCICKGAS------EKCSCCA | 2 |
| P80297 | MT-1X | AC-MDPN-CSCSP-VGSCACAGSCKCKECKCTSCKKSCCSCCPVGCAKCAQGCICKGTS------DKCSCCA | 2 |
| P07438 | MT-1B | AC-MDPN-CSCTT-GGSCACAGSCKCKECKCTSCKKCCCSCCPVGCAKCAQGCVCKGSS------EKCRCCA | 3 |
| Q8N339 | MT-1M | AC-MDPN-CSCTT-GVSCACTGSCTCKECKCTSCKKSCCSCCPVGCAKCAHGCVCKGTL------ENCSCCA | 3 |
| | | **  *  .  **:*:.**.*:*.*******.***.:.:.:***. ::;* ** | |
| P25713 | MT-3 | AC-MDPETCPCPSG-GSCTCADSCKCEGCKCTSCKKSCCSCCPAECEKCAKDCVCKGGEAAEAEAEKCSCCQ | 3 |
| P47944 | MT-4 | AC-MDPRECVCMSG-GICMCGDNCKCTTCNCKTYWKSCCPCCPPGCAKCARGCICKGGS------DKCSCCP | 2 |

Fig. 1D

| B | B Ions | B+2H | B NH3 | B H2O | AA | Y Ions | Y+2H | Y NH3 | Y H2O | Y |
|---|---|---|---|---|---|---|---|---|---|---|
| 1 | 174.1 | | | | M+42 | 2,225.7 | | 2,208.6 | 2,207.7 | 20 |
| 2 | 289.1 | | | 271.1 | D | 2,052.6 | | 2,035.6 | 2,034.6 | 19 |
| 3 | 386.1 | | | 368.1 | P | 1,937.6 | | 1,920.6 | 1,919.6 | 18 |
| 4 | 500.2 | | 483.2 | 482.2 | W | 1,840.5 | | 1,823.5 | 1,822.5 | 17 |
| 5 | 661.2 | | 644.2 | 643.2 | C+58 | 1,726.5 | | 1,709.5 | 1,708.5 | 16 |
| 6 | 748.2 | | 731.2 | 730.2 | S | 1,565.5 | | 1,548.5 | 1,547.5 | 15 |
| 7 | 909.2 | | 892.2 | 891.2 | C+58 | 1,478.5 | | 1,461.4 | 1,460.4 | 14 |
| 8 | 1,038.3 | | 1,021.3 | 1,020.3 | F | 1,317.4 | | 1,300.4 | 1,299.4 | 13 |
| 9 | 1,109.3 | | 1,092.3 | 1,091.3 | A | 1,188.4 | | 1,171.4 | 1,170.4 | 12 |
| 10 | 1,166.3 | | 1,149.3 | 1,148.3 | G | 1,117.4 | | 1,100.3 | 1,099.3 | 11 |
| 11 | 1,223.4 | | 1,206.3 | 1,205.4 | G | 1,060.3 | | 1,043.3 | 1,042.3 | 10 |
| 12 | 1,310.4 | | 1,293.4 | 1,292.4 | S | 1,003.3 | | 986.3 | 985.3 | 9 |
| 13 | 1,471.4 | | 1,454.4 | 1,453.4 | C+58 | 916.3 | | 899.3 | 898.3 | 8 |
| 14 | 1,542.4 | | 1,525.4 | 1,524.4 | A | 755.3 | | 738.2 | 737.3 | 7 |
| 15 | 1,703.5 | | 1,686.4 | 1,685.5 | C+58 | 684.2 | | 667.2 | 666.2 | 6 |
| 16 | 1,774.5 | | 1,757.5 | 1,756.5 | A | 523.2 | | 506.2 | 505.2 | 5 |
| 17 | 1,831.5 | | 1,814.5 | 1,813.5 | G | 452.2 | | 435.2 | 434.2 | 4 |
| 18 | 1,918.6 | | 1,901.5 | 1,900.5 | S | 395.2 | | 378.1 | 377.1 | 3 |
| 19 | 2,079.6 | | 2,062.5 | 2,061.6 | C+58 | 308.1 | | 291.1 | | 2 |
| 20 | 2,225.7 | | 2,208.6 | 2,207.7 | K | 147.1 | | 130.1 | | 1 |

Fig. 6B

| B | B Ions | B+2H | B-NH3 | B+20 | AA | Y Ions | Y+2H | Y-NH3 | Y-H2O | Y |
|---|---|---|---|---|---|---|---|---|---|---|
| 1 | 174.1 | | | | M+42 | 2,227.7 | | 2,210.7 | 2,209.7 | 20 |
| 2 | 289.1 | | | 271.1 | D | 2,054.6 | | 2,037.6 | 2,036.6 | 19 |
| 3 | 386.1 | | | 368.1 | P | 1,939.6 | | 1,922.6 | 1,921.6 | 18 |
| 4 | 500.2 | | 483.2 | 482.2 | N | 1,842.6 | | 1,825.5 | 1,824.5 | 17 |
| 5 | 661.2 | | 644.2 | 643.2 | C+58 | 1,728.5 | | 1,711.5 | 1,710.5 | 16 |
| 6 | 748.2 | | 731.2 | 730.2 | S | 1,567.5 | | 1,550.5 | 1,549.5 | 15 |
| 7 | 909.2 | | 892.2 | 891.2 | C+58 | 1,480.5 | | 1,463.4 | 1,462.5 | 14 |
| 8 | 1,010.3 | | 993.3 | 992.3 | T | 1,319.5 | | 1,302.4 | 1,301.4 | 13 |
| 9 | 1,111.3 | | 1,094.3 | 1,093.3 | T | 1,218.4 | | 1,201.4 | 1,200.4 | 12 |
| 10 | 1,168.4 | | 1,151.3 | 1,150.3 | G | 1,117.4 | | 1,100.3 | 1,099.3 | 11 |
| 11 | 1,225.4 | | 1,208.4 | 1,207.4 | G | 1,060.3 | | 1,043.3 | 1,042.3 | 10 |
| 12 | 1,312.4 | | 1,295.4 | 1,294.4 | S | 1,003.3 | | 986.3 | 985.3 | 9 |
| 13 | 1,473.4 | | 1,456.4 | 1,455.4 | C+58 | 916.3 | | 899.3 | 898.3 | 8 |
| 14 | 1,544.5 | | 1,527.4 | 1,526.5 | A | 755.3 | | 738.2 | 737.3 | 7 |
| 15 | 1,705.5 | | 1,688.5 | 1,687.5 | C+58 | 684.2 | | 667.2 | 666.2 | 6 |
| 16 | 1,776.5 | | 1,759.5 | 1,758.5 | A | 523.2 | | 506.2 | 505.2 | 5 |
| 17 | 1,833.5 | | 1,816.5 | 1,815.5 | G | 452.2 | | 435.2 | 434.2 | 4 |
| 18 | 1,920.6 | | 1,903.5 | 1,902.6 | S | 395.2 | | 378.1 | 377.1 | 3 |
| 19 | 2,081.6 | | 2,064.6 | 2,063.6 | C+58 | 308.1 | | 291.1 | | 2 |
| 20 | 2,227.7 | | 2,210.7 | 2,209.7 | K | 147.1 | | 130.1 | | 1 |

*Fig. 7B*

| B | B Ions | B+2H | B-NH3 | B-H2O | AA | Y Ions | Y+2H | Y-NH3 | Y-H2O | Y |
|---|---|---|---|---|---|---|---|---|---|---|
| 1 | 174.1 | | | | M+42 | 2,299.7 | | 2,282.7 | 2,281.7 | 20 |
| 2 | 289.1 | | | 271.1 | D | 2,126.7 | | 2,109.7 | 2,108.7 | 19 |
| 3 | 386.1 | | | 368.1 | P | 2,011.7 | | 1,994.6 | 1,993.7 | 18 |
| 4 | 500.2 | | 483.2 | 482.2 | N | 1,914.6 | | 1,897.6 | 1,896.6 | 17 |
| 5 | 661.2 | | 644.2 | 643.2 | C+58 | 1,800.6 | | 1,783.5 | 1,782.6 | 16 |
| 6 | 748.2 | | 731.2 | 730.2 | S | 1,639.6 | | 1,622.5 | 1,621.5 | 15 |
| 7 | 909.2 | | 892.2 | 891.2 | C+58 | 1,552.5 | | 1,535.5 | 1,534.5 | 14 |
| 8 | 1,010.3 | | 993.3 | 992.3 | T | 1,391.5 | | 1,374.5 | 1,373.5 | 13 |
| 9 | 1,111.3 | | 1,094.3 | 1,093.3 | T | 1,290.5 | | 1,273.4 | 1,272.5 | 12 |
| 10 | 1,168.4 | | 1,151.3 | 1,150.3 | G | 1,189.4 | | 1,172.4 | 1,171.4 | 11 |
| 11 | 1,267.4 | | 1,250.4 | 1,249.4 | V | 1,132.4 | | 1,115.4 | 1,114.4 | 10 |
| 12 | 1,354.5 | | 1,337.4 | 1,336.4 | S | 1,033.3 | | 1,016.3 | 1,015.3 | 9 |
| 13 | 1,515.5 | | 1,498.4 | 1,497.5 | C+58 | 946.3 | | 929.3 | 928.3 | 8 |
| 14 | 1,586.5 | | 1,569.5 | 1,568.5 | A | 785.3 | | 768.3 | 767.3 | 7 |
| 15 | 1,747.5 | | 1,730.5 | 1,729.5 | C+58 | 714.2 | | 697.2 | 696.2 | 6 |
| 16 | 1,848.6 | | 1,831.5 | 1,830.6 | T | 553.2 | | 536.2 | 535.2 | 5 |
| 17 | 1,905.6 | | 1,888.6 | 1,887.6 | G | 452.2 | | 435.2 | 434.2 | 4 |
| 18 | 1,992.6 | | 1,975.6 | 1,974.6 | S | 395.2 | | 378.1 | 377.1 | 3 |
| 19 | 2,153.6 | | 2,136.6 | 2,135.6 | C+58 | 308.1 | | 291.1 | | 2 |
| 20 | 2,299.7 | | 2,282.7 | 2,281.7 | K | 147.1 | | 130.1 | | 1 |

Fig. 8B

| B | B Ions | B+2H | B+NH3 | B+H2O | AA | Y Ions | Y+2H | Y+NH3 | Y+H2O | Y |
|---|---|---|---|---|---|---|---|---|---|---|
| 1 | 174.1 | | | | M+42 | 2,227.7 | | 2,210.7 | 2,209.7 | 20 |
| 2 | 289.1 | | | 271.1 | D | 2,054.6 | | 2,037.6 | 2,036.6 | 19 |
| 3 | 386.1 | | | 368.1 | P | 1,939.6 | | 1,922.6 | 1,921.6 | 18 |
| 4 | 500.2 | | 483.2 | 482.2 | N | 1,842.6 | | 1,825.5 | 1,824.5 | 17 |
| 5 | 661.2 | | 644.2 | 643.2 | C+58 | 1,728.5 | | 1,711.5 | 1,710.5 | 16 |
| 6 | 748.2 | | 731.2 | 730.2 | S | 1,567.5 | | 1,550.5 | 1,549.5 | 15 |
| 7 | 909.2 | | 892.2 | 891.2 | C+58 | 1,480.5 | | 1,463.4 | 1,462.5 | 14 |
| 8 | 980.3 | | 963.3 | 962.3 | A | 1,319.5 | | 1,302.4 | 1,301.4 | 13 |
| 9 | 1,081.3 | | 1,064.3 | 1,063.3 | T | 1,248.4 | | 1,231.4 | 1,230.4 | 12 |
| 10 | 1,138.3 | | 1,121.3 | 1,120.3 | G | 1,147.4 | | 1,130.3 | 1,129.4 | 11 |
| 11 | 1,195.4 | | 1,178.3 | 1,177.4 | G | 1,090.3 | | 1,073.3 | 1,072.3 | 10 |
| 12 | 1,282.4 | | 1,265.4 | 1,264.4 | S | 1,033.3 | | 1,016.3 | 1,015.3 | 9 |
| 13 | 1,443.4 | | 1,426.4 | 1,425.4 | C+58 | 946.3 | | 929.3 | 928.3 | 8 |
| 14 | 1,544.5 | | 1,527.4 | 1,526.5 | T | 785.3 | | 768.3 | 767.3 | 7 |
| 15 | 1,705.5 | | 1,688.5 | 1,687.5 | C+58 | 684.2 | | 667.2 | 666.2 | 6 |
| 16 | 1,776.5 | | 1,759.5 | 1,758.5 | A | 523.2 | | 506.2 | 505.2 | 5 |
| 17 | 1,833.5 | | 1,816.5 | 1,815.5 | G | 452.2 | | 435.2 | 434.2 | 4 |
| 18 | 1,920.6 | | 1,903.5 | 1,902.6 | S | 395.2 | | 378.1 | 377.1 | 3 |
| 19 | 2,081.6 | | 2,064.6 | 2,063.6 | C+58 | 308.1 | | 291.1 | | 2 |
| 20 | 2,227.7 | | 2,210.7 | 2,209.7 | K | 147.1 | | 130.1 | | 1 |

Fig. 9B

| B | B Ions | B+2H | B-NH3 | B-H2O | AA | Y Ions | Y+2H | Y-NH3 | Y-H2O | Y |
|---|---|---|---|---|---|---|---|---|---|---|
| 1 | 174.1 | | | | M+42 | 2,239.7 | | 2,222.7 | 2,221.7 | 20 |
| 2 | 289.1 | | | 271.1 | D | 2,066.7 | | 2,049.6 | 2,048.7 | 19 |
| 3 | 386.1 | | | 368.1 | P | 1,951.6 | | 1,934.6 | 1,933.6 | 18 |
| 4 | 500.2 | | 483.2 | 482.2 | N | 1,854.6 | | 1,837.6 | 1,836.6 | 17 |
| 5 | 661.2 | | 644.2 | 643.2 | C+58 | 1,740.6 | | 1,723.5 | 1,722.5 | 16 |
| 6 | 748.2 | | 731.2 | 730.2 | S | 1,579.5 | | 1,562.5 | 1,561.5 | 15 |
| 7 | 909.2 | | 892.2 | 891.2 | C+58 | 1,492.5 | | 1,475.5 | 1,474.5 | 14 |
| 8 | 980.3 | | 963.3 | 962.3 | A | 1,331.5 | | 1,314.5 | 1,313.5 | 13 |
| 9 | 1,051.3 | | 1,034.3 | 1,033.3 | A | 1,260.5 | | 1,243.4 | 1,242.4 | 12 |
| 10 | 1,108.3 | | 1,091.3 | 1,090.3 | G | 1,189.4 | | 1,172.4 | 1,171.4 | 11 |
| 11 | 1,207.4 | | 1,190.4 | 1,189.4 | V | 1,132.4 | | 1,115.4 | 1,114.4 | 10 |
| 12 | 1,294.4 | | 1,277.4 | 1,276.4 | S | 1,033.3 | | 1,016.3 | 1,015.3 | 9 |
| 13 | 1,455.5 | | 1,438.4 | 1,437.4 | C+58 | 946.3 | | 929.3 | 928.3 | 8 |
| 14 | 1,556.5 | | 1,539.5 | 1,538.5 | T | 785.3 | | 768.3 | 767.3 | 7 |
| 15 | 1,717.5 | | 1,700.5 | 1,699.5 | C+58 | 684.2 | | 667.2 | 666.2 | 6 |
| 16 | 1,788.6 | | 1,771.5 | 1,770.5 | A | 523.2 | | 506.2 | 505.2 | 5 |
| 17 | 1,845.6 | | 1,828.5 | 1,827.6 | G | 452.2 | | 435.2 | 434.2 | 4 |
| 18 | 1,932.6 | | 1,915.6 | 1,914.6 | S | 395.2 | | 378.1 | 377.1 | 3 |
| 19 | 2,093.6 | | 2,076.6 | 2,075.6 | C+58 | 308.1 | | 291.1 | | 2 |
| 20 | 2,239.7 | | 2,222.7 | 2,221.7 | K | 147.1 | | 130.1 | | 1 |

Fig. 10B

| B | B ions | B+2H | B+NH3 | B+H2O | AA | Y ions | Y+2H | Y+NH3 | Y+H2O | Y |
|---|---|---|---|---|---|---|---|---|---|---|
| 1 | 174.1 | | | | M+42 | 2,243.7 | | 2,226.7 | 2,225.7 | 20 |
| 2 | 289.1 | | | 271.1 | D | 2,070.6 | | 2,053.6 | 2,052.6 | 19 |
| 3 | 386.1 | | | 368.1 | P | 1,955.6 | | 1,938.6 | 1,937.6 | 18 |
| 4 | 500.2 | | 483.2 | 482.2 | N | 1,858.6 | | 1,841.5 | 1,840.5 | 17 |
| 5 | 661.2 | | 644.2 | 643.2 | C+58 | 1,744.5 | | 1,727.5 | 1,726.5 | 16 |
| 6 | 748.2 | | 731.2 | 730.2 | S | 1,583.5 | | 1,566.5 | 1,565.5 | 15 |
| 7 | 909.2 | | 892.2 | 891.2 | C+58 | 1,496.5 | | 1,479.4 | 1,478.5 | 14 |
| 8 | 980.3 | | 963.3 | 962.3 | A | 1,335.4 | | 1,318.4 | 1,317.4 | 13 |
| 9 | 1,081.3 | | 1,064.3 | 1,063.3 | T | 1,264.4 | | 1,247.4 | 1,246.4 | 12 |
| 10 | 1,138.3 | | 1,121.3 | 1,120.3 | G | 1,163.4 | | 1,146.3 | 1,145.4 | 11 |
| 11 | 1,195.4 | | 1,178.3 | 1,177.4 | G | 1,106.3 | | 1,089.3 | 1,088.3 | 10 |
| 12 | 1,282.4 | | 1,265.4 | 1,264.4 | S | 1,049.3 | | 1,032.3 | 1,031.3 | 9 |
| 13 | 1,443.4 | | 1,426.4 | 1,425.4 | C+58 | 962.3 | | 945.3 | 944.3 | 8 |
| 14 | 1,530.4 | | 1,513.4 | 1,512.4 | S | 801.3 | | 784.2 | 783.3 | 7 |
| 15 | 1,691.5 | | 1,674.4 | 1,673.5 | C+58 | 714.2 | | 697.2 | 696.2 | 6 |
| 16 | 1,762.5 | | 1,745.5 | 1,744.5 | A | 553.2 | | 536.2 | 535.2 | 5 |
| 17 | 1,849.5 | | 1,832.5 | 1,831.5 | S | 482.2 | | 465.2 | 464.2 | 4 |
| 18 | 1,936.6 | | 1,919.5 | 1,918.6 | S | 395.2 | | 378.1 | 377.1 | 3 |
| 19 | 2,097.6 | | 2,080.6 | 2,079.6 | C+58 | 308.1 | | 291.1 | | 2 |
| 20 | 2,243.7 | | 2,226.7 | 2,225.7 | K | 147.1 | | 130.1 | | 1 |

Fig. 11B

| B | B Ions | B+2H | B+NH3 | B+H2O | AA | Y Ions | Y+2H | Y+NH3 | Y+H2O | Y |
|---|---|---|---|---|---|---|---|---|---|---|
| 1 | 174.1 | | | | M+42 | 2,423.8 | | 2,406.7 | 2,405.8 | 21 |
| 2 | 289.1 | | | 271.1 | D | 2,250.7 | | 2,233.7 | 2,232.7 | 20 |
| 3 | 386.1 | | | 368.1 | P | 2,135.7 | | 2,118.7 | 2,117.7 | 19 |
| 4 | 515.2 | | | 497.2 | L | 2,038.6 | | 2,021.6 | 2,020.6 | 18 |
| 5 | 616.2 | | | 598.2 | T | 1,909.6 | | 1,892.6 | 1,891.6 | 17 |
| 6 | 777.2 | | | 759.2 | C+58 | 1,808.5 | | 1,791.5 | 1,790.5 | 16 |
| 7 | 874.3 | | | 856.3 | P | 1,647.5 | | 1,630.5 | 1,629.5 | 15 |
| 8 | 1,035.3 | | | 1,017.3 | C+58 | 1,550.5 | | 1,533.4 | 1,532.5 | 14 |
| 9 | 1,132.4 | | | 1,114.4 | P | 1,389.5 | | 1,372.4 | 1,371.4 | 13 |
| 10 | 1,219.4 | | | 1,201.4 | S | 1,292.4 | | 1,275.4 | 1,274.4 | 12 |
| 11 | 1,276.4 | | | 1,258.4 | G | 1,205.4 | | 1,188.3 | 1,187.4 | 11 |
| 12 | 1,333.4 | | | 1,315.4 | G | 1,148.4 | | 1,131.3 | 1,130.3 | 10 |
| 13 | 1,420.5 | | | 1,402.5 | S | 1,091.3 | | 1,074.3 | 1,073.3 | 9 |
| 14 | 1,581.5 | | | 1,563.5 | C+58 | 1,004.3 | | 987.3 | 986.3 | 8 |
| 15 | 1,682.5 | | | 1,664.5 | T | 843.3 | | 826.3 | 825.3 | 7 |
| 16 | 1,843.5 | | | 1,825.5 | C+58 | 742.2 | | 725.2 | 724.2 | 6 |
| 17 | 1,914.6 | | | 1,896.6 | A | 581.2 | | 564.2 | 563.2 | 5 |
| 18 | 2,029.6 | | | 2,011.6 | D | 510.2 | | 493.2 | 492.2 | 4 |
| 19 | 2,116.6 | | | 2,098.6 | S | 395.2 | | 378.1 | 377.1 | 3 |
| 20 | 2,277.7 | | | 2,259.6 | C+58 | 308.1 | | 291.1 | | 2 |
| 21 | 2,423.8 | | 2,406.7 | 2,405.8 | K | 147.1 | | 130.1 | | 1 |

Fig. 12B

| B | B Ions | B+2H | B-NH3 | B-H2O | AA | Y Ions | Y+2H | Y-NH3 | Y-H2O | Y |
|---|---|---|---|---|---|---|---|---|---|---|
| 1 | 174.1 | | | | M+42 | 2,269.7 | | 2,252.7 | 2,251.7 | 20 |
| 2 | 289.1 | | | 271.1 | D | 2,096.7 | | 2,079.7 | 2,078.7 | 19 |
| 3 | 386.1 | | 368.1 | P | 1,981.7 | | 1,964.6 | 1,963.6 | 18 |
| 4 | 500.2 | | 483.2 | 482.2 | M | 1,884.6 | | 1,867.6 | 1,866.6 | 17 |
| 5 | 661.2 | | 644.2 | 643.2 | C+58 | 1,770.8 | | 1,753.5 | 1,752.6 | 16 |
| 6 | 748.2 | | 731.2 | 730.2 | S | 1,609.5 | | 1,592.5 | 1,591.5 | 15 |
| 7 | 909.2 | | 892.2 | 891.2 | C+58 | 1,522.5 | | 1,505.5 | 1,504.5 | 14 |
| 8 | 980.3 | | 963.3 | 962.3 | A | 1,361.5 | | 1,344.5 | 1,343.5 | 13 |
| 9 | 1,051.3 | | 1,034.3 | 1,033.3 | A | 1,290.5 | | 1,273.4 | 1,272.5 | 12 |
| 10 | 1,108.3 | | 1,091.3 | 1,090.3 | G | 1,219.4 | | 1,202.4 | 1,201.4 | 11 |
| 11 | 1,207.4 | | 1,190.4 | 1,189.4 | V | 1,162.4 | | 1,145.4 | 1,144.4 | 10 |
| 12 | 1,294.4 | | 1,277.4 | 1,276.4 | S | 1,063.3 | | 1,046.3 | 1,045.3 | 9 |
| 13 | 1,455.5 | | 1,438.4 | 1,437.4 | C+58 | 976.3 | | 959.3 | 958.3 | 8 |
| 14 | 1,556.5 | | 1,539.5 | 1,538.5 | T | 815.3 | | 798.3 | 797.3 | 7 |
| 15 | 1,717.5 | | 1,700.5 | 1,699.5 | C+58 | 714.2 | | 697.2 | 696.2 | 6 |
| 16 | 1,788.6 | | 1,771.5 | 1,770.5 | A | 553.2 | | 536.2 | 535.2 | 5 |
| 17 | 1,875.6 | | 1,858.6 | 1,857.6 | S | 482.2 | | 465.2 | 464.2 | 4 |
| 18 | 1,962.6 | | 1,945.6 | 1,944.6 | S | 395.2 | | 378.1 | 377.1 | 3 |
| 19 | 2,123.6 | | 2,106.6 | 2,105.6 | C+58 | 300.1 | | 291.1 | | 2 |
| 20 | 2,269.7 | | 2,252.7 | 2,251.7 | K | 147.1 | | 130.1 | | 1 |

Fig. 13B

| B | B Ions | B+2H | B-NH3 | B+H2O | AA | Y Ions | Y+2H | Y-NH3 | Y-H2O | Y |
|---|---|---|---|---|---|---|---|---|---|---|
| 1 | 174.1 | | | | M+42 | 2,257.7 | | 2,240.7 | 2,239.7 | 20 |
| 2 | 289.1 | | | 271.1 | D | 2,084.6 | | 2,067.6 | 2,066.6 | 19 |
| 3 | 386.1 | | | 368.1 | P | 1,969.6 | | 1,952.6 | 1,951.6 | 18 |
| 4 | 500.2 | | | 482.2 | N | 1,872.6 | | 1,855.5 | 1,854.6 | 17 |
| 5 | 661.2 | | 483.2 | 643.2 | C+58 | 1,758.5 | | 1,741.5 | 1,740.5 | 16 |
| 6 | 748.2 | | 644.2 | 730.2 | S | 1,597.5 | | 1,580.5 | 1,579.5 | 15 |
| 7 | 909.2 | | 731.2 | 891.2 | C+58 | 1,510.5 | | 1,493.5 | 1,492.5 | 14 |
| 8 | 980.3 | | 892.2 | 962.3 | A | 1,349.5 | | 1,332.4 | 1,331.5 | 13 |
| 9 | 1,081.3 | | 963.3 | 1,063.3 | T | 1,278.4 | | 1,261.4 | 1,260.4 | 12 |
| 10 | 1,138.3 | | 1,064.3 | 1,120.3 | G | 1,177.4 | | 1,160.4 | 1,159.4 | 11 |
| 11 | 1,195.4 | | 1,121.3 | 1,177.4 | G | 1,120.4 | | 1,103.3 | 1,102.3 | 10 |
| 12 | 1,282.4 | | 1,178.3 | 1,264.4 | S | 1,063.3 | | 1,046.3 | 1,045.3 | 9 |
| 13 | 1,443.4 | | 1,265.4 | 1,425.4 | C+58 | 976.3 | | 959.3 | 958.3 | 8 |
| 14 | 1,544.5 | | 1,426.4 | 1,526.5 | T | 815.3 | | 798.3 | 797.3 | 7 |
| 15 | 1,705.5 | | 1,527.4 | 1,687.5 | C+58 | 714.2 | | 697.2 | 696.2 | 6 |
| 16 | 1,806.5 | | 1,688.5 | 1,788.5 | T | 553.2 | | 536.2 | 535.2 | 5 |
| 17 | 1,863.5 | | 1,789.5 | 1,845.5 | G | 452.2 | | 435.2 | 434.2 | 4 |
| 18 | 1,950.6 | | 1,846.5 | 1,932.6 | S | 395.2 | | 378.1 | 377.1 | 3 |
| 19 | 2,111.6 | | 1,933.6 | 2,093.6 | C+58 | 308.1 | | 291.1 | | 2 |
| 20 | 2,257.7 | | 2,094.6 | 2,239.7 | K | 147.1 | | 130.1 | | 1 |

Fig. 14B

| B | B Ions | B+2H | B-NH3 | B-H2O | AA | Y Ions | Y+2H | Y-NH3 | Y-H2O | Y |
|---|---|---|---|---|---|---|---|---|---|---|
| 1 | 174.1 | | | | M+42 | 2,251.7 | | 2,234.7 | 2,233.7 | 20 |
| 2 | 289.1 | | | 271.1 | D | 2,078.7 | | 2,061.6 | 2,060.7 | 19 |
| 3 | 386.1 | | | 368.1 | P | 1,963.6 | | 1,946.6 | 1,945.6 | 18 |
| 4 | 500.2 | | 483.2 | 482.2 | N | 1,866.6 | | 1,849.6 | 1,848.6 | 17 |
| 5 | 661.2 | | 644.2 | 643.2 | C+58 | 1,752.6 | | 1,735.5 | 1,734.5 | 16 |
| 6 | 748.2 | | 731.2 | 730.2 | S | 1,591.5 | | 1,574.5 | 1,573.5 | 15 |
| 7 | 909.2 | | 892.2 | 891.2 | C+58 | 1,504.5 | | 1,487.5 | 1,486.5 | 14 |
| 8 | 996.3 | | 979.2 | 978.3 | S | 1,343.5 | | 1,326.5 | 1,325.5 | 13 |
| 9 | 1,093.3 | | 1,076.3 | 1,075.3 | P | 1,256.5 | | 1,239.4 | 1,238.4 | 12 |
| 10 | 1,192.4 | | 1,175.4 | 1,174.4 | V | 1,159.4 | | 1,142.4 | 1,141.4 | 11 |
| 11 | 1,249.4 | | 1,232.4 | 1,231.4 | G | 1,060.3 | | 1,043.3 | 1,042.3 | 10 |
| 12 | 1,336.4 | | 1,319.4 | 1,318.4 | S | 1,003.3 | | 986.3 | 985.3 | 9 |
| 13 | 1,497.5 | | 1,480.4 | 1,479.5 | C+58 | 916.3 | | 899.3 | 898.3 | 8 |
| 14 | 1,568.5 | | 1,551.5 | 1,550.5 | A | 755.3 | | 738.2 | 737.3 | 7 |
| 15 | 1,729.5 | | 1,712.5 | 1,711.5 | C+58 | 684.2 | | 667.2 | 666.2 | 6 |
| 16 | 1,800.6 | | 1,783.5 | 1,782.5 | A | 523.2 | | 506.2 | 505.2 | 5 |
| 17 | 1,857.6 | | 1,840.5 | 1,839.6 | G | 452.2 | | 435.2 | 434.2 | 4 |
| 18 | 1,944.6 | | 1,927.6 | 1,926.6 | S | 395.2 | | 378.1 | 377.1 | 3 |
| 19 | 2,105.6 | | 2,088.6 | 2,087.6 | C+58 | 308.1 | | 291.1 | | 2 |
| 20 | 2,251.7 | | 2,234.7 | 2,233.7 | K | 147.1 | | 130.1 | | 1 |

*Fig. 15B*

| B | B Ions | B+2H | B-NH3 | B+H2O | AA | Y Ions | Y+2H | Y-NH3 | Y-H2O | Y |
|---|--------|------|-------|-------|-----|--------|------|-------|-------|---|
| 1 | 174.1 | | | | M+42 | 2,255.7 | | 2,238.7 | 2,237.7 | 20 |
| 2 | 289.1 | | | | D | 2,082.6 | | 2,065.6 | 2,064.6 | 19 |
| 3 | 386.1 | | 271.1 | | P | 1,967.6 | | 1,950.6 | 1,949.6 | 18 |
| 4 | 500.2 | | 368.1 | | M | 1,870.6 | | 1,853.5 | 1,852.5 | 17 |
| 5 | 661.2 | | 483.2 | 482.2 | C+58 | 1,756.5 | | 1,739.5 | 1,738.5 | 16 |
| 6 | 748.2 | | 644.2 | 643.2 | S | 1,595.5 | | 1,578.5 | 1,577.5 | 15 |
| 7 | 909.2 | | 731.2 | 730.2 | C+58 | 1,508.5 | | 1,491.4 | 1,490.5 | 14 |
| 8 | 980.3 | | 892.2 | 891.2 | A | 1,347.4 | | 1,330.4 | 1,329.4 | 13 |
| 9 | 1,051.3 | | 963.3 | 962.3 | A | 1,276.4 | | 1,259.4 | 1,258.4 | 12 |
| 10 | 1,108.3 | | 1,034.3 | 1,033.3 | G | 1,205.4 | | 1,188.3 | 1,187.4 | 11 |
| 11 | 1,223.4 | | 1,091.3 | 1,090.3 | D | 1,148.4 | | 1,131.3 | 1,130.3 | 10 |
| 12 | 1,310.4 | | 1,206.3 | 1,205.4 | S | 1,033.3 | | 1,016.3 | 1,015.3 | 9 |
| 13 | 1,471.4 | | 1,293.4 | 1,292.4 | C+58 | 946.3 | | 929.3 | 928.3 | 8 |
| 14 | 1,572.5 | | 1,454.4 | 1,453.4 | T | 785.3 | | 768.3 | 767.3 | 7 |
| 15 | 1,733.5 | | 1,555.4 | 1,554.4 | C+58 | 684.2 | | 667.2 | 666.2 | 6 |
| 16 | 1,804.5 | | 1,716.4 | 1,715.5 | A | 523.2 | | 506.2 | 505.2 | 5 |
| 17 | 1,861.5 | | 1,787.5 | 1,786.5 | G | 452.2 | | 435.2 | 434.2 | 4 |
| 18 | 1,862.6 | | 1,844.5 | 1,843.5 | S | 395.2 | | 378.1 | 377.1 | 3 |
| 19 | 2,109.6 | | 1,931.5 | 1,930.6 | C+58 | 308.1 | | 291.1 | | 2 |
| 20 | 2,255.7 | | 2,092.6 | 2,091.6 | K | 147.1 | | 130.1 | | 1 |

Fig. 16B

| B | B Ions | B+2H | B-NH3 | B-H2O | AA | Y Ions | Y+2H | Y-NH3 | Y-H2O | Y |
|---|---|---|---|---|---|---|---|---|---|---|
| 1 | 174.1 | | | | M+42 | 2,222.8 | | 2,205.7 | 2,204.8 | 20 |
| 2 | 289.1 | | | 271.1 | D | 2,048.7 | | 2,032.7 | 2,031.7 | 19 |
| 3 | 386.1 | | | 368.1 | P | 1,934.7 | | 1,917.7 | 1,916.7 | 18 |
| 4 | 500.2 | | 483.2 | 482.2 | N | 1,837.6 | | 1,820.6 | 1,819.6 | 17 |
| 5 | 660.2 | | 643.2 | 642.2 | C+57 | 1,723.6 | | 1,706.6 | 1,705.6 | 16 |
| 6 | 747.2 | | 730.2 | 729.2 | S | 1,563.6 | | 1,546.5 | 1,545.6 | 15 |
| 7 | 907.3 | | 890.2 | 889.3 | C+57 | 1,476.5 | | 1,459.5 | 1,458.5 | 14 |
| 8 | 978.3 | | 961.3 | 960.3 | A | 1,316.5 | | 1,299.5 | 1,298.5 | 13 |
| 9 | 1,079.4 | | 1,062.3 | 1,061.3 | T | 1,245.5 | | 1,228.4 | 1,227.5 | 12 |
| 10 | 1,136.4 | | 1,119.4 | 1,118.4 | G | 1,144.4 | | 1,127.4 | 1,126.4 | 11 |
| 11 | 1,193.4 | | 1,176.4 | 1,175.4 | G | 1,087.4 | | 1,070.4 | 1,069.4 | 10 |
| 12 | 1,280.4 | | 1,263.4 | 1,262.4 | S | 1,030.4 | | 1,013.3 | 1,012.4 | 9 |
| 13 | 1,440.5 | | 1,423.4 | 1,422.5 | C+57 | 943.3 | | 926.3 | 925.3 | 8 |
| 14 | 1,541.5 | | 1,524.5 | 1,523.5 | T | 783.3 | | 766.3 | 765.3 | 7 |
| 15 | 1,701.5 | | 1,684.5 | 1,683.5 | C+57 | 682.3 | | 665.2 | 664.3 | 6 |
| 16 | 1,772.6 | | 1,755.6 | 1,754.6 | A | 522.2 | | 505.2 | 504.2 | 5 |
| 17 | 1,829.6 | | 1,812.6 | 1,811.6 | G | 451.2 | | 434.2 | 433.2 | 4 |
| 18 | 1,916.6 | | 1,899.6 | 1,898.6 | S | 394.2 | | 377.1 | 376.2 | 3 |
| 19 | 2,076.7 | | 2,059.6 | 2,058.7 | C+57 | 307.1 | | 290.1 | | 2 |
| 20 | 2,222.8 | | 2,205.7 | 2,204.8 | K | 147.1 | | 130.1 | | 1 |

Fig. 17B

| B | B Ions | B+2H | B-NH3 | B-H2O | AA | Y Ions | Y+2H | Y-NH3 | Y-H2O | Y |
|---|---|---|---|---|---|---|---|---|---|---|
| 1 | 174.1 | | | | M+42 | 2,294.8 | | 2,277.8 | 2,276.8 | 20 |
| 2 | 289.1 | | | 271.1 | D | 2,121.8 | | 2,104.7 | 2,103.8 | 19 |
| 3 | 386.1 | | | 368.1 | P | 2,006.7 | | 1,989.7 | 1,988.7 | 18 |
| 4 | 500.2 | | 483.2 | 482.2 | N | 1,909.7 | | 1,892.7 | 1,891.7 | 17 |
| 5 | 660.2 | | 643.2 | 642.2 | C+57 | 1,795.7 | | 1,778.6 | 1,777.6 | 16 |
| 6 | 747.2 | | 730.2 | 729.2 | S | 1,635.6 | | 1,618.6 | 1,617.6 | 15 |
| 7 | 907.3 | | 890.2 | 889.3 | C+57 | 1,548.6 | | 1,531.6 | 1,530.6 | 14 |
| 8 | 1,008.3 | | 991.3 | 990.3 | T | 1,388.6 | | 1,371.5 | 1,370.5 | 13 |
| 9 | 1,109.4 | | 1,092.3 | 1,091.4 | T | 1,287.5 | | 1,270.5 | 1,269.5 | 12 |
| 10 | 1,166.4 | | 1,149.4 | 1,148.4 | G | 1,186.5 | | 1,169.4 | 1,168.5 | 11 |
| 11 | 1,265.5 | | 1,248.4 | 1,247.4 | V | 1,129.4 | | 1,112.4 | 1,111.4 | 10 |
| 12 | 1,352.5 | | 1,335.5 | 1,334.5 | S | 1,030.4 | | 1,013.3 | 1,012.4 | 9 |
| 13 | 1,512.5 | | 1,495.5 | 1,494.5 | C+57 | 943.3 | | 926.3 | 925.3 | 8 |
| 14 | 1,583.6 | | 1,566.5 | 1,565.5 | A | 783.3 | | 766.3 | 765.3 | 7 |
| 15 | 1,743.6 | | 1,726.6 | 1,725.6 | C+57 | 712.3 | | 695.2 | 694.3 | 6 |
| 16 | 1,844.6 | | 1,827.6 | 1,826.6 | T | 552.2 | | 535.2 | 534.2 | 5 |
| 17 | 1,901.7 | | 1,884.6 | 1,883.6 | G | 451.2 | | 434.2 | 433.2 | 4 |
| 18 | 1,988.7 | | 1,971.7 | 1,970.7 | S | 394.2 | | 377.1 | 376.2 | 3 |
| 19 | 2,148.7 | | 2,131.7 | 2,130.7 | C+57 | 307.1 | | 290.1 | | 2 |
| 20 | 2,294.8 | | 2,277.8 | 2,276.8 | K | 147.1 | | 130.1 | | 1 |

Fig. 18B

| B | B Ions | B+3H | B+NH3 | B+20 | AA | Y Ions | Y+3H | Y+NH3 | Y+H2O | Y |
|---|--------|------|-------|------|-----|--------|------|-------|-------|---|
| 1 | 174.1 | | | | M+42 | 2,418.8 | | 2,401.8 | 2,400.8 | 21 |
| 2 | 289.1 | | | 271.1 | D | 2,245.8 | | 2,228.8 | 2,227.8 | 20 |
| 3 | 386.1 | | | 368.1 | P | 2,130.8 | | 2,113.7 | 2,112.8 | 19 |
| 4 | 515.2 | | | 497.2 | E | 2,033.7 | | 2,016.7 | 2,015.7 | 18 |
| 5 | 616.2 | | | 598.2 | T | 1,904.7 | | 1,887.6 | 1,886.7 | 17 |
| 6 | 776.3 | | | 758.2 | C+57 | 1,803.6 | | 1,786.6 | 1,785.6 | 16 |
| 7 | 873.3 | | | 855.3 | P | 1,643.6 | | 1,626.6 | 1,625.6 | 15 |
| 8 | 1,033.3 | | | 1,015.3 | C+57 | 1,546.5 | | 1,529.5 | 1,528.5 | 14 |
| 9 | 1,130.4 | | | 1,112.4 | P | 1,386.5 | | 1,369.5 | 1,368.5 | 13 |
| 10 | 1,217.4 | | | 1,199.4 | S | 1,289.5 | | 1,272.4 | 1,271.4 | 12 |
| 11 | 1,274.4 | | | 1,256.4 | G | 1,202.4 | | 1,185.4 | 1,184.4 | 11 |
| 12 | 1,331.5 | | | 1,313.5 | G | 1,145.4 | | 1,128.4 | 1,127.4 | 10 |
| 13 | 1,418.5 | | | 1,400.5 | S | 1,088.4 | | 1,071.4 | 1,070.4 | 9 |
| 14 | 1,578.5 | | | 1,560.5 | C+57 | 1,001.3 | | 984.3 | 983.3 | 8 |
| 15 | 1,679.6 | | | 1,661.6 | T | 841.3 | | 824.3 | 823.3 | 7 |
| 16 | 1,839.6 | | | 1,821.6 | C+57 | 740.3 | | 723.2 | 722.3 | 6 |
| 17 | 1,910.6 | | | 1,892.6 | A | 580.2 | | 563.2 | 562.2 | 5 |
| 18 | 2,025.7 | | | 2,007.7 | D | 509.2 | | 492.2 | 491.2 | 4 |
| 19 | 2,112.7 | | | 2,094.7 | S | 394.2 | | 377.1 | 376.2 | 3 |
| 20 | 2,272.7 | | | 2,254.7 | C+57 | 307.1 | | 290.1 | | 2 |
| 21 | 2,418.8 | | 2,401.8 | 2,400.8 | K | 147.1 | | 130.1 | | 1 |

*Fig. 19B*

| B | B Ions | B+2H | B+NH3 | B+H2O | AA | Y Ions | Y+2H | Y+NH3 | Y+H2O | Y |
|---|---|---|---|---|---|---|---|---|---|---|
| 1 | 174.1 | | | | M+42 | 2,264.8 | | 2,247.8 | 2,246.8 | 20 |
| 2 | 289.1 | | | 271.1 | D | 2,091.8 | | 2,074.7 | 2,073.8 | 19 |
| 3 | 386.1 | | | 368.1 | P | 1,976.7 | | 1,959.7 | 1,958.7 | 18 |
| 4 | 500.2 | | 483.2 | 482.2 | N | 1,879.7 | | 1,862.7 | 1,861.7 | 17 |
| 5 | 660.2 | | 643.2 | 642.2 | C+57 | 1,765.6 | | 1,748.6 | 1,747.6 | 16 |
| 6 | 747.2 | | 730.2 | 729.2 | S | 1,605.6 | | 1,588.6 | 1,587.6 | 15 |
| 7 | 907.3 | | 890.2 | 889.3 | C+57 | 1,518.6 | | 1,501.6 | 1,500.6 | 14 |
| 8 | 978.3 | | 961.3 | 960.3 | A | 1,358.5 | | 1,341.5 | 1,340.5 | 13 |
| 9 | 1,049.3 | | 1,032.3 | 1,031.3 | A | 1,287.5 | | 1,270.5 | 1,269.5 | 12 |
| 10 | 1,106.4 | | 1,089.3 | 1,088.4 | G | 1,216.5 | | 1,199.4 | 1,198.5 | 11 |
| 11 | 1,205.4 | | 1,188.4 | 1,187.4 | V | 1,159.5 | | 1,142.4 | 1,141.4 | 10 |
| 12 | 1,292.5 | | 1,275.4 | 1,274.5 | S | 1,060.4 | | 1,043.4 | 1,042.4 | 9 |
| 13 | 1,452.5 | | 1,435.5 | 1,434.5 | C+57 | 973.4 | | 956.3 | 955.3 | 8 |
| 14 | 1,553.5 | | 1,536.5 | 1,535.5 | T | 813.3 | | 796.3 | 795.3 | 7 |
| 15 | 1,713.6 | | 1,696.6 | 1,695.6 | C+57 | 712.3 | | 695.2 | 694.3 | 6 |
| 16 | 1,784.6 | | 1,767.6 | 1,766.6 | A | 552.2 | | 535.2 | 534.2 | 5 |
| 17 | 1,871.6 | | 1,854.6 | 1,853.6 | S | 481.2 | | 464.2 | 463.2 | 4 |
| 18 | 1,958.7 | | 1,941.7 | 1,940.7 | S | 394.2 | | 377.1 | 376.2 | 3 |
| 19 | 2,118.7 | | 2,101.7 | 2,100.7 | C+57 | 307.1 | | 290.1 | | 2 |
| 20 | 2,264.8 | | 2,247.8 | 2,246.8 | K | 147.1 | | 130.1 | | 1 |

Fig. 20B

| B | B ions | B+2H | B-NH3 | B-H2O | AA | Y ions | Y+2H | Y-NH3 | Y-H2O | Y |
|---|---|---|---|---|---|---|---|---|---|---|
| 1 | 174.1 | | | | M+42 | 2,246.8 | | 2,229.8 | 2,228.8 | 20 |
| 2 | 289.1 | | | 271.1 | D | 2,073.8 | | 2,056.7 | 2,055.7 | 19 |
| 3 | 386.1 | | | 368.1 | P | 1,958.7 | | 1,941.7 | 1,940.7 | 18 |
| 4 | 500.2 | | 483.2 | 482.2 | N | 1,861.7 | | 1,844.6 | 1,843.7 | 17 |
| 5 | 660.2 | | 643.2 | 642.2 | C+57 | 1,747.6 | | 1,730.6 | 1,729.6 | 16 |
| 6 | 747.2 | | 730.2 | 729.2 | S | 1,587.6 | | 1,570.6 | 1,569.6 | 15 |
| 7 | 907.3 | | 890.2 | 889.3 | C+57 | 1,500.6 | | 1,483.5 | 1,482.6 | 14 |
| 8 | 994.3 | | 977.3 | 976.3 | S | 1,340.5 | | 1,323.5 | 1,322.5 | 13 |
| 9 | 1,091.4 | | 1,074.3 | 1,073.3 | P | 1,253.5 | | 1,236.5 | 1,235.5 | 12 |
| 10 | 1,190.4 | | 1,173.4 | 1,172.4 | V | 1,156.5 | | 1,139.4 | 1,138.4 | 11 |
| 11 | 1,247.4 | | 1,230.4 | 1,229.4 | G | 1,057.4 | | 1,040.4 | 1,039.4 | 10 |
| 12 | 1,334.5 | | 1,317.5 | 1,316.5 | S | 1,000.4 | | 983.3 | 982.4 | 9 |
| 13 | 1,494.5 | | 1,477.5 | 1,476.5 | C+57 | 913.3 | | 896.3 | 895.3 | 8 |
| 14 | 1,565.5 | | 1,548.5 | 1,547.5 | A | 753.3 | | 736.3 | 735.3 | 7 |
| 15 | 1,725.6 | | 1,708.6 | 1,707.6 | C+57 | 682.3 | | 665.2 | 664.3 | 6 |
| 16 | 1,796.6 | | 1,779.6 | 1,778.6 | A | 522.2 | | 505.2 | 504.2 | 5 |
| 17 | 1,853.6 | | 1,836.6 | 1,835.6 | G | 451.2 | | 434.2 | 433.2 | 4 |
| 18 | 1,940.7 | | 1,923.6 | 1,922.7 | S | 394.2 | | 377.1 | 376.2 | 3 |
| 19 | 2,100.7 | | 2,083.7 | 2,082.7 | C+57 | 307.1 | | 290.1 | | 2 |
| 20 | 2,246.8 | | 2,229.8 | 2,228.8 | K | 147.1 | | 130.1 | | 1 |

Fig. 21B

| B | B Ions | B+2H | B+NH3 | B-H2O | AA | Y Ions | Y+2H | Y+NH3 | Y-H2O | Y |
|---|---|---|---|---|---|---|---|---|---|---|
| 1 | 174.1 | | | | M+42 | 2,234.8 | | 2,217.8 | 2,216.8 | 20 |
| 2 | 289.1 | | | 271.1 | D | 2,061.8 | | 2,044.7 | 2,043.7 | 19 |
| 3 | 386.1 | | | 368.1 | P | 1,946.7 | | 1,929.7 | 1,928.7 | 18 |
| 4 | 500.2 | | 483.2 | 482.2 | W | 1,849.7 | | 1,832.6 | 1,831.7 | 17 |
| 5 | 660.2 | | 643.2 | 642.2 | C+57 | 1,735.6 | | 1,718.6 | 1,717.6 | 16 |
| 6 | 747.2 | | 730.2 | 729.2 | S | 1,575.6 | | 1,558.6 | 1,557.6 | 15 |
| 7 | 907.3 | | 890.2 | 889.3 | C+57 | 1,488.6 | | 1,471.5 | 1,470.6 | 14 |
| 8 | 978.3 | | 961.3 | 960.3 | A | 1,328.5 | | 1,311.5 | 1,310.5 | 13 |
| 9 | 1,049.3 | | 1,032.3 | 1,031.3 | A | 1,257.5 | | 1,240.5 | 1,239.5 | 12 |
| 10 | 1,106.4 | | 1,089.3 | 1,088.4 | G | 1,186.5 | | 1,169.4 | 1,168.5 | 11 |
| 11 | 1,205.4 | | 1,188.4 | 1,187.4 | V | 1,129.4 | | 1,112.4 | 1,111.4 | 10 |
| 12 | 1,292.5 | | 1,275.4 | 1,274.5 | S | 1,030.4 | | 1,013.3 | 1,012.4 | 9 |
| 13 | 1,452.5 | | 1,435.5 | 1,434.5 | C+57 | 943.3 | | 926.3 | 925.3 | 8 |
| 14 | 1,553.5 | | 1,536.5 | 1,535.5 | T | 783.3 | | 766.3 | 765.3 | 7 |
| 15 | 1,713.6 | | 1,696.6 | 1,695.6 | C+57 | 682.3 | | 665.2 | 664.3 | 6 |
| 16 | 1,784.6 | | 1,787.6 | 1,766.6 | A | 522.2 | | 505.2 | 504.2 | 5 |
| 17 | 1,841.6 | | 1,824.6 | 1,823.6 | G | 451.2 | | 434.2 | 433.2 | 4 |
| 18 | 1,928.7 | | 1,911.6 | 1,910.7 | S | 394.2 | | 377.1 | 376.2 | 3 |
| 19 | 2,088.7 | | 2,071.7 | 2,070.7 | C+57 | 307.1 | | 290.1 | | 2 |
| 20 | 2,234.8 | | 2,217.8 | 2,216.8 | K | 147.1 | | 130.1 | | 1 |

Fig. 22B

| B | B Ions | B+2H | B+NH3 | B+H2O | AA | Y Ions | Y+2H | Y+NH3 | Y+H2O | Y |
|---|---|---|---|---|---|---|---|---|---|---|
| 1 | 174.1 | | | | M+42 | 2,250.8 | | 2,233.7 | 2,232.8 | 20 |
| 2 | 289.1 | | | 271.1 | D | 2,077.7 | | 2,060.7 | 2,059.7 | 19 |
| 3 | 386.1 | | | 368.1 | P | 1,962.7 | | 1,945.7 | 1,944.7 | 18 |
| 4 | 500.2 | | 483.2 | 482.2 | N | 1,865.6 | | 1,848.6 | 1,847.6 | 17 |
| 5 | 660.2 | | 643.2 | 642.2 | C+57 | 1,751.6 | | 1,734.6 | 1,733.6 | 16 |
| 6 | 747.2 | | 730.2 | 729.2 | S | 1,591.6 | | 1,574.5 | 1,573.5 | 15 |
| 7 | 907.3 | | 890.2 | 889.3 | C+57 | 1,504.5 | | 1,487.5 | 1,486.5 | 14 |
| 8 | 978.3 | | 961.3 | 960.3 | A | 1,344.5 | | 1,327.5 | 1,326.5 | 13 |
| 9 | 1,049.3 | | 1,032.3 | 1,031.3 | A | 1,273.5 | | 1,256.4 | 1,255.5 | 12 |
| 10 | 1,106.4 | | 1,089.3 | 1,088.4 | G | 1,202.4 | | 1,185.4 | 1,184.4 | 11 |
| 11 | 1,221.4 | | 1,204.4 | 1,203.4 | D | 1,145.4 | | 1,128.4 | 1,127.4 | 10 |
| 12 | 1,308.4 | | 1,291.4 | 1,290.4 | S | 1,030.4 | | 1,013.3 | 1,012.4 | 9 |
| 13 | 1,468.5 | | 1,451.4 | 1,450.4 | C+57 | 943.3 | | 926.3 | 925.3 | 8 |
| 14 | 1,569.5 | | 1,552.5 | 1,551.5 | T | 783.3 | | 766.3 | 765.3 | 7 |
| 15 | 1,729.5 | | 1,712.5 | 1,711.5 | C+57 | 682.3 | | 665.2 | 664.3 | 6 |
| 16 | 1,800.6 | | 1,783.5 | 1,782.6 | A | 522.2 | | 505.2 | 504.2 | 5 |
| 17 | 1,857.6 | | 1,840.6 | 1,839.6 | G | 451.2 | | 434.2 | 433.2 | 4 |
| 18 | 1,944.6 | | 1,927.6 | 1,926.6 | S | 394.2 | | 377.1 | 376.2 | 3 |
| 19 | 2,104.7 | | 2,087.6 | 2,086.6 | C+57 | 307.1 | | 290.1 | | 2 |
| 20 | 2,250.8 | | 2,233.7 | 2,232.8 | K | 147.1 | | 130.1 | | 1 |

Fig. 23B

METHOD FOR QUANTIFYING PROTEINS AND ISOFORMS THEREOF

CROSS-REFERENCE TO RELATED APPLICATIONS

This application is a U.S. National Stage Application under 35 U.S.C. §371 of PCT/US2013/041651 filed on May 17, 2013, and published on Nov. 21, 2013 as WO 2013/173756, which claims benefit of the priority filing date of U.S. patent application Ser. No.61/649,118, filed May 18, 2012, the contents of which are specifically incorporated herein by reference in their entirety.

STATEMENT REGARDING FEDERALLY SPONSORED RESEARCH

This invention was made with government support by the National Institutes of Health, grant no. P20RR016471 and by the National Institute of General Medical Sciences, grant no. P20 GM103442. The government has certain rights in the invention.

BACKGROUND

Disease prognosis is related to early and accurate diagnosis. For example, the outcome of cancer and exposure to toxins such as heavy metals can be ameliorated by early detection. Diagnosis of many diseases, including many cancers, relies on expensive magnetic resonance imaging (MRI) and computed tomography (CT) scans, and definitive diagnoses often require invasive biopsy of tissue.

More accurate tests can facilitate early detection of disease, aid physicians in therapeutic decision-making, avoid disease progression, be utilized as a potential prognostic marker for patient outcome and lower treatment costs.

SUMMARY

As described herein, the quantities of metallothionein protein isomers in test samples are diagnostic of various diseases, including diseases relating to heavy metal exposure and cancer. However, some metallothionein isomers may be of more diagnostic value than others. Methods are currently available for distinguishing at least some metallothionein isomers by detection of mRNA expression. However, as shown herein, the mRNA levels of metallothionein isomers do not necessarily correlate with the amount of metallothionein protein actually present in cells. Thus, metallothionein mRNA levels are not a reliable indicator of the physiological role of metallothioneins in healthy and diseased tissues. Current methods for detecting metallothionein protein levels lack the specificity to distinguish the majority of human isoforms, in part because the sequences of the isomers are so similar. Moreover, the amounts of metallothionein isomers are relatively low in most biological samples, and the presence of metallothionein peptides is often masked by the presence of peptides from more abundant proteins. Furthermore, metallothioneins are particularly sensitive to oxidization. Therefore, processes to enrich metallothionein peptides and strategies to reduce adventitious mass-changing oxidization are needed to allow reliable detection and quantification of metallothionein (e.g., by mass spectroscopy). The methods described herein solve these problems and provide reliable means for, either individually or simultaneously, distinguishing and quantifying the various metallothionein isoforms.

As described herein, each human metallothionein protein isoform can be processed to generate a unique, acetylated N-terminal tryptic peptide that can be identified, detected and quantified by mass spectroscopy. Each metallothionein isomer can therefore be distinguished from other metallothionein isoforms by the mass of its cysteine-rich, hydrophilic N-terminal peptide.

Detection of the amounts and types of metallothionein protein isomers can facilitate early detection of disease, aid physicians in therapeutic decision-making, avoid disease progression, be utilized as potential prognostic markers for patient outcome, and lower treatment costs.

DESCRIPTION OF THE FIGURES

FIG. 1A-1D show MALDI-TOF/TOF mass spectra of light and heavy labeled acetylated N-terminal tryptic metallothionein peptides in the cytosol of human kidney epithelial HK-2 cells containing a stably transfected human MT-3 expression cassette, as well as the sequences of the peptides. FIG. 1A shows a mass spectrum of equal concentrations of Cd-induced cytosol that were each labeled with either light or heavy iodoacetamide. There is a 5 Da mass shift from the light (grey) MT-2 monoisotopic peak (m/z 2250.7) to the heavy (black) MT-2 monoisotopic peak (m/z 2255.7). FIG. 1B illustrates a strong 1:1 correlation of retention time vs. monoisotopic peak intensity for light (grey) and heavy (black) acetylated N-terminal tryptic MT-2 peptides after correction of light-labeled peptide isotopic contribution ($6^{th}$ isotopic peak) to heavy-labeled peptide monoisotopic peak. FIG. 1C shows a 3-D LC-MS heat map of the light (grey) and heavy (black)-labeled acetylated N-terminal tryptic metallothionein peptides detected in the Cd-induced HK-2 MT-3 cytosol showing an equal 1:1 labeling. FIG. 1D shows an amino acid sequence alignment of human metallothionein isoforms. Residues that differ from the consensus sequence are highlighted in grey. Asterisks indicate invariant residues among MT1 and MT2 isoforms. All proteins are shown with N-terminal acetylation. The MT1A peptide (P04731) has SEQ ID NO:30. The MT1L peptide (Q93083) has SEQ ID NO:31. The MT1E peptide (P04732) has SEQ ID NO:32. The MT1G peptide (P13640-1) has SEQ ID NO:33. The MT1G peptide (P13640-2) has SEQ ID NO:34. The MT1F peptide (P04733) has SEQ ID NO:35. The MT2 peptide (P02795) has SEQ ID NO:36. The MT1H peptide (P80294) has SEQ ID NO:37. The MT1X peptide (P80297) has SEQ ID NO:38. The MT1B peptide (P07438) has SEQ ID NO:39. The MT1M peptide (Q8N339) has SEQ ID NO:40. The MT3 peptide has SEQ ID NO:41, while the MT4 peptide has SEQ ID NO: 42.

FIG. 3A shows a three-dimensional LC-MS heat map of light-(control) and heavy-(Cd-induced) labeled MT isoforms in the HK-2 MT-3 lysates. Grey cones display isoform levels in control while black cones display isoform levels in Cd-induced cells. FIG. 3B graphically illustrates relative fold induction calculated from the average monoisotopic peak intensities of light-labeled (control) to heavy-labeled (Cd-induced) acetylated N-terminal tryptic metallothionein peptides. Relative data show represent biological replicates where n=3. Error bars indicate the standard deviation around the mean.

FIG. 4A graphically illustrates absolute metallothionein protein expression in 300 µg control (grey) and Cd-induced (black) HK-2 MT-3 cytosol. Absolute protein levels were calculated from the average monoisotopic peak intensities of light-labeled (control or Cd-induced cytosol) to heavy-labeled acetylated N-terminal tryptic metallothionein standard peptides (~145 pmol/metallothionein isoform). FIG. 4B graphically illustrates absolute mRNA transcripts normalized to 18S rRNA from control (grey) and Cd-induced (black) cells. Protein and mRNA data represent biological replicates where n=3. Error bars indicate the standard deviation around the mean. A two-way ANOVA followed with a Bonferroni posttest was run on all data sets. Δ (no detection). * P<0.01.

FIG. 5A shows the absolute metallothionein protein expression in 300 µg control (grey hatched), estrogen receptor$^+$ (ER$^+$; solid grey), and estrogen receptor$^-$ (ER$^-$; black) breast cell cytosol. Absolute protein levels were calculated from the average monoisotopic peak intensity ratios of light-labeled (cytosol) to heavy-labeled acetylated N-terminal tryptic metallothionein standard peptides (~100 pmol/metallothionein isoform). FIG. 5B shows the absolute mRNA transcripts normalized to 18S rRNA from control, ER$^+$ (grey), and ER$^-$ (black) breast cells. Protein and mRNA data represents biological replicates where n=3. Error bars indicate the standard deviation around the mean. A two-way ANOVA followed with a Bonferroni posttest was run on all data sets. Significance was based on variation from control (MCF-10A). The symbol Δ means no detection was detected. The symbol * means P<0.05.

FIG. 6A-6B show a mass spectrum (MSMS; FIG. 6A) and a chart (FIG. 6B) summarizing mass spectral data for the synthesized human metallothionein-1H (MT-1H) peptide labeled with $^{15}$N and having SEQ ID NO:24.

FIG. 7A-7B show a mass spectrum (MSMS; FIG. 7A) and a chart (FIG. 7B) summarizing mass spectral data for the synthesized human metallothionein-1B (MT-1B) peptide labeled with $^{15}$N and having SEQ ID NO:19.

FIG. 8A-8B show a mass spectrum (MSMS; FIG. 8A) and a chart (FIG. 8B) summarizing mass spectral data for the synthesized human metallothionein-1M (MT-1M) peptide labeled with $^{15}$N and having SEQ ID NO:26.

FIG. 9A-9B show a mass spectrum (MSMS; FIG. 9A) and a chart (FIG. 9B) summarizing mass spectral data for the synthesized human metallothionein-1E (MT-1E) peptide labeled with $^{15}$N and having SEQ ID NO:20.

FIG. 10A-10B show a mass spectrum (MSMS; FIG. 10A) and a chart (FIG. 10B) summarizing mass spectral data for the synthesized human metallothionein-1F (MT-1F) peptide labeled with $^{15}$N and having SEQ ID NO:21.

FIG. 11A-11B show a mass spectrum (MSMS; FIG. 11A) and a chart (FIG. 11B) summarizing mass spectral data for the synthesized human metallothionein-1F (MT-1L) peptide labeled with $^{15}$N and having SEQ ID NO:25.

FIG. 12A-12B show a mass spectrum (MSMS; FIG. 12A) and a chart (FIG. 12B) summarizing mass spectral data for the synthesized human metallothionein-3 (MT-3) peptide labeled with $^{15}$N and having SEQ ID NO:29.

FIG. 13A-13B show a mass spectrum (MSMS; FIG. 13A) and a chart (FIG. 13B) summarizing mass spectral data for the synthesized human metallothionein-1G2 (MT-1G2) peptide labeled with $^{15}$N and having SEQ ID NO:23.

FIG. 14A-14B show a mass spectrum (MSMS; FIG. 14A) and a chart (FIG. 14B) summarizing mass spectral data for the synthesized human metallothionein-1G2 (MT-1A) peptide labeled with $^{15}$N and having SEQ ID NO:18.

FIG. 15A-15B show a mass spectrum (MSMS; FIG. 15A) and a chart (FIG. 15B) summarizing mass spectral data for the synthesized human metallothionein-1X (MT-1X) peptide labeled with $^{15}$N and having SEQ ID NO:27.

FIG. 16A-16B show a mass spectrum (MSMS; FIG. 16A) and a chart (FIG. 16B) summarizing mass spectral data for the synthesized human metallothionein-2 (MT-2) peptide labeled with $^{15}$N and having SEQ ID NO:28.

FIG. 17A-17B show a mass spectrum (MSMS; FIG. 17A) and a chart (FIG. 17B) summarizing mass spectral data for the unlabeled endogenous human metallothionein-1E (MT-1E) peptide that has SEQ ID NO:20.

FIG. 18A-18B show a mass spectrum (MSMS; FIG. 18A) and a chart (FIG. 18B) summarizing mass spectral data for the unlabeled endogenous human metallothionein-1E (MT-1M) peptide that has SEQ ID NO:26.

FIG. 19A-19B show a mass spectrum (MSMS; FIG. 19A) and a chart (FIG. 19B) summarizing mass spectral data for the unlabeled endogenous human metallothionein-3 (MT-3) peptide that has SEQ ID NO:29.

FIG. 20A-20B show a mass spectrum (MSMS; FIG. 20A) and a chart (FIG. 20B) summarizing mass spectral data for the unlabeled endogenous human metallothionein-1G2 (MT-1G2) peptide that has SEQ ID NO:23.

FIG. 21A-21B show a mass spectrum (MSMS; FIG. 21A) and a chart (FIG. 21B) summarizing mass spectral data for the unlabeled endogenous human metallothionein-1X (MT-1X) peptide that has SEQ ID NO:27.

FIG. 22A-22B show a mass spectrum (MSMS; FIG. 22A) and a chart (FIG. 22B) summarizing mass spectral data for the unlabeled endogenous human metallothionein-1F (MT-1F) peptide that has SEQ ID NO:21.

FIG. 23A-23B show a mass spectrum (MSMS; FIG. 23A) and a chart (FIG. 23B) summarizing mass spectral data for the unlabeled endogenous human metallothionein-2 (MT-2) peptide that has SEQ ID NO:28.

DETAILED DESCRIPTION

Figure 1A:
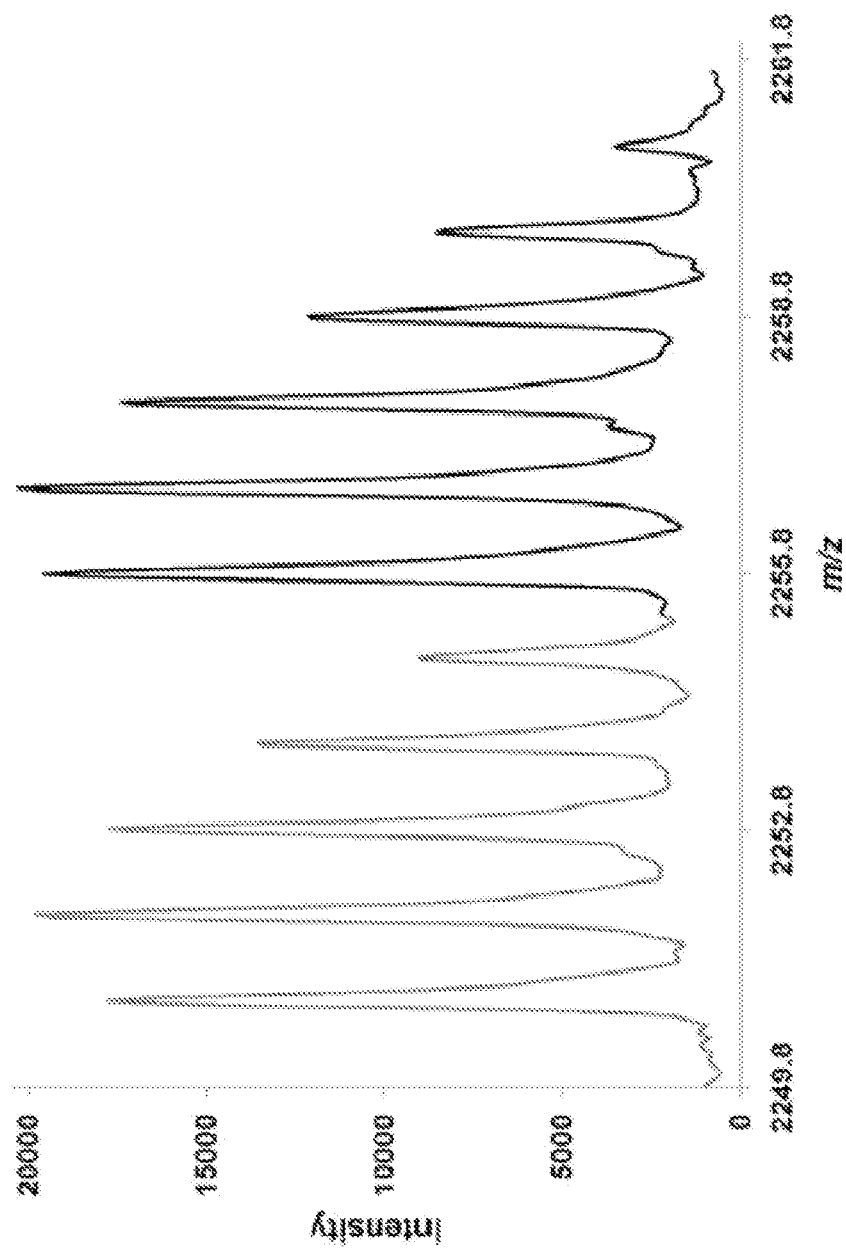

As described herein, each metallothionein protein isomer in a sample of interest can be separately detected and quantified. The methods described herein overcome the problems of currently available procedures, which cannot identify and quantify all the different isomers of metallothionein, or which rely upon unreliable mRNA quantification procedures. As shown herein, the level of metallothionein isomer mRNA does not necessarily accurately reflect the protein level of the corresponding metallothionein isomer. Accordingly, the methods described herein are uniquely suited for detection and quantification of metallothionein protein isomer levels, and for correlating isomer levels with disease states.

The methods for detecting and/or quantifying metallothionein isomer protein levels generally involve protein denaturation, reduction, alkylation, labeling, protease digestion, peptide separation, metallothionein peptide enrichment, quantitative mass spectrometry and combinations of such steps. These steps are described in more detail below.

Samples

Various samples can be evaluated using the methods described herein. The samples can be from any prokaryotic or eukaryotic species. In some instances, the samples are from a mammalian species such as a domesticated animal species, a zoo animal species, a primate species, or a human.

The samples can be tissue samples, cell samples, biological fluids, tissue biopsies, cultured cells, and combinations thereof. For example, the samples can include biological materials such as whole blood, bone marrow, blood serum, blood plasma, buffy coat preparations, saliva, cerebrospinal fluid, cellular cytosol, urine, sweat, tears, feces, saliva, seminal plasma, nipple aspirate fluid, nipple discharge, pancreatic juice and combinations thereof. The samples can be fresh, fixed (e.g., formalin-fixed), frozen (e.g., at −80° C.) and/or lyophilized samples.

Cells in the samples can be dispersed and disrupted prior to facilitate further processing. Tissues can be minced, crushed, sonicated or otherwise fragmented to release cells. The samples can be dispersed into solutions that contain antioxidants, chelators and/or protease inhibitors to avoid protein oxidation and/or degradation. Solutions can contain a buffer. Examples of solutions include Tris-buffered saline (e.g., 50 mM Tris-HCl, 150 mM NaCl, pH 8.0), phosphate-buffered saline (e.g., 50 mM sodium phosphate, 150 mM NaCl, pH 8.0), REACT6™ buffer solution obtained from Bethesda Research Labs (50 mM Tris-HCl, pH 7.1, 50 mM NaCl, 50 mM KCl, 6 mM $MgCl_2$), sodium phosphate solution (pH 5.0 to 12.0), and other solutions. Chelating agents that can be employed include diethylenetriaminepentaacetic acid (DTPA), ethylene-diaminetetraacetic acid (EDTA), ethylene glycol tetraacetic acid (EGTA) and the like. The solution can contain a detergent such as 0.1-1.0 vol % RapiGest, deoxycholic acid, Tween 20, or Nonidet p-40. In some cases, the detergent can be about 0.5% RapiGest or deoxycholic acid. The solutions can be kept cold (e.g., 2-10° C.) to reduce protease activity.

The solutions can contain agents that facilitate lysis of cells. For example, the solution can also be hypotonic to facilitate release of proteins from the cells. The solution can contain a detergent such as 0.1 to 1.0% by volume RapiGest, deoxycholic acid, Tween 20, sodium dodecyl sulfate, and/or Nonidet p-40. In some cases, the detergent can be about 0.5% RapiGest or deoxycholic acid. The cells can be disrupted by shear force, detergents, freezing and thawing and other available procedures. For example, the cells can be lysed by passage through a needle one or more times. The lysed cellular materials can be evaluated immediately or stored (e.g., at −80° C.) for later evaluation.

Protein Denaturation

The proteins in the samples can be denatured in the presence of a denaturant for a time and at a temperature sufficient to denature substantially all the proteins in the sample. Useful denaturants include chaotropic substances such as guanidinium salts, urea, ammonium, cesium, rubidium, potassium, or iodide salts. For example, the denaturant can be urea, guanidinium chloride, lithium perchlorate and the like.

Urea can be used at concentrations of about 6-8 mole/liter as a denaturant. Guanidinium chloride can be used at concentrations of about 6 mole/liter as a denaturant. Lithium perchlorate can be used at concentrations of about 4.5 mole/liter as a denaturant.

The samples are mixed with the denaturing agent(s) at an appropriate temperature and for an appropriate time. For example, denaturation can be performed at temperatures of about 2° C. to about 65° C. In some cases, denaturation can be performed at temperatures of about 4° C. to about 25° C. Denaturation is often complete within about 30 minutes-three hours of mixing with the denaturing agent. In many cases, denaturation is substantially complete within about one hour.

Reduction

The sample can be mixed with a reducing agent to stabilize free sulfhydryls of cysteines, minimize oxidation, and reduce disulfide bonds in peptides and proteins. Examples of reducing agent that can be used include dithiothreitol (DTT), 2-mercaptoethanol, Tris(2-carboxyethyl) phosphine (TCEP) and the like. Such reducing agent can be used at concentrations of about 0.1 mM to about 20 mM. In some cases concentrations of about 1 mM to about 10 mM, or about 2 mM to 7 mM are employed. Reduction can be performed at temperatures of about 4° C. to about 25° C. Reduction is typically complete within about 30 minutes to 3 hours of exposure to the reducing agent.

Alkylation and/or Labeling

The sulfhydryl groups on the metallothionein cysteine residues can be alkylated to prevent disulfide bond formation, which can complicate separation, identification and quantification of metallothionein isomers. Such alkylation can be performed with available alkylating agents such as iodoacetamide or iodoacetic acid. Iodoacetamide links a carbamidomethyl group to the sulfur atom on a cysteine:

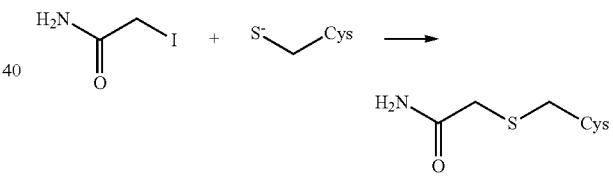

The metallothioneins can also be labeled to facilitate detection and/or quantification. As described herein, metallothioneins are cleaved to generate unique isomeric peptides that can be more readily manipulated (e.g. separated from other peptides), detected and quantified. The N-terminal regions of metallothioneins have greater amino acid sequence diversity than their C-termini (FIG. 1D). Hence, labeling metallothioneins somewhere in the N-terminal region facilitates generation of labeled isomeric peptides (after protease cleavage) that are unique and can be distinguished from each other.

Any means of labeling the metallothioneins can be employed so long as each metallothionein isomer, or a peptide therefrom, can be distinguished from the other metallothionein isomers and peptide therefrom. For example, the N-terminus or selected amino acid side chain moieties can be linked to a label. Metallothioneins also have about twenty cysteines, which for such small proteins is a high proportion of sulfhydryl-containing amino acids. These cysteines provide a convenient target for attachment of labels so that unique peptides from the various metallothionein isoforms can be distinguished from each other as well as from other peptides of about the same size. For example, the label can be attached to the metallothioneins during alkylation, acetylation, or other modification of cysteine residues.

In general, labels are used that do not negatively impact separation and/or detection of unique isomeric peptides generated upon cleavage of the metallothionein isomer. Labels that do not significantly change the molecular weight or size of such isomeric peptides are convenient for this purpose. For example, a label can be used that shifts the mass of the isomeric peptides by about 1 to about 20 Daltons per cysteine residue, for example, resulting in mass shifts of 5 to 100 Daltons for a peptide with five cysteines. Examples of labels that can be used include stable isotopes such as $^{13}C$, $^{15}N$, or deuterium.

Alkylation with $^{15}N$ (heavy) iodoacetamide, for example, provides a shift in mass of 1 Dalton per cysteine, or about 20 Daltons for an intact labeled metallothionein. An isomeric peptide cleaved from such a labeled metallothionein isomer could have a mass shift of less than 20 Daltons if cleavage removes one or more cysteines from the protein. As shown herein cleavage with trypsin generates isomeric peptides with SEQ ID NOs:18-29, which have five cysteines. Accordingly, when such tryptic peptides have been labeled with an isotope such as $^{15}N$, the labeled peptides will all have masses that are 5 daltons greater than the same peptides that have $^{14}N$ instead. This 5 Dalton mass shift is sufficient for detection by mass spectroscopy. Moreover, very few peptides in the size range of trypsin-cleaved metallothionein peptides will exhibit a 5 Dalton shift in mass when labeled during alkylation with a stable isotope such as $^{15}N$, because very few peptides in that size range have five cysteines. Therefore, the labeled metallothionein peptides can be identified, detected and traced during various manipulations even when other peptide impurities are present.

Endopeptidase Digestion

Metallothionein isomers can be cleaved to generate unique isomeric peptides that can be more readily manipulated, detected and/or quantified. A variety of endopeptidases can be used to generate isomeric peptides of a convenient size. For example, the endopeptidase can be trypsin, Lys-C, Lys-N, Glu-C, chymotrypsin, pepsin, thermolysin, papain, Arg-C, Asp-N or chemical cleavage with cyanogen bromide.

Trypsin is an excellent choice for generating isomeric metallothionein peptides that can be simultaneously identified and quantified. Trypsin generates peptides with SEQ ID NOs: 18-29. Lys-C, another commonly used enzyme, will give identical results. Lys-N will generate a similar complement of N-terminal peptides, but the resulting peptide will lack an amino group that thus will eliminate a positive charge, which will impair the ionization potential of the Lys-N peptide. Glu-C could be used to generate a full complement of unique N-terminal peptides for all metallothioneins. However, if Glu-C is used, all metallothionein isomers may not be readily analyzed and/or quantified, or other aspects of the analytic process may need modification. Enzymatic cleavage with Arg-C or Asp-N, or chemical cleavage with cyanogen bromide would not yield peptides that can be readily analyzed and/or quantified. The process described herein may also need some modification if other proteases with broader specificity such as chymotrypsin, thermolysin, or pepsin are used. The MT-4 N-terminal peptide is not readily identified when trypsin or Glu-C is used for cleavage because of the proximity of an Arg and a Glu residue to the N-terminus. Detection of this last isoform, however, is possible with Lys-C (unique MH1+monoisotopic mass of 2536.9 m/z).

A summary of the impact of using various peptidases for cleavage of metallothionein isomers is provided in the following table.

| | Potential Utility of Enzymes for Cleavage of Some Metallothioneins | | | | |
|---|---|---|---|---|---|
| | Unique acetyl N-term peptide detection | | | SCX chromatographic | ionization |
| enzyme or chemical | MT1/2[a] | MT3 | MT4 | properties | potential |
| trypsin | yes | yes | no | weak | average |
| Lys-C | yes | yes | yes | weak | average |
| Lys-N | yes | yes | yes | weak | weak |
| Glu-C | yes[b] | no | no | strong | strong |
| Arg-C | no | no | no | | |
| Asp-N | no | no | no | | |
| CN Br | no | no | no | | |
| pepsin | no | no | no | | |
| chymotrypsin | no | no | no | | |
| thermolysin | no | no | no | | |
| proteinase K | no | no | no | | |

[a]Each MT1/2 isoform has an N-terminal peptide distinguished from all others by their mass.
[b]Glu-C digestion of MT-1H will generate an N-terminal peptide that is half the mass of all other MT1/2 peptides.

Therefore different peptidases can be used to generate metallothionein isomeric peptides that can be detected, separated and/or quantified. However, trypsin, Glu-C, Lys-C or Lys-N may be more useful.

Separation and/or Enrichment

After cleavage the metallothionein peptides can be separated by a variety of procedures. For example, the peptides can be separated and/or purified by chromatographic or electrophoretic procedures. Examples of useful processes for separation, purification and/or enrichment of metallothionein peptides include liquid chromatographic procedures such as high pressure liquid chromatography (HPLC), gel filtration, ion exchange, affinity chromatography, hydrophobic interaction chromatography, reverse phase chromatography and the like.

Unlike most peptides, which tend to be hydrophobic, metallothionein peptides are hydrophilic. For example, while most trypsin-cleaved peptides will be retained by a reversed-phase chromatography column, the hydrophilic metallothionein peptides will be only weakly retained and can be eluted before most peptide impurities. The hydrophobic peptide impurities will generally be retained by the reverse phase matrix. For example, the hydrophilic metallothionein peptides will be eluted early when an increasingly hydrophobic gradient of solvents is used for elution, while the hydrophobic peptide impurities are retained and later eluted. Thus, reverse phase chromatography can be used to enrich the concentration of metallothionein N-terminal peptides within a peptide pool.

Acetylated metallothionein N-terminal peptides also have a net charge of +1 at acidic pH, while most other tryptic peptides typically have higher charge densities. These differences can also be used to remove of impurities from a peptide pool that includes metallothionein peptides by ion exchange chromatography. For example, the more weakly retained acetylated metallothionein peptides can be eluted from a matrix of a strong cation exchange chromatography column, while the of non-metallothionein bulk peptides are retained.

Useful methods of separating the peptides from impurities (and thereby generating an enriched pool of metallothionein peptides) include Strong Cation Exchange (SCX) chromatography and/or reversed phase HPLC. For example, the peptides can be applied to the SCX column under acidic conditions and eluted by a gradient containing salt and acetonitrile. Peptide separation can be enhanced by further purification via reversed phase HLPC.

Quantification

Quantification can be by mass spectroscopic detection of the average monoisotopic peak height ratio between unlabeled and labeled peptide samples. Relative expression of metallothionein isomers can be determined by comparing the amount of unlabeled (e.g., $^{14}$N— alkylated, or light) metallothionein peptide isomers in sample with the amount of labeled (e.g., $^{15}$N-alkylated, or heavy) metallothionein peptide isomers in a sample. Alternatively, for example, two different labels can be used for different fractions (e.g., differently manipulated fractions) of a test sample for evaluating relative expression of one or more metallothionein isomers. Absolute quantification can be assessed, for example, by mixing a known amount of a labeled reference or standard peptide with a sample and determining the quantity of metallothionein isoform(s) in the sample relative to the known amount of reference peptide. Thus, both relative and absolute quantification of metallothionein isoforms can be determined.

The reference or standard peptide(s) can be one or more metallothionein peptides with a known selected sequence. Each reference or standard peptide can be synthesized, labeled (e.g., with stable isotope-labeled iodoacetamide), and re-purified via an analytical C18 column. The absolute concentration of the reference peptide(s) can be determined using elemental analysis. A known amount of labeled (e.g., $^{15}$N) reference peptide can be added as a standard to an unlabeled (or alternatively labeled) sample in which the metallothionein isomer content is to be analyzed. The unlabeled (e.g., $^{14}$N) or alternatively labeled metallothionein peptides in the sample can be detected mass spectrometry and their peak heights or areas are compared to the standard reference peak height to determine the absolute amount of unlabeled or alternatively labeled metallothionein peptides of interest in the sample. More than one reference peptide can be employed, for example, to control for peptide-specific differences in processing, detection, and quantification. For example, when quantification of MT-1E is desired, the reference peptide can be a labeled (e.g., $^{15}$N-labeled) MT-1E peptide of the same sequence as the unlabeled (e.g., $^{14}$N) or alternatively labeled MT-1E peptide that is of interest and that may be present in a test sample. Similarly, when quantification of any of the other metallothionein isoforms is of interest, the reference peptide (e.g., $^{15}$N-labeled) can be a peptide corresponding to the metallothionein isomeric peptide of interest, where the reference peptide has a known concentration and is detectable by some means (e.g., $^{15}$N-labeling).

Relative quantification of peptides in a test sample can be determined by comparing control and test samples of the same materials, where the test sample has been manipulated in some way (e.g., by induction of genes of interest, by introduction of a compound or substance that may stress cells in the test sample, etc.). Thus, the control can be a reserved aliquot of tissues or cells from which the peptides of interest are unlabeled (e.g., $^{14}$N) or labeled differently from the test sample. A test sample of the same tissues or cells is experimentally manipulated, and the concentration or amount of the alternatively labeled (e.g., $^{15}$N) peptide(s) of interest in the test sample is compared to the concentration or amount of unlabeled (e.g., $^{14}$N) or alternatively labeled control sample peptides via mass spectrometry. Thus, either of the control or test sample isomeric peptides can be labeled, or unlabeled, so long as the different peptides in each sample can be detected and distinguished.

Relative quantification is useful for simultaneously comparing fold inductions of metallothionein isoforms from two directly comparable samples. Absolute quantification is beneficial when, for example, absolute numbers are needed for disease diagnostic purposes or when a suitable control sample is not available.

General Description of Experimental Results

For example, a human prostate epithelium derived cell line (RWPE-1) was used in an experiment. The cell line had been treated with or without 75 µM Zn. When these cells are treated with 75 µM Zn there is high induction of metallothioneins. These cells were grown, harvested, and cytosolic protein was extracted. The cytosolic protein was denatured with urea, reduced with TCEP, alkylated with iodoacetamide, and digested with trypsin. The resulting cytosolic peptides were then separated and enriched through the methods described herein. This provided adequate enrichment and allowed for identification of the different metallothionein isomers using a MALDI-TOF/TOF mass spectrometer.

This technique was then applied to the human kidney epithelium cell line (HK-215 MT-3) where an MT-3 expression cassette has been stably transfected into the cell line. Stock cultures of the HK-2 cell line were grown in 75 cm$^2$ T-flasks using a serum-free growth formulation. The growth formulation consisted of a 1:1 mixture of Dulbecco's modified Eagles' medium (DMEM) and Ham's F-12 growth medium supplemented with selenium (5 ng/ml), insulin (5 µg/ml), transferrin (5 µg/ml), hydrocortisone (36 ng/ml), triiodothyronine (4 pg/ml) and epidermal growth factor (10 ng/ml). Cultures were incubated at 37° C. in a humidified atmosphere containing 5% $CO_2$. The cells were fed fresh growth medium every other day and were subcultured at confluence (normally 3-6 days post subculture) using trypsin-EDTA (0.05%-0.02%). Cells were sub-cultured at a 1:4 ratio, and allowed to reach confluence (6-9 days following sub-culture), then used in experiments.

The HK2-MT3 stably transfected cells were allowed to reach confluence with doming After cells domed they were either exposed to 9 µM $CdCl_2$ containing media (induced) or fed fresh media without $CdCl_2$ (controls). Cells that were treated with $CdCl_2$ were exposed for 3 days, with feeding every other day, and harvested. The controls were fed fresh media without $CdCl_2$ for 3 days then harvested. Cell pellets were either frozen immediately at −80° C. or used for analysis.

For the isolation of protein, the cell monolayers from two T-75 flasks were washed three times with phosphate-buffered saline (PBS), detached from the growth surface by scrapping, and collected as a pellet by centrifugation at 2000 rpm for 5 min at 4° C. The cell pellet was resuspended in 0.6 mL of hypotonic buffer (10 mM Tris pH 8.0, 1.5 mM $MgCl_2$, 10 mM KCl, 1 mM DTT, and 0.6 µl protease inhibitor cocktail). The cells were then passed through a 25 gauge×⅝ inch needle to disrupt membranes. The nuclei were pelleted by centrifugation (800 g for 10 min at 4° C.) and the supernatant was collected followed by ultracentrifugation on a Beckman® table-top ultracentrifuge (TLA100.3, 100,000 g, 30 min at 4° C.) to remove membranes. The supernatant was then collected to yield the cytosolic protein extract. A BioRad® protein assay was then performed on the samples to quantify the amount of protein. The samples were stored at −80° C. until further use.

Approximately 300 μg control lysate and 300 μg cadmium-induced lysate were incubated with 3.5 mM EDTA. Samples were then denatured with 8 M urea reduced with 5 mM TCEP for 1 hour at room temperature. The samples were then alkylated with 28 mM of either $^{14}$N-iodoacetamide (control, 'light') or $^{15}$N-iodoacetamide (test, 'heavy') at room temperature in the dark for 1 hr and quenched with ~6 mM TCEP for 10 minutes. Thus, the cadmium-induced proteins were 'heavy' labeled, while the control proteins were unlabeled or 'light.'

The control and cadmium-induced tubes were then desalted with a gel filtration column to get rid of excess alkylating agent. Control and cadmium-induced proteins were then mixed together into a single tube. The samples were incubated with trypsin (1% w/w) overnight at 37° C. After incubation, 0.1% formic acid was added to stop tryptic activity and to protonate the peptides. The samples were then run through a CEREX® octadecyl C18 heavy load solid phase extraction column to remove salts and concentrate the peptides.

Peptides were then fractionated through a 2.1 mm×25 cm poly LC polysulfoethyl A SCX column over a 70 min. gradient while collecting a fraction every 7 minutes (buffer A: 0.02% formic & 20% ACN, buffer B: 0.1% formic; 1 M NaCl; 10% ACN). The metallothionein fraction was then treated with 8M HCl containing 0.5M dimethyl sulfide (DMS) for 30 minutes to reduce methionine sulfoxides back to methionine. Approximately 3 μg of the metallothionein fraction was injected into an ABI SCIEX Tempo™ LC MALDI nanoHPLC system with an integrated spotter and was fractionated through a self-packed column (MICHROM Bioresources Magic C18AQ 200 Å pore size, 5 μM diameter particles, and 100 μm×10 cm in length) over 250 spots. The column was equilibrated with 97% Buffer A (0.1% formic acid, 2% acetonitrile) and 3% Buffer B (0.1% formic acid, 98% acetonitrile) at a flow rate of 0.8 μl/min and peptides were fractionated with a 70 min linear gradient of 3% Buffer B/97% Buffer A to 20% Buffer B/80% Buffer A. Fractions were spotted every 0.18 seconds onto a MALDI target plate with post-column mixing of an equal volume of 10 mg/mL α-cyano-4-hydroxycinnamic acid (CHCA) in 75% acetonitrile, 0.1% formic acid. The column was recycled with 70% Buffer B/30% Buffer A for 5 minutes and then re-equilibrated with 3% pump B for 10 minutes.

Samples were analyzed by MS and MS/MS using an ABI 4800 MALDITOF/TOF mass spectrometer. Metallothionein peptides were identified by searching spectra against the human UniProt database and confirmed by manual analysis. Relative metallothionein quantification was achieved by taking average monoisotopic peak intensities of the unique acetylated N-terminal Cd-induced heavy ($^{15}$N-labeled) to light (control $^{14}$N-labeled) peptides for each metallothionein isoform.

Absolute quantification was achieved by taking the average monoisotopic peak intensity ratio of the unique acetylated N-terminal heavy (absolute standard of known concentration) to light (cadmium-induced) peptide for each metallothionein isoform being analyzed. For example, for each metallothionein isoform, 5 spots from the MALDI target plate were analyzed by mass spectroscopy and average monoisotopic peak intensities were generated for control ($^{14}$N-labeled, 'light') and test ($^{15}$N-labeled, 'heavy') peptides. The mass of each of the heavy peptides was corrected for light isotopic label contribution (which took into account the % control peptides labeled and also the isotopic purity of the iodoacetamide).

The methods described herein can identify and quantify small amounts of metallothionein protein isomers. For example, the methods can detect metallothionein isomers when they are present at only about 0.05 ng to 20 ng per ng total protein in a test sample. In some cases, the methods can detect metallothionein isomers when they are present at only about 0.05 ng to 10 ng per μg total protein in a test sample, or at only about 0.05 ng to 5 ng per μg total protein in a test sample. For example, the methods described herein can detect as little as 0.05 ng to 2 ng metallothionein protein isomer per μg total protein in a test sample.

Metallothioneins

Metallothioneins (MTs) are a low-molecular-weight (6-7 kDa) metal-binding family of proteins that have a high content of conserved cysteine residues. For example, metallothioneins have a total of 20-21 cysteines out of a total of 60-70 amino acids. This high cysteine content allows them to bind transition heavy metals, such as zinc (Zn), cadmium (Cd), and copper (Cu) with high affinity.

Metallothionein gene expression is induced by a high variety of stimuli, as metal exposure, oxidative stress, glucocorticoids, and other stressors. The level of the response to these inducers depends on the metallothionein gene. The promoters of metallothionein genes can have specific sequences for regulation of metallothionein mRNA expression including metal response elements (MRE), glucocorticoid response elements (GRE), and anti-oxidant response elements (ARE).

A number of metallothionein isoforms are expressed in human tissues. These isoforms share 70 to 90% amino acid sequence identity. For example, the following metallothionein isomers are found in various human tissues in at least small amounts: metallothionein-1A, metallothionein-1B, metallothionein-1E, metallothionein-1F, metallothionein-1G1, metallothionein-1G2, metallothionein-1H, metallothionein-1L, metallothionein-1M, metallothionein-1X, metallothionein-2, metallothionein-3, and metallothionein-4.

Sequences are available for various metallothionein proteins and nucleic acids, for example, in the sequence database maintained by the National Center for Biotechnology Information (see website at www.ncbi.nlm.nih.gov/).

One example of a human metallothionein-1A (MT-1A) amino acid sequence is available as accession number NP_005937.2 (GI:71274113), provided below as SEQ ID NO:1.

```
 1 MDPNCSCATG GSCTCTGSCK CKECKCTSCK KSCCSCCPMS
41 CAKCAQGCIC KGASEKCSCC A
```

Another example of a human metallothionein-1A (MT-1A) amino acid sequence is available as accession number P04731 (e.g., P04731.2, GI:269849625) from the NCBI database.

An example of a human metallothionein-1B (MT-1B) sequence is available as accession number NP_005938.1 (GI:27414495) and is provided below as amino acid sequence SEQ ID NO:2.

```
 1 MDPNCSCTTG GSCACAGSCK CKECKCTSCK KCCCSCCPVG
41 CAKCAQGCVC KGSSEKCRCC A
```

Another example of a human metallothionein-1B (MT-1B) amino acid sequence is available as accession number P07438 (e.g., P07438.1, GI:127367) from the NCBI database.

An example of a human metallothionein-1E (MT-1E) sequence is available as accession number NP_783316.2 (GI:83367075) and is provided below as amino acid sequence SEQ ID NO:3.

```
 1 MDPNCSCATG GSCTCAGSCK CKECKCTSCK KSCCSCCPVG
41 CAKCAQGCVC KGASEKCSCC A
```

Another example of a human metallothionein-1E (MT-1E) amino acid sequence is available as accession number P04732 (e.g., P04732.1, GI:127370) from the NCBI database.

An example of a human metallothionein-1F (MT-1F) sequence is available as accession number NP_005940.1 (GI:28866947) and is provided below as amino acid sequence SEQ ID NO:4.

```
 1 MDPNCSCAAG VSCTCAGSCK CKECKCTSCK KSCCSCCPVG
41 CSKCAQGCVC KGASEKCSCC D
```

Another example of a human metallothionein-1F (MT-1F) amino acid sequence is available as accession number P04733 (e.g., P04733.1, GI:127371) from the NCBI database.

An example of a human metallothionein-1G1 (MT-1G1; also referred to as metallothionein 1G, isoform CRA_b) sequence is available as accession number EAW82883.1 (GI:119603289) and is provided below as amino acid sequence SEQ ID NO:5.

```
 1 MDPNCSCAAA GVSCTCASSC KCKECKCTSC KKSCCSCCPV
41 GCAKCAQGCI CKGASEKCSC CA
```

Another example of a human metallothionein-1G1 (MT-1G1) amino acid sequence is available as accession number P13640 (e.g., P13640.2, GI:90109444) from the NCBI database.

An example of a human metallothionein-1G2 (MT-1G2; also referred to as metallothionein 1G, isoform CRA_a) sequence is available as accession number EAW82882.1 (GI:119603288) and is provided below as amino acid sequence SEQ ID NO:6.

```
 1 MDPNCSCAAG VSCTCASSCK CKECKCTSCK KSCCSCCPVG
41 CAKCAQGCIC KGASEKCSCC A
```

Another example of a human metallothionein-1G2 (MT-1G2) amino acid sequence is available as accession number NP_005941.1 (GI:10835230) from the NCBI database.

An example of a human metallothionein-1H (MT-1H) sequence is available as accession number EAW82884.1 (GI:119603290) and is provided below as amino acid sequence SEQ ID NO:7.

```
 1 MDPNCSCEAG GSCACAGSCK CKKCKCTSCK KSCCSCCPLG
41 CAKCAQGCIC KGASEKCSCC A
```

Another example of a human metallothionein-1H (MT-1H) amino acid sequence is available as accession number P80294 (e.g., P80294.1, GI:462634) from the NCBI database.

An example of a human metallothionein-1L (MT-1L) sequence is available as accession number Q93083.1 (GI:2497864) and is provided below as amino acid sequence SEQ ID NO:8.

```
 1 MDPNCSCATG GSCSCASSCK CKECKCTSCK KSCCSCCPMG
41 CAKCAQGCVC KGASEKCSCC A
```

Another example of a human metallothionein-1L (MT-1L) amino acid sequence is available as accession number Q93083 (e.g., Q93083.1, GI:2497864) from the NCBI database.

An example of a human metallothionein-1M (MT-1M) sequence is available as accession number NP_789846.1 (GI:28866966) and is provided below as amino acid sequence SEQ ID NO:9.

```
 1 MDPNCSCTTG VSCACTGSCK CKECKCTSCK KSCCSCCPVG
41 CAKCAHGCVC KGTLENCSCC A
```

Another example of a human metallothionein-1M (MT-1M) amino acid sequence is available as accession number Q8N339 (e.g., Q8N339.2, GI:88913543) from the NCBI database.

An example of a human metallothionein-1X (MT-1X) sequence is available as accession number NP_005943.1 (GI:10835232) and is provided below as amino acid sequence SEQ ID NO:10.

```
 1 MDPNCSCSPV GSCACAGSCK CKECKCTSCK KSCCSCCPVG
41 CAKCAQGCIC KGTSDKCSCC A
```

Another example of a human metallothionein-1X (MT-1X) amino acid sequence is available as accession number P80297 (e.g., P80297.1, GI:462637) from the NCBI database.

An example of a human metallothionein-2 (MT-2) sequence is available as accession number NP_005944.1 (GI:5174764) and is provided below as amino acid sequence SEQ ID NO:11.

```
 1 MDPNCSCAAG DSCTCAGSCK CKECKCTSCK KSCCSCCPVG
41 CAKCAQGCIC KGASDKCSCC A
```

Another example of a human metallothionein-2 (MT-2) amino acid sequence is available as accession number P02795 (e.g., P02795.1, GI:127397) from the NCBI database.

An example of a human metallothionein-3 (MT-3) sequence is available as accession number NP_005945.1 (GI:5174762) and is provided below as amino acid sequence SEQ ID NO:12.

```
 1 MDPETCPCPS GGSCTCADSC KCEGCKCTSC KKSCCSCCPA
41 ECEKCAKDCV CKGGEAAEAE AEKCSCCQ
```

Another example of a human metallothionein-3 (MT-3) amino acid sequence is available as accession number P25713 (e.g., P25713.1, GI:127404) from the NCBI database.

An example of a human metallothionein-4 (MT-4) sequence is available as accession number NP_116324.1 (GI:14269578) and is provided below as amino acid sequence SEQ ID NO:13.

```
 1 MDPRECVCMS GGICMCGDNC KCTTCNCKTC RKSCCPCCPP
41 GCAKCARGCI CKGGSDKCSC CP
```

Disease Detection

The expression of each metallothionein isoform is differentially regulated by various physiological/disease conditions (e.g. cellular stress, cancer, etc.) and in response to environmental factors (e.g., exposure to toxins such as Cd, Hg). Therefore, analyses of specific metallothionein isoforms may serve as biomarkers to detect these conditions. Metallothionein isoforms can be important for early detection, tumor sub-typing, diagnosis, prognosis and decision making in therapeutic strategies. Methods and kits described herein can therefore be used to detect and monitor disease.

For example, MT-3 is normally expressed only in the brain and kidney (Hoey et al., Toxicology Letters 92:149-160, 1997), while most of the other metallothionein isoforms are ubiquitously expressed. Identifying and quantifying the expression level of MT-3 in the urine, for example, can be prognostic for genitourinary disease because kidney damage can cause cellular proteins from that tissue, including MT-3, to be released into the urine. Similarly, although normal bladder tissues do not normally express MT-3, expression of MT-3 is induced in bladder cancer (Sens et al., Environmental Health Perspectives 5:413-418, 2000). Bladder cancer cells also overexpress MT-1X (Somji et al., Cancer Detect Prev. 25:62-75 2001). Advanced prostate cancer cells exhibit reduced MT-1X expression (Garrett et al Prostate 43:125-135, 10 2000). Hence, accurate quantification of the amounts of metallothionein isomers in tissue and biological fluid samples, as described herein, can be used for diagnosis of various types of cancer.

Metallothioneins are known to be an important component in the cells for protection against and recovery from environmental insult, especially those associated with heavy metals. Expression of metallothionein isoforms is also altered in many types of cancers and can be related to poor patient prognosis.

A non-exhaustive sampling of other metallothionein/cancer correlations indicate that the following metallothionein isomers are correlated with the following types of cancer.

Only MT-1E and MT-2A are found in well-differentiated HK1 nasopharyngeal carcinoma (NPC) cells (Tan et al., Oncol Rep 13: 127-131, 2005).

Expression of MT-1E, 1F, 1G, 1H, and 1M has been found to be abolished during the transition from normal mucosa to colorectal tumor, while MT-1X and MT-2A were less down-regulated in the colorectal tumor tissues (Arriga et al., Human Pathology, 43:197, 2012).

MT-1E, 1G, 1X and MT2A are down-regulated in papillary thyroid carcinoma (Ferrario et al., Lab Invest 88:474-481).

MT-2A and all MT-1 isoforms are significantly reduced in hepatocellular carcinomas (Dhatta et al., Cancer Res 67:2736-2746, 2007).

Detectable levels of MT-1A and 1H transcripts are found in breast cancer cell lines and tissue samples but MT-1B and MT-4 are absent.

MT-1E, 1F, 1X and 2A are significantly upregulated in breast cancer (Tai et al., Am J Pathol 163: 2009-19, 2003; Jin et al, Carcinogenesis, 23: 81-6, 2002).

MT-1E is overexpressed in ER-negative invasive ductal cancers (Erlander et al., WO2009108215) or predictive of responsiveness to the IGF-1R kinase inhibitor therapeutics (Eckhardt et al., US2010020665).

MT-3 is overexpressed in ductal carcinoma in situ and associated with poor prognosis in breast cancer (Sens et al., Am 5 J Pathol 159: 21-6, 2001).

MT-1F and MT-2A are associated with higher tumor grading (Jin et al., Breast Cancer Re Treat, 66: 265-72, 2001; Jin et al., Carcinogenesis, 23: 81-6, 2002).

Also by way of example, metallothioneins associate with the heavy metal pollutant Cd in the renal cortex and exposure to Cd causes induction of metallothionein expression. Studies have shown that chronic exposure to Cd is associated with many health problems including an increased risk of lung cancer and renal diseases with smokers having a higher risk of renal cancer than nonsmokers. The expression of each isoform is differentially regulated by various physiological/disease conditions (e.g. cellular stress, cancer, etc.) and environmental factors (e.g., exposure to toxins such as Cd, Hg).

Therefore, different metallothionein isoforms can serve as biomarkers for detection of different diseases and conditions. For example, altered expression of metallothioneins can be diagnostic of certain cancers such as cancers of the breast, colon, kidney, liver, skin (melanoma), lung, nasopharynx, ovary, prostate, mouth, salivary gland, testes, thyroid and urinary bladder. The cancer can be an invasive or metastatic cancer. The cancer can also be a tumor that is prone to angiogenesis. Examples of cancers that can be detected by the methods described herein include solid tumors and cancers as well as cancers associated with particular tissues, including breast cancer, colon cancer, lung cancer, prostate cancer, ovarian cancer, cancer of the central nervous system, carcinomas, leukemias, lymphomas, melanomas, fibrosarcomas, neuroblastoma, and the like. The cancer can, for example, be autoimmune deficiency syndrome-associated Kaposi's sarcoma, cancer of the adrenal cortex, pheochromocytoma, cancer of the cervix, cancer of the endometrium, cancer of the esophagus, cancer of the head and neck, cancer of the liver, cancer of the pancreas, cancer of the prostate, cancer of the thymus, carcinoid tumors, chronic lymphocytic leukemia, Ewing's sarcoma, gestational trophoblastic tumors, hepatoblastoma, multiple myeloma, non-small cell lung cancer, retinoblastoma, or tumors in the ovaries. Especially in cancer, metallothionein isoforms may be important for early detection, tumor sub-typing, diagnosis, prognosis and decision making in therapeutic strategies.

The methods and kits described herein can also be used to detect and/or monitor toxin exposure, or the development of a reaction or disease relating to toxin exposure. Such toxins can include one or more of benzene, toluene, ethylbenzene, xylene, polyaromatic hydrocarbons, polychlorinated biphenols and heavy metals such as copper, lead, mercury, indium, vanadium, or cadmium or other environmental pollutant or mixture thereof.

Therefore, the invention also includes a method or kit for detecting or monitoring a disease or disorder in a mammalian subject that includes quantifying an amount of at least one metallothionein isomer in a test sample obtained from the subject. The quantity of a selected metallothionein isomer in a test sample can be compared to the quantity of the same type of metallothionein isomer in a control sample (e.g., of healthy tissue or biological fluid). When the quantities of one or more metallothionein isomers differ in a test sample compared to the control, the subject can be informed that he or she may have a potential disease. Appropriate treatment can be initiated.

Disease Treatment

One aspect of the invention is a method of treating cancer in a mammal when disease is detected. For example, cancers can be treated by administering to a subject an effective amount of a chemotherapeutic agent. According to the invention, treatment of cancer can involve killing tumor cells, reducing the growth of tumor cells and reducing the growth or function of tumor stromal cells in a mammal Treatment of cancer can also involve promoting apoptosis of cancer cells. Treatment of cancer can also involve inhibiting angiogenesis of a tumor in a mammal.

For example, when cancer is detected in a subject, the subject can be treated with an agent such as a cytotoxin, photosensitizing agent or a chemotherapeutic agent. These agents include, but are not limited to, folate antagonists, pyrimidine antimetabolites, purine antimetabolites, 5-aminolevulinic acid, alkylating agents, platinum anti-tumor agents, anthracyclines, DNA intercalators, epipodophyllotoxins, DNA topoisomerases, microtubule-targeting agents, vinca alkaloids, taxanes, and epothilones. Further information can be found in Bast et al., CANCER MEDICINE, edition 5, which is available free as a digital book. See website at ncbi.nlm.nih.gov/books/bv.fcgi?call=bv View..ShowTOC&rid=cmed. TOC&depth=2.

Folic acid antagonists are cytotoxic drugs used as antineoplastic, antimicrobial, anti-inflammatory, and immune-suppressive agents. While several folate antagonists have been developed, and several are now in clinical trial, methotrexate (MTX) is the antifolate with the most extensive history and widest spectrum of use. MTX is an essential drug in the chemotherapy regimens used to treat patients with acute lymphoblastic leukemia, lymphoma, osteosarcoma, breast cancer, choriocarcinoma, central nervous system cancers, and head and neck cancer, as well as being an important agent in the therapy of patients with nonmalignant diseases, such as rheumatoid arthritis, psoriasis, and graft-versus-host disease.

Pyrimidine antimetabolites include fluorouracil, cytosine arabinoside, 5-azacytidine, and 2',2'-difluoro-2'-deoxycytidine. Purine antimetabolites include 6-mercatopurine, thioguanine, allopurinol (4-hydroxypyrazolo-3,4-d-pyrimidine), deoxycoformycin (pentostatin), 2-fluoroadenosine arabinoside (fludarabine; 9-β-d-arabinofuranosyl-2-fluoradenine), and 2-chlorodeoxyadenosine (Cl-dAdo, cladribine). In addition to purine and pyrimidine analogues, other agents have been developed that inhibit biosynthetic reactions leading to the ultimate nucleic acid precursors. These include phosphonacetyl-L-aspartic acid (PALA), brequinar, acivicin, and hydroxyurea.

Alkylating agents and the platinum anti-tumor compounds form strong chemical bonds with electron-rich atoms (nucleophiles), such as sulfur in proteins and nitrogen in DNA. Although these compounds react with many biologic molecules, the primary cytotoxic actions of both classes of agents appear to be the inhibition of DNA replication and cell division produced by their reactions with DNA. However, the chemical differences between these two classes of agents produce significant differences in their anti-tumor and toxic effects. The most frequently used alkylating agents are the nitrogen mustards. Although thousands of nitrogen mustards have been synthesized and tested, only five are commonly used in cancer therapy today. These are mechlorethamine (the original "nitrogen mustard"), cyclophosphamide, ifosfamide, melphalan, and chlorambucil. Closely related to the nitrogen mustards are the aziridines, which are represented in current therapy by thiotepa, mitomycin C, and diaziquone (AZQ). Thiotepa (triethylene thiophosphoramide) has been used in the treatment of carcinomas of the ovary and breast and for the intrathecal therapy of meningeal carcinomatosis. The alkyl alkane sulfonate, busulfan, was one of the earliest alkylating agents. This compound is one of the few currently used agents that clearly alkylate through an SN2 reaction. Hepsulfam, an alkyl sulfamate analogue of busulfan with a wider range of anti-tumor activity in preclinical studies, has been evaluated in clinical trials but thus far has demonstrated no superiority to busulfan. Busulfan has a most interesting, but poorly understood, selective toxicity for early myeloid precursors. This selective effect is probably responsible for its activity against chronic myelocytic leukemia (CML).

Photosensitizing agents induce cytotoxic effects on cells and tissues. Upon exposure to light the photosensitizing compound may become toxic or may release toxic substances such as singlet oxygen or other oxidizing radicals that are damaging to cellular material or biomolecules, including the membranes of cells and cell structures, and such cellular or membrane damage can eventually kill the cells. A range of photosensitizing agents can be used, including psoralens, porphyrins, chlorines, aluminum phthalocyanine with 2 to 4 sulfonate groups on phenyl rings (e.g., $AlPcS_{2a}$ or $AlPcS_4$) and phthalocyanins. Such drugs become toxic when exposed to light. In one embodiment, the photosensitizing agent is an amino acid called 5-aminolevulinic acid, which is converted to protoporphyrin IX, a fluorescent photosensitizer. 5-Aminolevulinic acid has been approved for treating skin and esophagus cancers and is in clinical trial for brain tumor detection and therapy. Light therapy is used to activate the photosensitizing agent. For example, laser treatment can be used. Alternatively, light rods can be inserted into the flesh.

Topoisomerase poisons are believed to bind to DNA, the topoisomerase, or either molecule at or near the region of the enzyme involved in the formation of the DNA protein covalent linkage. Many topoisomerase poisons, such as the anthracyclines and actinomycin D, are relatively planar hydrophobic compounds that bind to DNA with high affinity by intercalation, which involves stacking of the compound between adjacent base pairs. Anthracyclines intercalate into double-stranded DNA and produce structural changes that interfere with DNA and RNA syntheses. Several of the clinically relevant anthracyclines include doxorubicin, daunorubicin, epirubicin, and idarabicin.

Non-intercalating topoisomerase-targeting drugs include epipodophyllotoxins such as etoposide and teniposide. Etoposide is approved in the United States for the treatment of testicular and small cell lung carcinomas. Etoposide phosphate is more water soluble than etoposide and is rapidly converted to etoposide in vivo. Other non-intercalating topoisomerase-targeting drugs include topotecan and irinotecan.

Unique classes of natural product anticancer drugs have been derived from plants. As distinct from those agents derived from bacterial and fungal sources, the plant products, represented by the Vinca and Colchicum alkaloids, as well as other plant-derived products such as paclitaxel (Taxol) and podophyllotoxin, do not target DNA. Rather, they either interact with intact microtubules, integral components of the cytoskeleton of the cell, or with their subunit molecules, the tubulins. Clinically useful plant products that target microtubules include the Vinca alkaloids, primarily vinblastine (VLB), vincristine (VCR), vinorelbine (Navelbine, VRLB), and a newer Vinca alkaloid, vinflunine (VFL; 20',20'-difluoro-3',4'-dihydrovinorelbine), as well as the two taxanes, paclitaxel and docetaxel (Taxotere).

Hence, examples of drugs that can be used for treatment include, but are not limited to, aldesleukin, 5-aminolevulinic acid, asparaginase, bleomycin sulfate, camptothecin, carboplatin, carmustine, cisplatin, cladribine, cyclophosphamide (lyophilized), cyclophosphamide (non-lyophilized), cytarabine (lyophilized powder), dacarbazine, dactinomycin, daunorubicin, diethyistilbestrol, doxorubicin (doxorubicin, 4'-epidoxorubicin, 4- or 4'-deoxydoxorubicin), epoetin alfa, esperamycin, etidronate, etoposide, N,N-bis(2-chloroethyl)-hydroxyaniline, 4-hydroxycyclophosphamide, fenoterol, filgrastim, floxuridine, fludarabine phosphate, fluorocytidine, fluorouracil, fluorouridine, goserelin, granisetron hydrochloride, idarubicin, ifosfamide, interferon alpha-2a, interferon alpha-2b, leucovorin calcium, leuprolide, levamisole, mechiorethamine, medroxyprogesterone, melphalan, methotrexate, mitomycin, mitoxantrone, muscarine, octreotide, ondansetron hydrochloride, oxyphenbutazone, paclitaxel, pamidronate, pegaspargase, plicamycin, salicylic acid, salbutamol, sargramostim, streptozocin, taxol, terbutaline, terfenadine, thiotepa, teniposide, vinblastine, vindesine and vincristine. Other drugs and toxic effector molecules for use in the present invention are disclosed, for example, in WO 98/13059; Payne, 2003; US 2002/0147138 and other references available to one of skill in the art.

The methods and kits described herein can also be used to detect and/or monitor toxin exposure, or the development of a reaction or disease relating to toxin exposure. Such toxins can include one or more of benzene, toluene, ethylbenzene, xylene, polyaromatic hydrocarbons, polychlorinated biphenols and heavy metals such as copper, lead, mercury or cadmium or other environmental pollutant or mixture thereof. The methods and kits can therefore be companion diagnostics for diseases such as those recited herein. By use of the methods and kits described herein, disease development and progression can be avoided by early detection of toxin exposure and avoidance of such exposure. Moreover, treatment of toxic exposure or reaction to toxins can be iniatiated. For example, when heavy metal exposure or reaction to heavy metal exposure is detected in a test sample, the subject from whom the test sample was obtained can be treated. Treatments can include heavy metal chelation, antioxidant administration, reperfusion, dietary changes, and the like. One example of a therapeutic agent that can be administered to such a subject is 2,7,9,-tricarboxypyrroloquinoline quinone. The methods and kits described herein can also be used as a companion diagnostic to detect and/or monitor metal toxicity induced by platinum-based chemotherapies.

Kits

In other aspects, the invention is drawn to kits comprising one or more components, such as one or more reagents for detecting and quantifying metallothionein protein isomers, and instructions for using the kit and its components.

The kit can include components for processing tissues and cells in the methods described herein, such as tissue or cell stabilizing agents, protease inhibitors, protein denaturing agents (or a mixture of agents for denaturing proteins), reducing agents, buffers, diluents, small spin columns for removal of undesired materials from test samples, or similar components, including any of the reagents described herein.

The kit can also include components for preparing the proteins in a test sample for analysis such as reducing agents, alkylating agents (e.g. iodoacetamide or iodoacetic acid), labeling agents (e.g., $^{15}$N-labeled iodoacetamide or $^{15}$N-labeled iodoacetic acid), proteases (e.g., trypsin, Lys-C, Lys-N, Glu-C, chymotrypsin, pepsin, thermolysin, papain, Arg-C, Asp-N or chemical cleavage agents such as cyanogen bromide), small spin columns for removal of undesired impurities, small spin columns for enrichment of metallothionein proteins or peptides, buffers for separation and/or enrichment of metallothionein peptides (e.g., buffers for ion exchange chromatography or reversed phase chromatography), chromatography matrices or chromatography columns (e.g., those for ion exchange chromatography or reversed phase chromatography), or similar components, including any of the reagents described herein.

The kit can also include reference or standard peptides, such as any of metallothionein isomeric peptides described herein. The reference or standard peptides can be labeled (e.g., with a stable isotope such as $^{15}$N, $^{13}$C or deuterium), or be unlabeled. The reference or standard peptides can be provided in solution or as a dry powder (e.g., a lyophilized powder). The reference or standard peptides are provided at a specified concentration (e.g., in solution) or as a specified amount (e.g., in dry form).

Instructions provided with the kit can provide information for performing the methods described herein, including steps involving test sample isolation, protein denaturation, reduction, alkylation, labeling, protease digestion, peptide separation, metallothionein peptide enrichment, quantitative mass spectrometry, use of reference or standard peptides, and combinations of such steps. Instructions provided with the kit can provide information for identifying or distinguishing one or more metallothionein protein or peptide isomers from another. The instructions can provide information for identifying or distinguishing each metallothionein protein or peptide isomer from another or from all others. For example, the instructions can provide specific mass spectroscopic data for one or more (or all) metallothionein isomeric peptide (e.g., as described in the Examples and figures provided herein).

Instructions provided with the kit can also provide information for diagnosing disease, including any of the diseases recited herein. For example, instructions provided with the kit can provide information for identifying diagnosing cancer or heavy metal toxicity when one or more metallothionein protein isomers are detected in a test sample, or when a specified amount or concentration of one or more protein metallothionein protein isomers is detected in a test sample. For example, the kit can serve as a companion diagnostic for detection or monitoring of diseases such as cancer, toxic exposure, heavy metal poisoning, or the development of metal toxicity induced by platinum-based chemotherapies.

The present invention is further illustrated by the following examples, which should not be construed as limiting in any way. The contents of all cited references (including literature references, issued patents, published patent applications as cited throughout this application) are hereby expressly incorporated by reference.

EXAMPLE 1

Materials and Methods

This Example describes some of the materials and methods used in the development of the invention.

Materials and Reagents—$^{15}$N-iodoacetamide was from Sigma-Aldrich (St. Louis, Mo.). Isoform-specific N-terminal acetylated metallothionein peptides were synthesized by Elim Biopharmaceuticals (Hayward, Calif.).

Cell Culture—The human kidney epithelial HK-2 cells containing the stably transfected human metallothionein-3 were grown as described previously (Kim et al., Kidney Int. 61, 464-472 (2002); Somji et al., Toxicol. Sci. 80, 358-366 (2004)). The cells were allowed to reach confluence with doming After cells domed they were maintained for three days in the presence or absence of 9 uM $CdCl_2$ to induce the expression of metallothioneins. All data from these cells represents biological replicates done in triplicates. Cell monolayers from two T-75 flasks were washed twice with phosphate-buffered saline (PBS), detached by scraping, and pelleted by centrifugation at 197×g for 5 min at 4° C. The five breast cell lines (MCF-10A, MCF-7, T-47D, Hs578T, MDA-MB-231) were obtained from the American Type Culture Collection. The MCF-10A cells were grown in a 1:1 mixture of Ham's F-12 medium and DMEM supplemented with 5% (v/v) fetal calf serum, 10 μg/ml insulin, 0.5 μg/ml hydrocortisone, 20 ng/ml epidermal growth factor, and 0.1 μg/ml cholera toxin. The MCF-7, T-47D, Hs578T, and MDA-MB-231 cells were grown in DMEM supplemented with 5% (v/v) fetal calf serum. The cells were fed fresh growth medium every 3 days, and at confluence (normally 6-12 days post subculture), the cells were subcultured at a 1:4 ratio using trypsin-EDTA (0.25%, 1 mM). Cell pellets were either stored at −80° C. or used immediately.

Cytosol Preparation—Cells were resuspended in 0.5 mL of hypotonic buffer (10 mM Tris pH 8.0, 1.5 mM $MgCl_2$, 10 mM KCl, 1 mM DTT, and 0.5 μL protease inhibitor cocktail (Sigma-Aldrich). The cells were then passed through a 25 gauge, ⅝ inch needle three times to disrupt membranes. The nuclei were pelleted by centrifugation (800×g for 10 min at 4° C.) and the supernatant was further clarified by centrifugation at 100,000×g, 30 min at 4° C. Total protein was determined by the Bio-Rad Protein Assay (Bio-Rad, Hercules, Calif.). Typical yields of 0.5 mL cytosol per two T-75 flasks was 3.0-3.5 mg/ml. Cytosols were stored at −80° C.

Reduction and Alkylation of Cytosols—300 μg control or Cd-induced cytosol (~100 μl) was incubated with 3.5 mM EDTA. Samples were then denatured with 8 M urea then reduced with 5 mM dithiothreitol (DTT) or Tris(2-carboxyethyl)phosphine (TCEP) in 100 mM Tris pH 8.0 for 1 hour at room temperature in a final volume of ~190 μl. Proteins were then alkylated at room temperature in the dark for 1 hour by the addition of ~27 μl of 200 mM $^{14}$N- or $^{15}$N-iodoacetamide to a final concentration of 28 mM. Urea and excess alkylating agent were removed from the cytosols by passing them through ~1 ml of Bio Gel P-6 in micro Bio-Spin chromatography columns (Bio-Rad Laboratories, Hercules, Calif.) equilibrated with 100 mM Tris pH 8.0.

Preparation of $^{15}$N-labeled Peptide Standards—The purity of the seven metallothionein peptides as received from the manufacturer ranged from 11 to 90% even though >95% purity was requested. This was primarily because of the difficulty of synthesis related to the high cysteine content and peptide-specific sequences. Thirty μg of each peptide was reduced with 5 mM DTT or 5 mM TCEP in 100 mM Tris pH 8.0 for 1 hour at room temperature in a final volume of 31.5 μL. The reduced peptides were then alkylated with 28 mM $^{15}$N-iodoacetamide for 1 hour in the dark at room temperature. The $^{15}$N-labeled peptides were then purified by reversed-phase chromatography using a narrow-bore 2.1× 150 mm Zorbax 300SB-C18, 5-μm bead-size column (Agilent Technologies, Santa Clara, Calif.) on a Shimadzu 10-AVP HPLC (Shimadzu, Kyoto, Japan). Peptides were separated with a linear 35 min gradient using 97% Buffer A (0.1% formic acid, 2% acetonitrile) to 38% Buffer B (0.1% formic acid, 98% acetonitrile) at 0.3 ml/min. Peptides were detected by absorbance at 214 nm. The peak corresponding to the peptide with the correct mass as determined by mass spectrometry was collected, dried and reconstituted in mass spectroscopy grade $H_2O$. All $^{15}$N-labeled peptides were at least 95% pure as assessed by reverse phase HPLC. Peptide concentration was determined using area under the curve analysis at 214 nm based on the absorbance of a known amount of metallothionein peptide for which the peptide concentration using elemental analysis was provided by the manufacturer represented a product of >95% purity. Aliquots of the purified $^{15}$N absolute metallothionein standard peptides were stored at −80° C. A reference mixture containing 145 pmol/μL of each of the seven $^{15}$N-labeled peptides (MT-2, MT-3, MT-1E, MT-1G2, MT-1X, MT-1M, MT-1F) served as the internal standard for absolute quantitation experiments in the HK-2 metallothionein-3 cells. For the breast cells, a reference mixture containing 100 pmol/μL of each of the three $^{15}$N-labeled peptides (MT-2, MT-1E, MT-1X) was used as the internal standard for absolute quantitation.

Trypsin Digestion—For relative quantitation, 300 μg each of $^{14}$N-labeled control cytosol and $^{15}$N-labeled Cd-treated cytosol were combined. For absolute quantitation, 1 μl of $^{15}$N-labeled metallothionein peptide reference mix was added to either 300 μg of $^{14}$N-labeled control or Cd-treated cytosol. Samples were incubated with modified trypsin, 2% w/w (Trypsin Gold, Promega, Madison, Wis.) overnight at 37° C. The reaction was stopped by the addition of formic acid to 0.1% final concentration. Peptides were desalted online via HPLC through a self-packed Magic C18AQ column (200A pore size, 5 micron diameter particles, MICHROM Bioresources, Auburn, Calif.) using 0.15 ml/min Buffer A (0.1% formic acid) for ~20 minutes. The peptides were then eluted onto the SCX column using a 500 μl injection of 75% acetonitrile and 0.1% formic.

Chromatography—Peptides were then fractionated on a 2.1 mm×25 cm poly LC polysulfoethyl A self-packed strong cation exchange (SCX) analytical column with a 60 min linear gradient using Buffer A (0.1% formic acid) and from 0-25% Buffer B (0.1% formic acid; 1 M NaCl; 10% acetonitrile) at 0.15 ml/min. Fractions were collected every seven minutes and screened by mass spectrometry to locate the metallothionein peptides. The metallothionein peptide-containing fraction was evaporated to dryness, and reconstituted in 24 μl 8 M HCl containing 0.5 M dimethyl sulfide. The reaction was incubated 30 minutes at room temperature to reduce methionine sulfoxides (Shechter, *J Biol Chem* 261: 66-70 (1986). The reaction was then quenched by the addition of 12 μl 5 M NaOH. Precipitated salt was pelleted by centrifugation at 14,000×g for 2 minutes at room temperature and the supernatant was collected. The sample was immediately loaded onto a self-packed 100 μm×10 cm Magic C18AQ column (200 Å pore size, 5 micron diameter particles, MICHROM Bioresources, Auburn, Calif.) using a Tempo LC-MALDI (ABI SCIEX, Framingham, Mass.) integrated nano-HPLC/spotter. The column was equilibrated with 97% Buffer A (0.1% formic acid, 2% acetonitrile) and 3% Buffer B (0.1% formic acid, 98% acetonitrile) at a flow rate of 0.8 μl/min and peptides were fractionated with a 70 min linear gradient of 3% Buffer B/97% Buffer A to 20% Buffer B/80% Buffer A. Fractions were spotted every 0.18 seconds onto a MALDI target plate with post-column mixing of an equal volume of 10 mg/mL α-cyano-4-hydroxycinnamic acid (CHCA) in 75% acetonitrile, 0.1% formic acid. The column was recycled with 70% Buffer B/30% Buffer A for 5 minutes and then re-equilibrated with 3% pump B for 10 minutes.

Mass Spectrometry—The samples were analyzed by MS and MS/MS using an ABI 4800 MALDI-TOF/TOF mass spectrometer. For MS, laser intensity was 3200 to 3500 and 900 spectra were accumulated over 30 subspectra at 30 shots per subspectrum. The precursor ion mass range was limited to m/z 1800-3000. Resolution was typically 15000. Metallothionein peptide identities were confirmed by MSMS. Laser intensity was 4000. Spectra were accumulated over 30 subspectra at 30 shots per subspectrum. Unprocessed .t2d files were centroided and converted to .mgf files using the Peaks to Mascot tool on the AB Sciex 4000 Explorer software (version 3.5.28193). Metallothionein peptides were identified using Mascot version 2.3.02 (Matrix Science Inc., Boston, Mass.). Spectra were searched against the human proteome in the UniProt protein database (version 15.15). Search parameters were set at precursor peptide mass tolerance of 1.2 Da; fragment ion tolerance of 0.6 Da; enzyme-trypsin; fixed modification—cysteine $^{15}$N-carbamidomethylation; variable modifications—acetylation (protein N-term), methionine oxidation, cysteine $^{14}$N-carbamidomethylation; missed cleavages—up to two. Peptide mass errors were typically less than 100 ppm. Mascot ion scores were routinely 60-150.

Relative and Absolute Quantitation—The mean monoisotopic peak intensity was determined for each metallothionein $^{14}$N and $^{15}$N precursor ion across three to five spots spanning the precursor ion peak. The minimum signal to noise ratio accepted for a given peak was 20. The mass difference between pairs of $^{14}$N- and $^{15}$N-labeled metallothionein precursor ion pairs was 5 Da. Intensities of the $^{15}$N-labeled monoisotopic peaks were corrected for the contribution of the overlapping $^{14}$N peptide n+6 isotopic peak using the equation $H_{corr}=H-(L*C)-(H-L*C)(P*P')$ where H and L are the areas of the monoisotopic peak of the heavy-labeled and light-labeled precursor ions respectively, C is the percent contribution of the n+6 isotopic peak of the light precursor ion, P is the atom percent $^{14}$N contamination in $^{15}$N iodoacetamide, P' is the atom percent purity of $^{15}$N iodoacetamide. The $^{14}$N contamination was based on 99 atom percent according to the manufacturer.

Real Time Analysis of Metallothionein Isoform mRNA Expression—Total RNA was purified from HK-2 MT-3, MCF-10A, Hs578T, MDA-MB-231, MCF-7, and T-47D cell pellets (biological replicates done in triplicates) using the manufacturer's standard TRI REAGENT (Molecular Research Center, Cincinnati, Ohio) protocol. The measurement of metallothionein isoform mRNA expression was assessed with real time RT-PCR utilizing previously described metallothionein isoform-specific primers (Mididoddi et al., Toxicol Lett 85:17-27 (1996)). The primers sequences used for metallothionein-1M consisted of:

```
                                   (SEQ ID NO: 14)
Up           GGGCCTAGCAGTCG;

(SEQ ID NO: 15)
Low          TGGCTCAGTATCGTATTG.
```

The primer sequences used for 18S rRNA expression were:

```
                                   (SEQ ID NO: 16)
Up           CGCCGCTAGAGGTGAAATTC;

(SEQ ID NO: 17)
Low          TTGGCAAATGCTTTCGCTC.
```

Forty nanograms of total RNA was subjected to RT-PCR amplification using the iScript One-Step RT-PCR kit (Bio-Rad Laboratories, Hercules Calif.) with SYBR Green using 0.2 µM of primers in a total reaction volume of 20 µL in an iCycler iQ real-time detection system (Bio-Rad Laboratories). Amplification was monitored by SYBR Green fluorescence and compared with that of a standard curve of each metallothionein isoform gene cloned into pcDNA3.1/hygro (+) and linearized with Fsp I. Cycling parameters consisted of a reverse transcription step at 50° C. for 10 minutes, denaturation at 95° C. for 15 seconds, annealing at 65° C. for 40 seconds, and extension at 72° C. for 40 seconds which gave the optimal amplification efficiency of each standard. For metallothionein-1M, 62° C. was used for the annealing temperature while the other cycling parameters listed above remained the same. The level of metallothionein isoform expression was normalized to that of 18S rRNA assessed by the same assay.

EXAMPLE 2

Detection of Metallothionein Isomers

This Example illustrates methods for identification of metallothionein isomers.

Detection of Synthetic N-Terminal Acetylated Metallothionein Peptides.

Acetylated N-terminal tryptic peptides for 11 human metallothionein isoforms were commercially synthesized, alkylated, and purified (Table 1).

TABLE 1

Human N-terminal tryptic MT peptides

| MT Isoform | Sequence | Expected m/z* | Retention Time (min.) | Identified in HK-2 cells | Identified in human breast cells in this study | Identified in RWPE cells | Identified in human certical kidney tissue | Identified in human cerebrum brain tissue |
|---|---|---|---|---|---|---|---|---|
| MT-1A | MDPNCSCATGGSCTCTGSCK SEQ ID NO: 18 | 2252.8 | 36.5 | No | No | No | No | No |
| MT-1B | MDPNCSCTTGGSCACAGSCK SEQ ID NO: 19 | 2222.8 | 36.5 | No | No | No | No | No |

TABLE 1-continued

Human N-terminal tryptic MT peptides

| MT Isoform | Sequence | Expected m/z* | Retention Time (min.) | Identified in HK-2 cells | Identified in human breast cells in this study | Identified in RWPE cells | Identified in human certical kidney tissue | Identified in human cerebrum brain tissue |
|---|---|---|---|---|---|---|---|---|
| MT-1E | MDPNCSCATGGSCTCAGSCK SEQ ID NO: 20 | 2222.8 | 37.0 | Yes | Yes, but not in all lines | Yes | Yes | Yes |
| MT-1F | MDPNCSCAAGVSCTCAGSCK SEQ ID NO: 21 | 2234.8 | 46.9 | Yes | No | Yes | Yes | Yes |
| MT-1G1 | MDPNCSCAAAGVSCTCASSCK SEQ ID NO: 22 | 2335.9 | 48.2 | No | No | Yes | Yes | Yes |
| MT-1G2 | MDPNCSCAAGVSCTCASSCK SEQ ID NO: 23 | 2264.8 | 47.2 | Yes | No | Yes | Yes | No |
| MT-1H | MDPNCSCEAGGSCACAGSCK SEQ ID NO: 24 | 2220.8 | 38.3 | No | No | No | Yes | No |
| MT-1L | MDPNCSCATGGSCSCASSCK SEQ ID NO: 25 | 2238.8 | 35.8 | No | No | No | No | No |
| MT-1M | MDPNCSCTTGVSCACTGSCK SEQ ID NO: 26 | 2294.8 | 45.8 | Yes | No | Yes | No | No |
| MT-1X | MDPNCSCSPVGSCACAGSCK SEQ ID NO: 27 | 2246.8 | 48.4 | Yes | Yes | Yes | Yes | Yes |
| MT-2 | MDPNCSCAAGDSCTCAGSCK SEQ ID NO: 28 | 2250.8 | 38.5 | Yes | Yes | Yes | Yes | Yes |
| MT-3 | MDPETCPCPSGGSCTCADSCK SEQ ID NO: 29 | 2418.8 | 45.1 | Yes | No | No | No | Yes |

*m/z includes N-terminal acetylation and five $^{14}$N carbamidomethyl modifications of the Cys residues. The $^{15}$N carbamido-methylated peptides have a m/z 5 Da greater than the m/z shown.?
*ppm errors were consistently less than 50 for all MT isoforms in experimental
runs. N-terminal tryptic MT peptides account for 30-36% sequence coverage across all isoforms. 'MT-1G1 was not successfully synthesized but was endogenously detected in alternative cells and tissues.

Figure 7A:
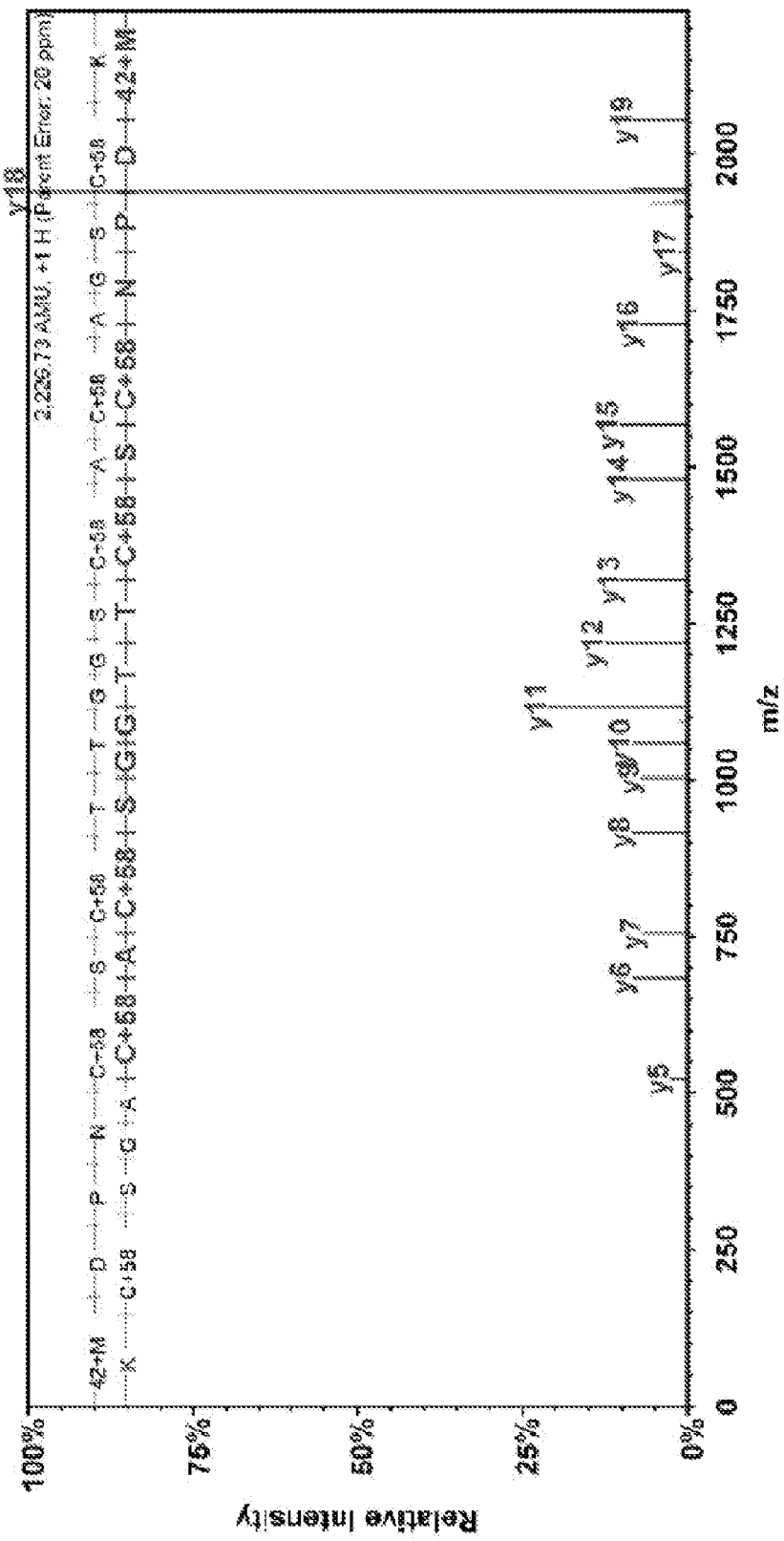
Figure 8A:
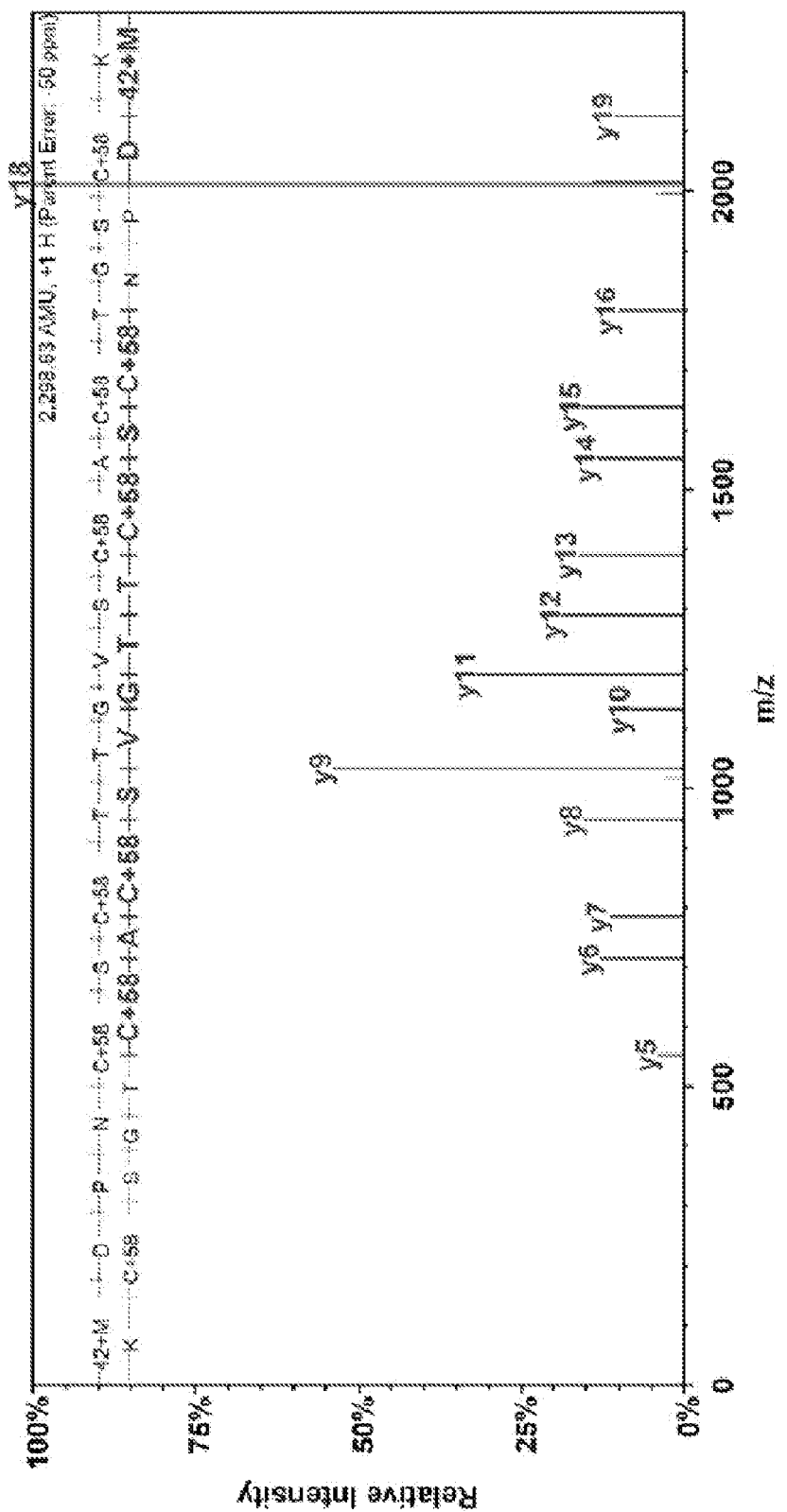
Figure 9A:
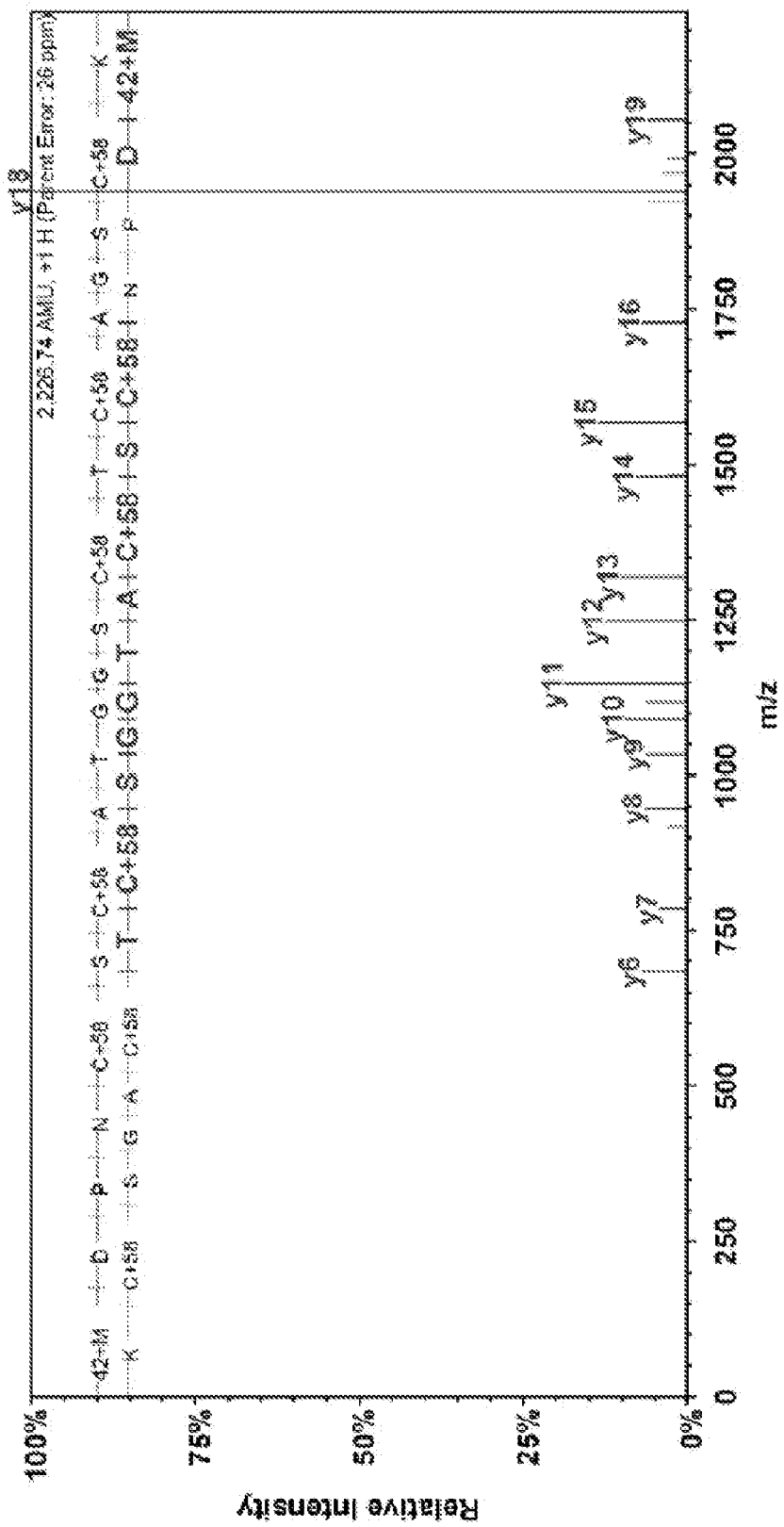
Figure 10A:
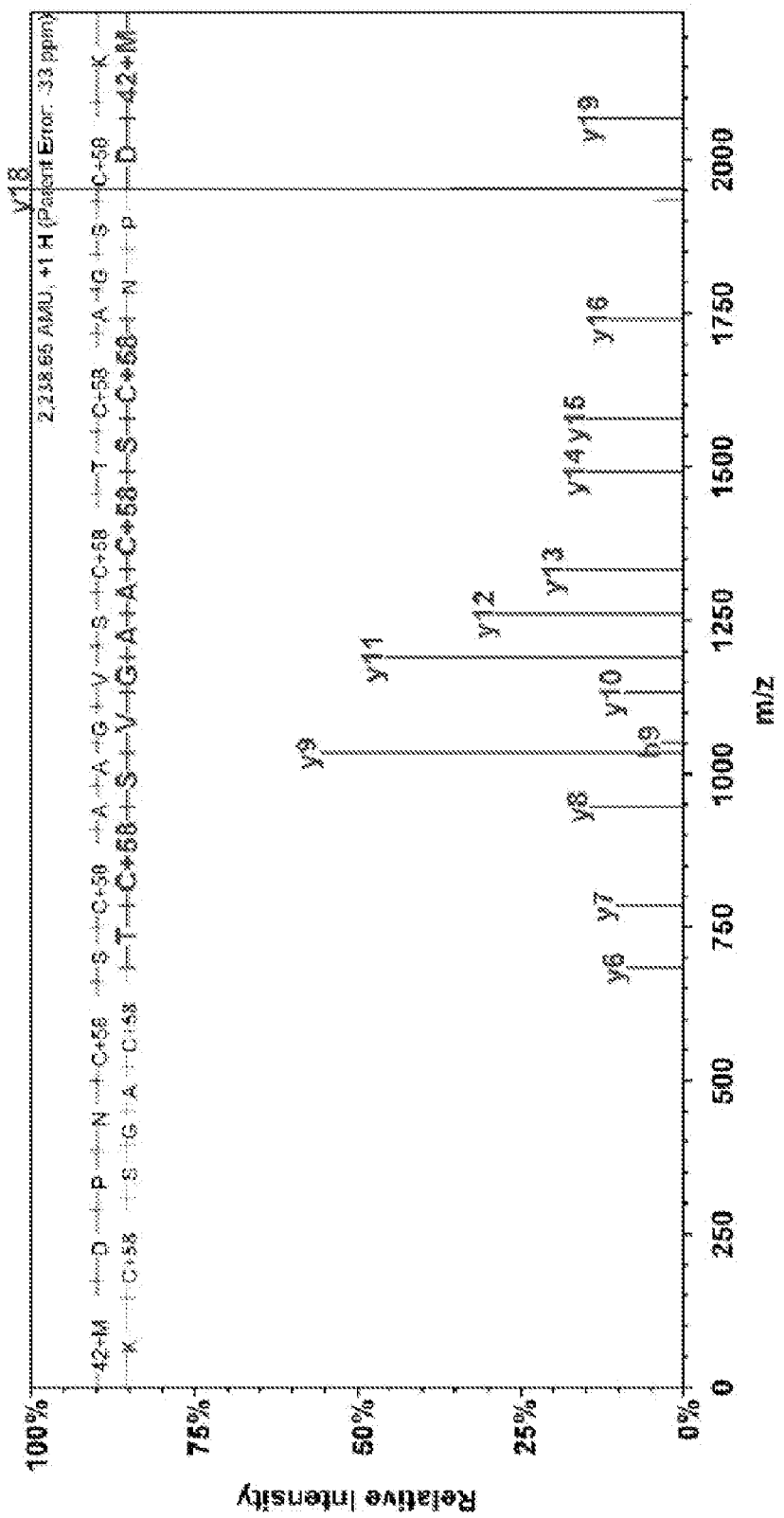
Figure 11A:
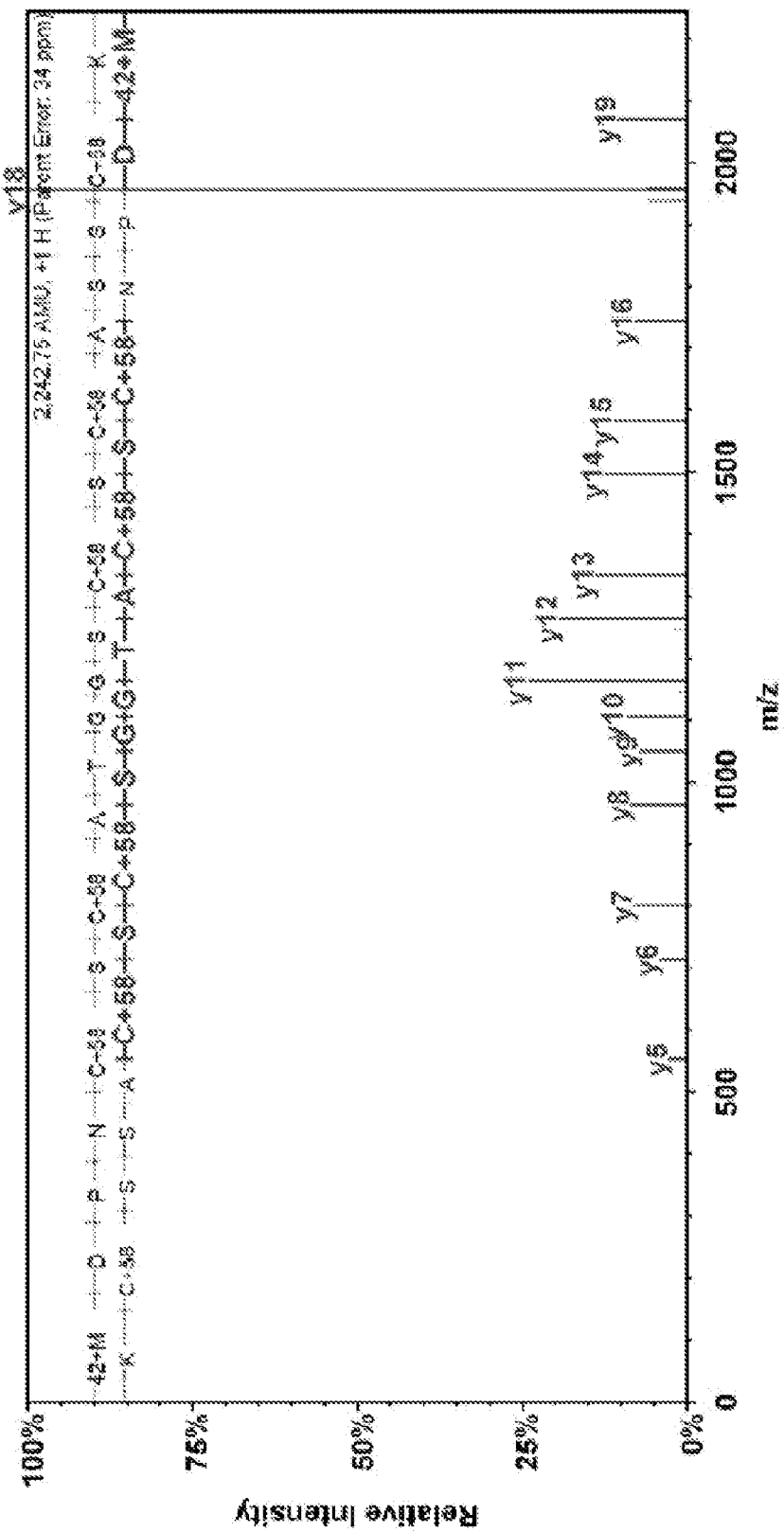
Figure 12A:
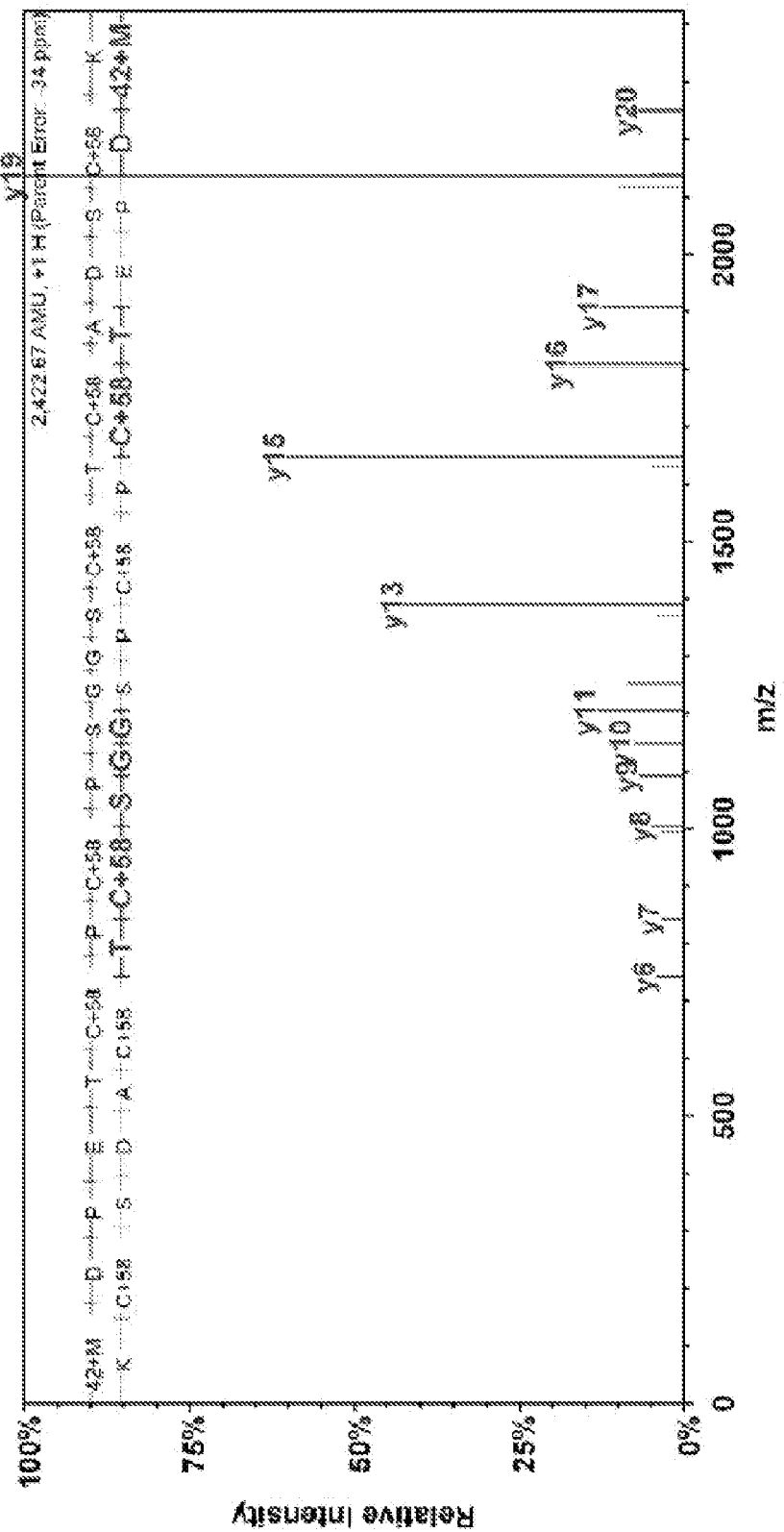
Figure 13A:
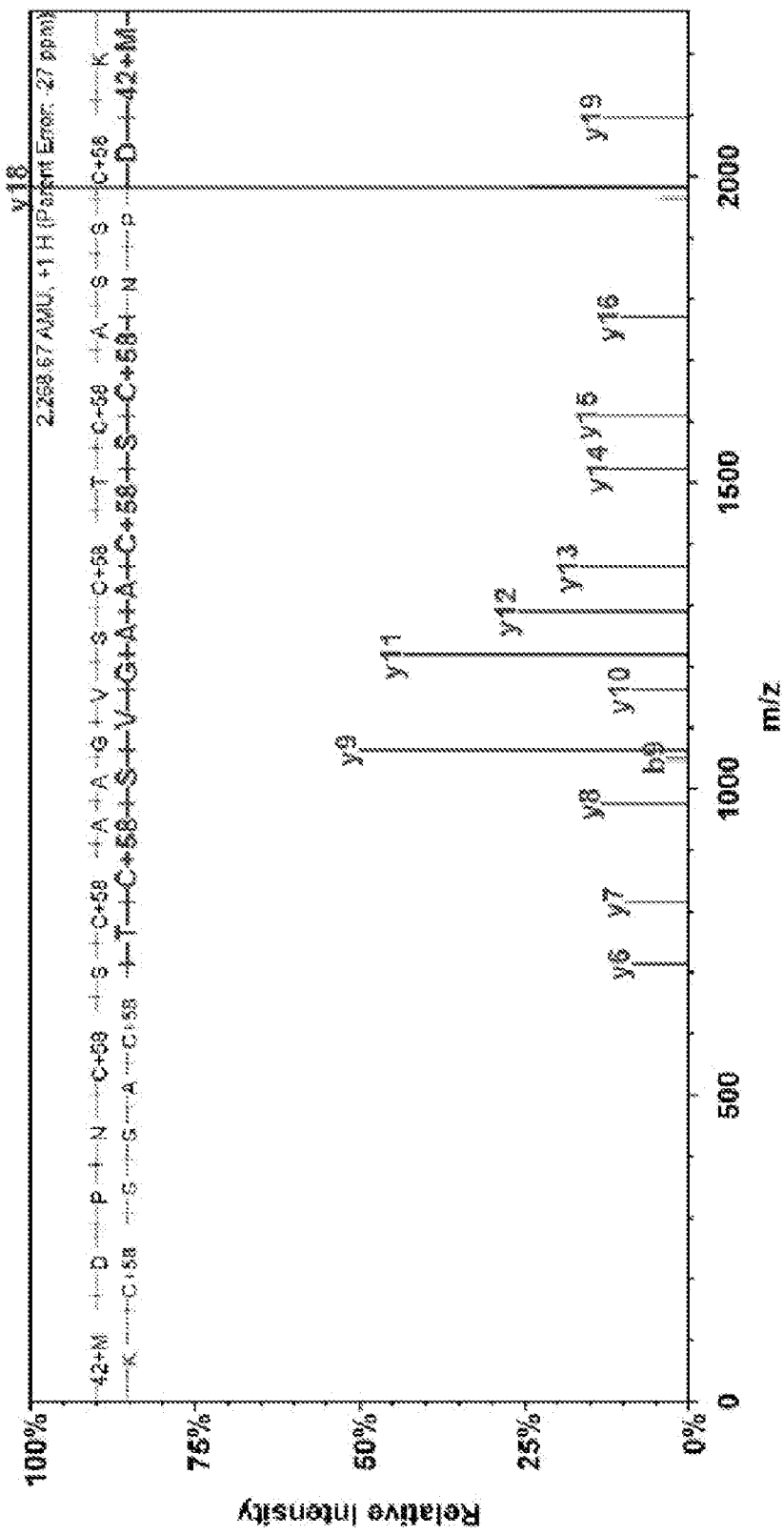
Figure 14A:
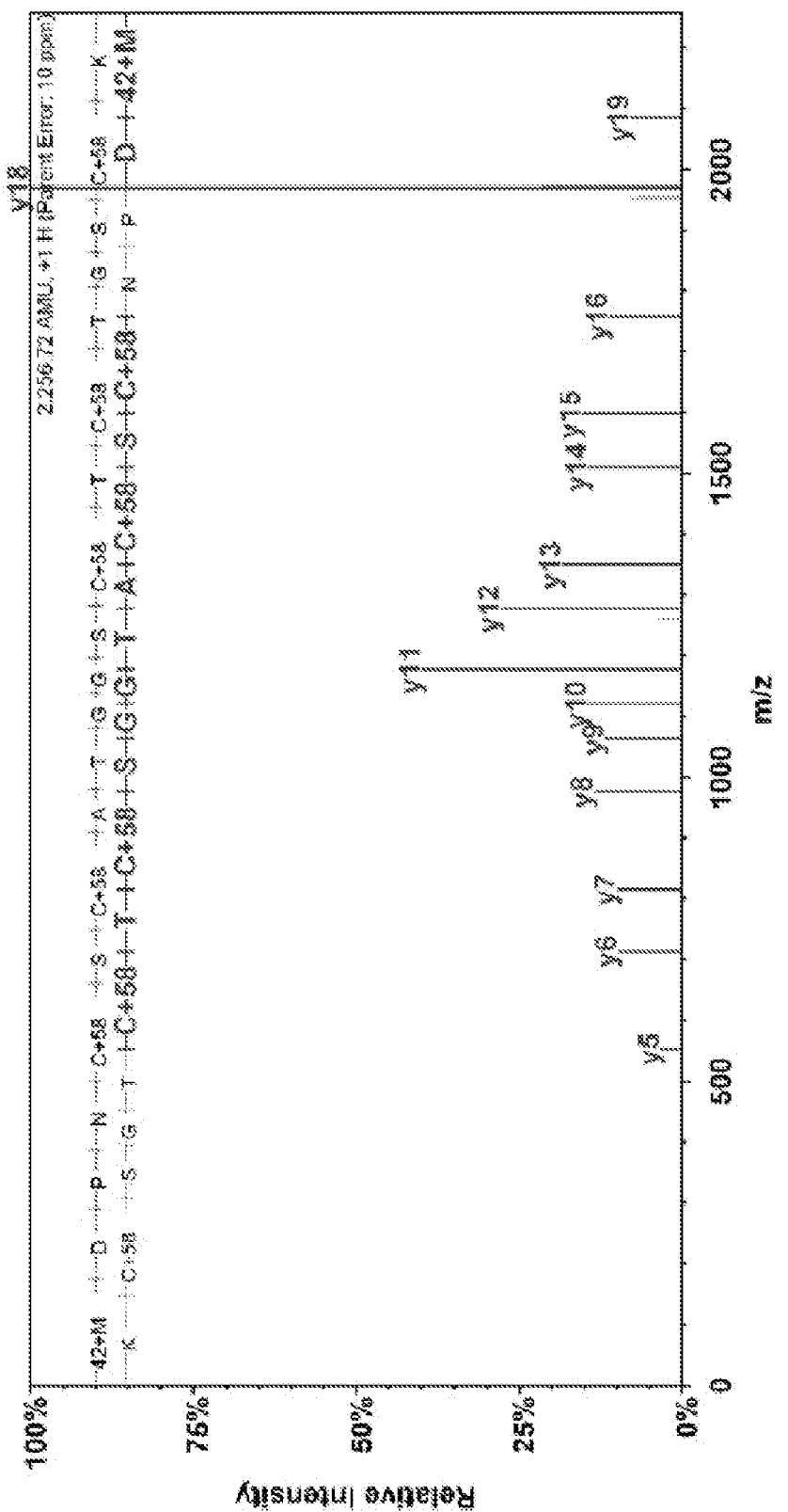
Figure 15A:
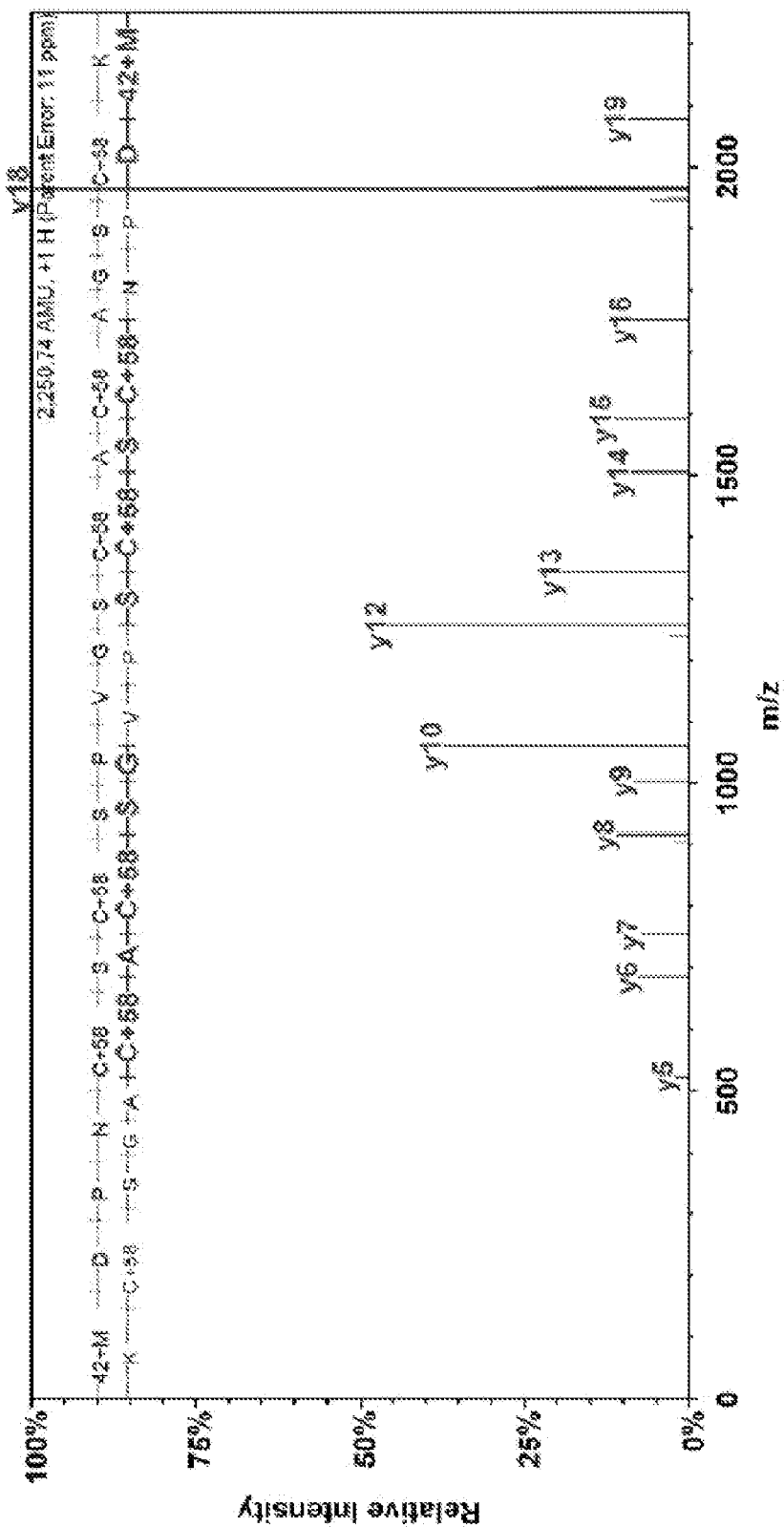
Figure 16A:
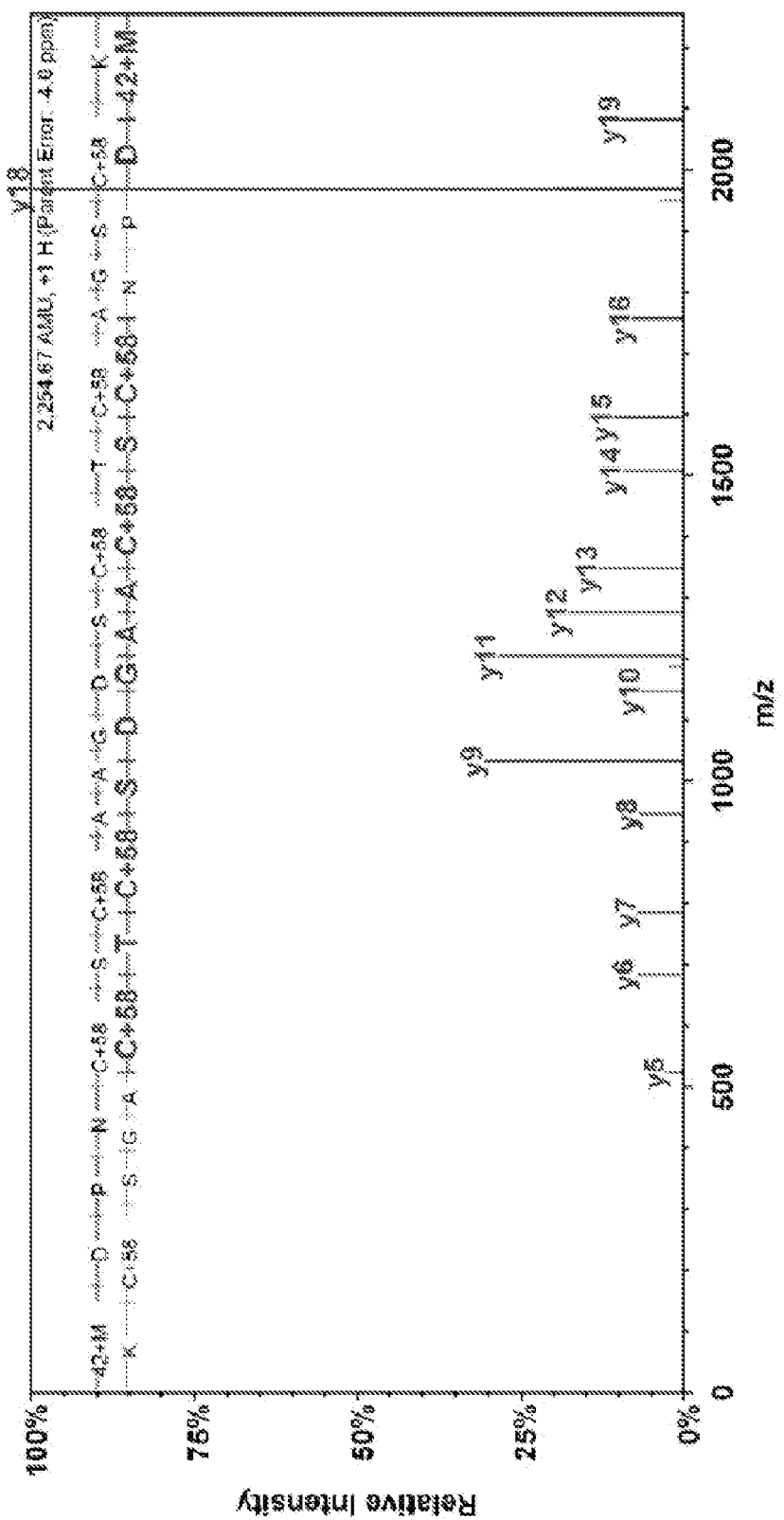
Figure 17A:
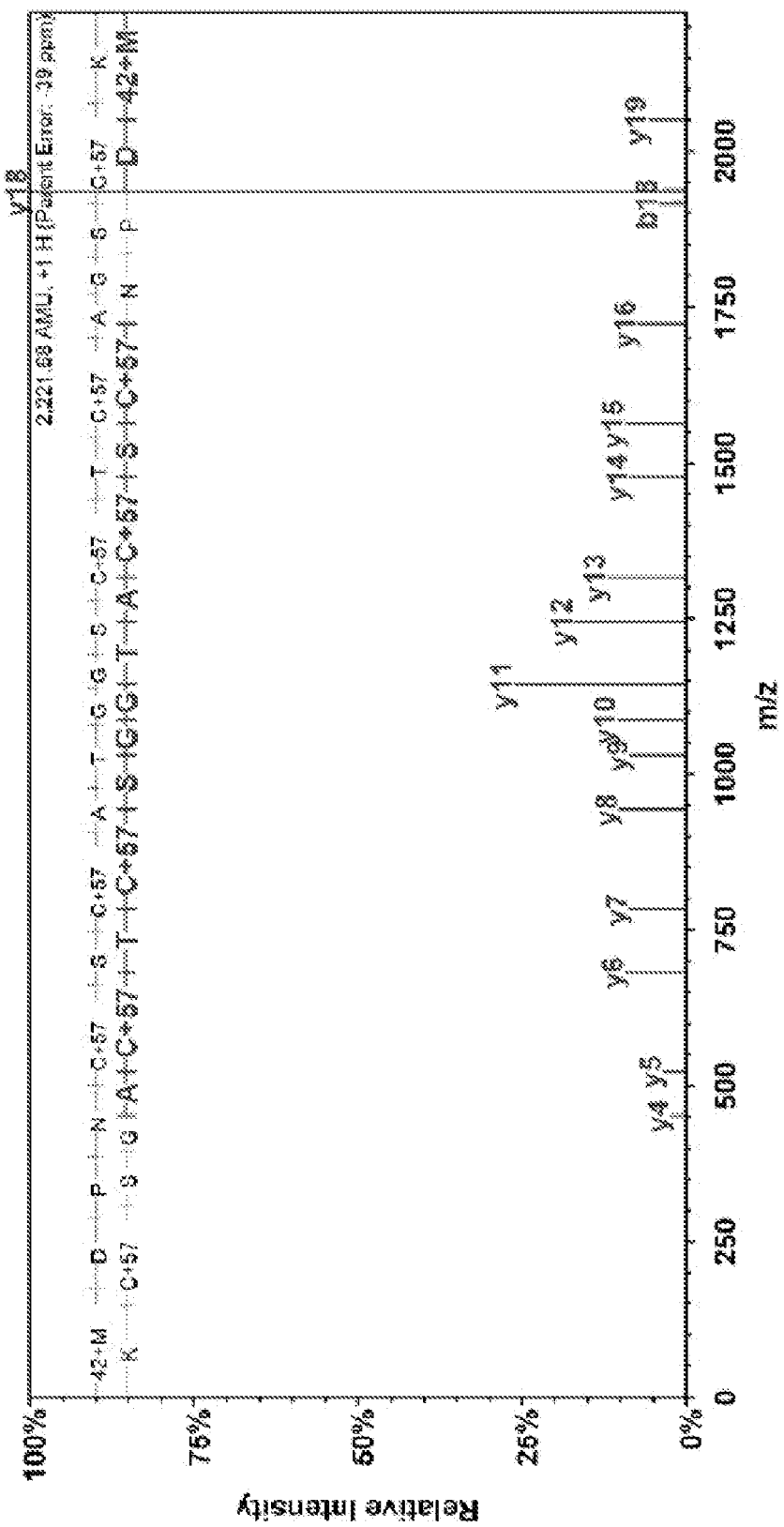
Figure 18A:
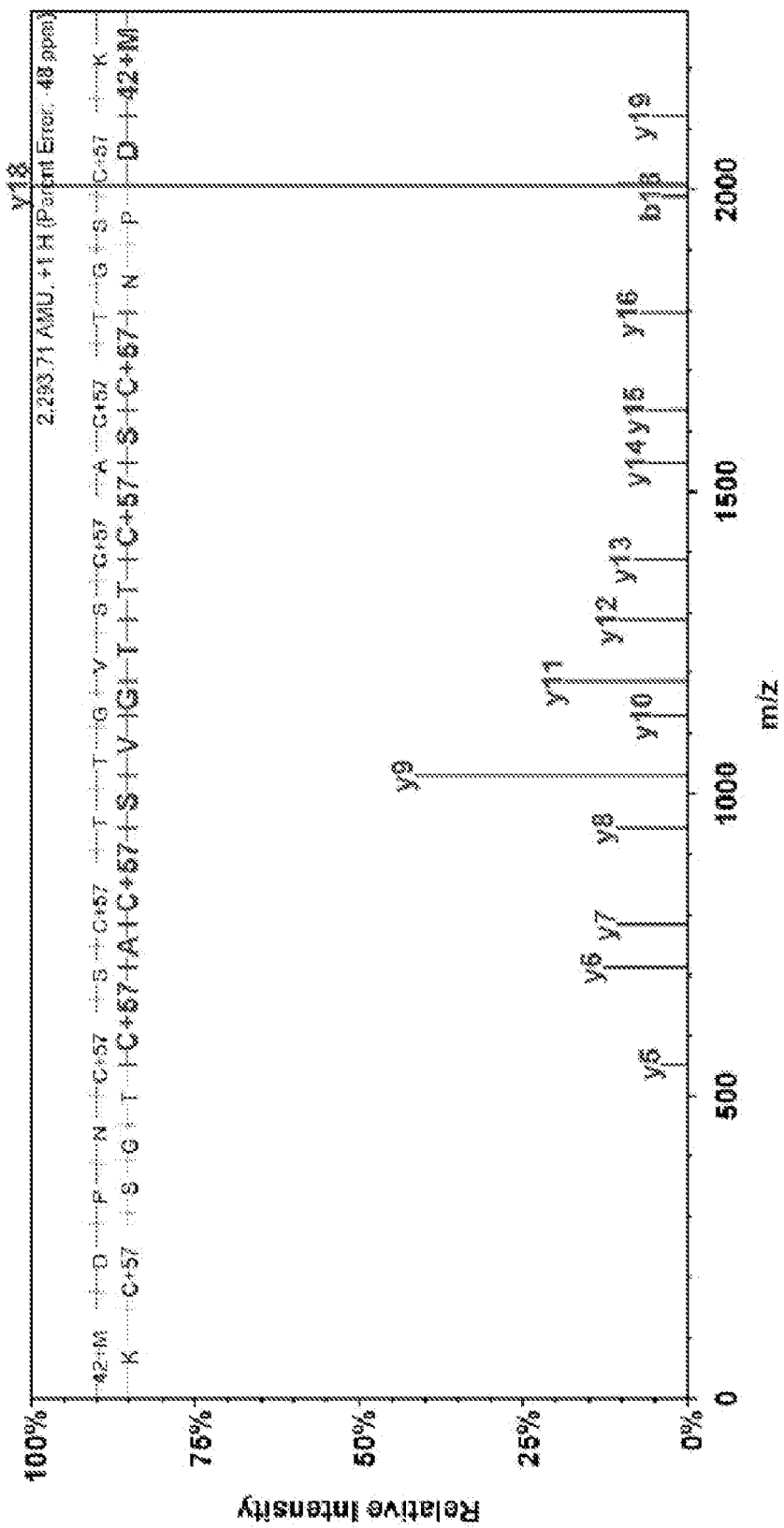
Figure 19A:
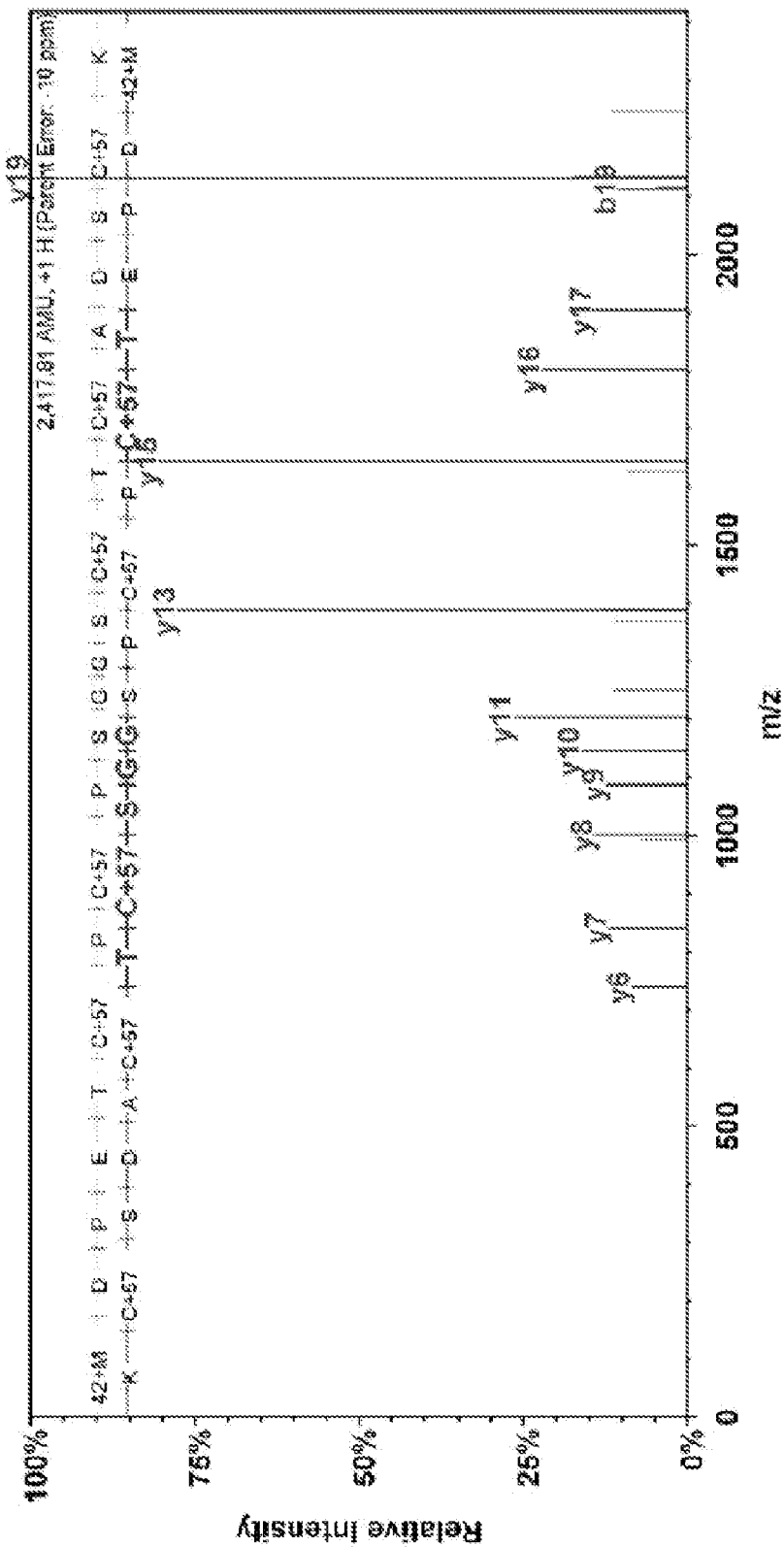
Figure 20A:
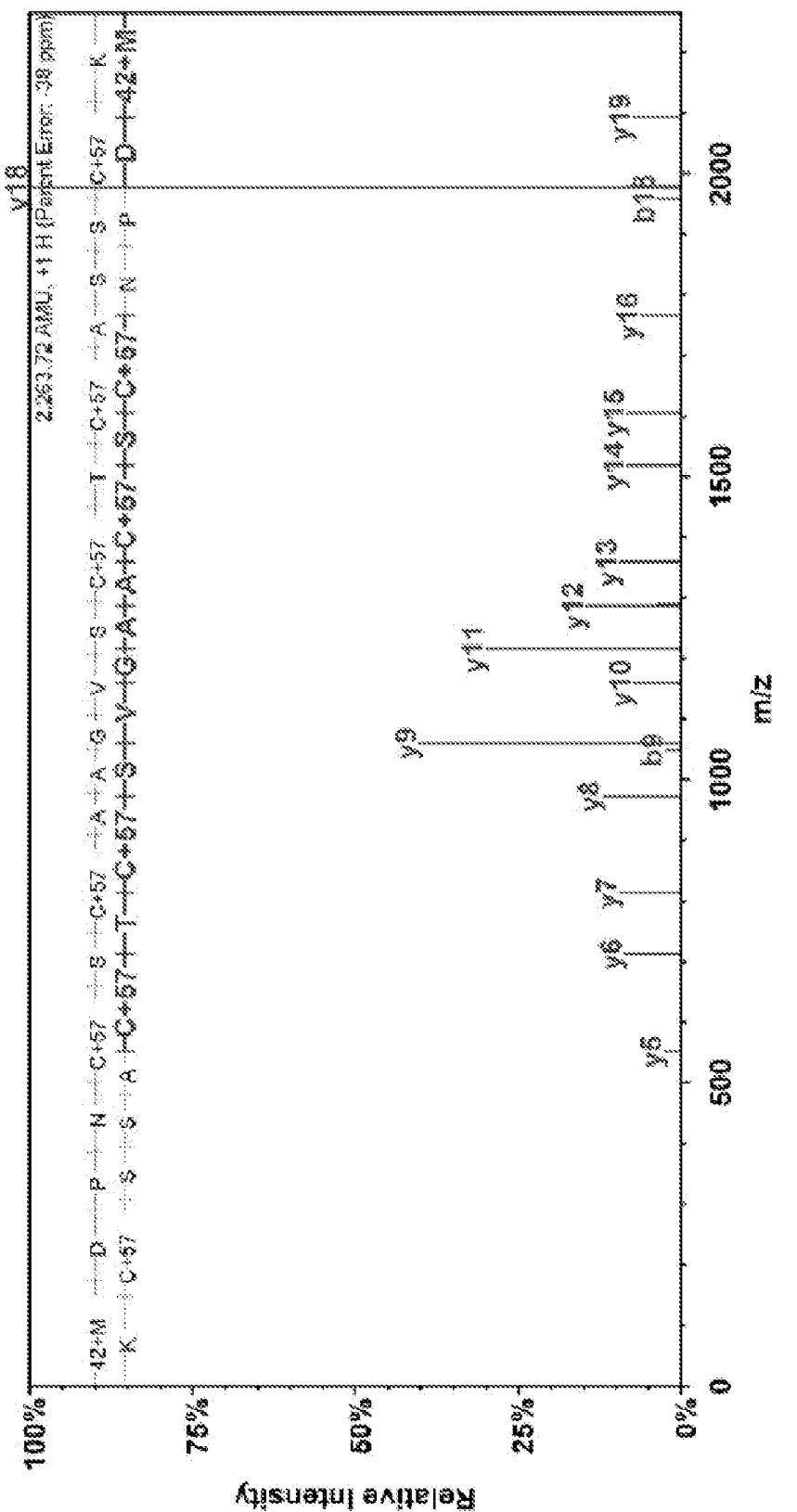
Figure 21A:
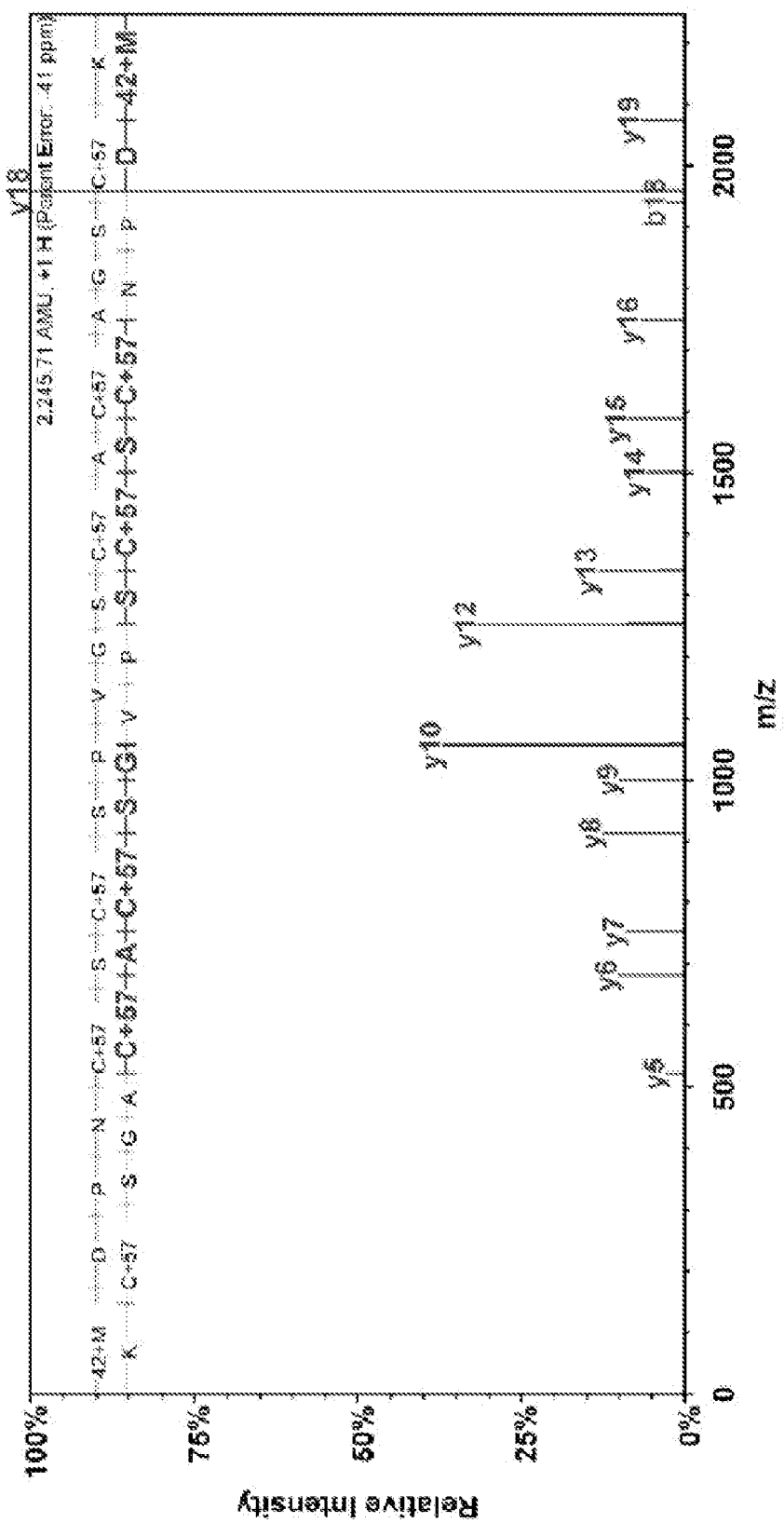
Figure 22A:
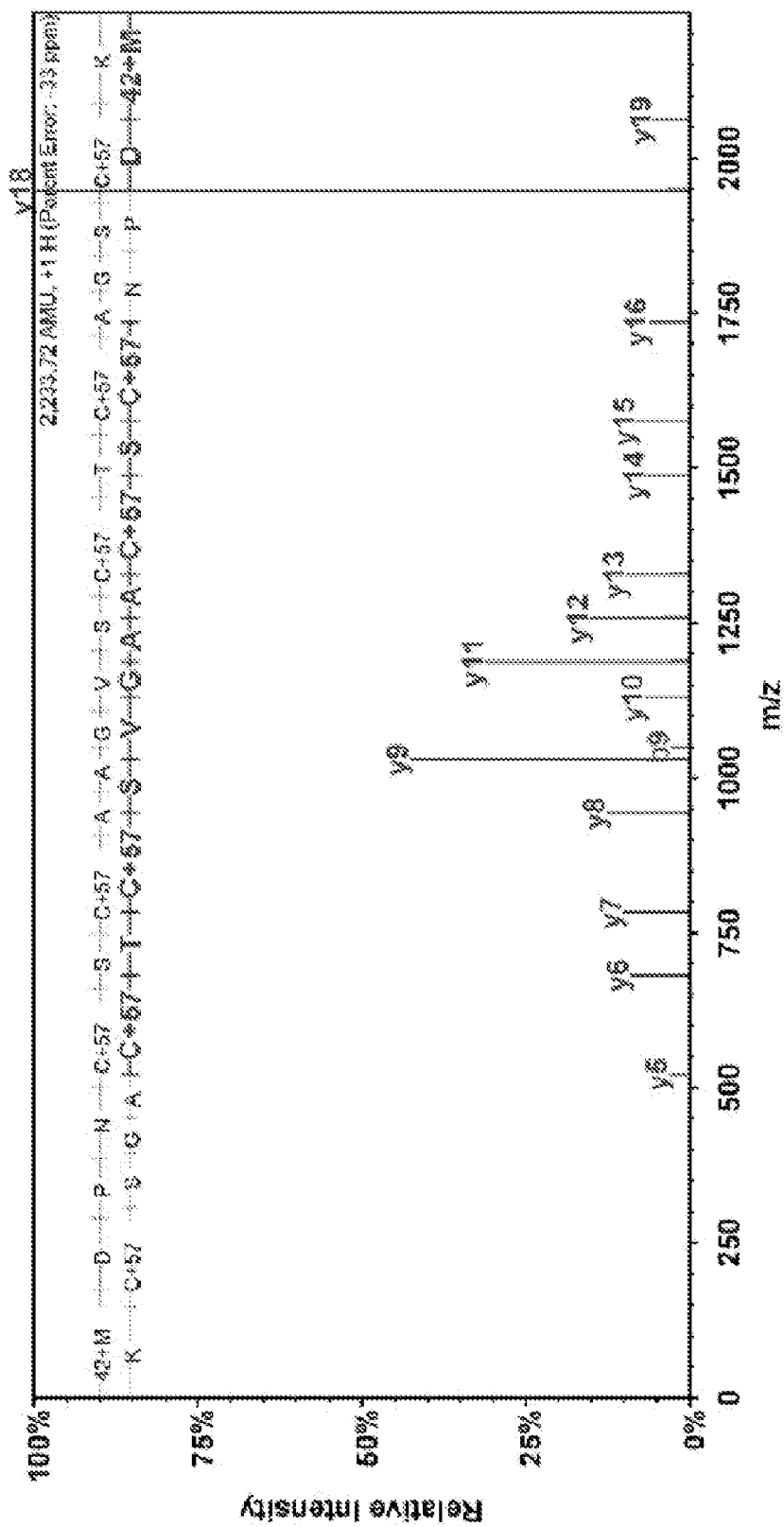
Figure 23A:
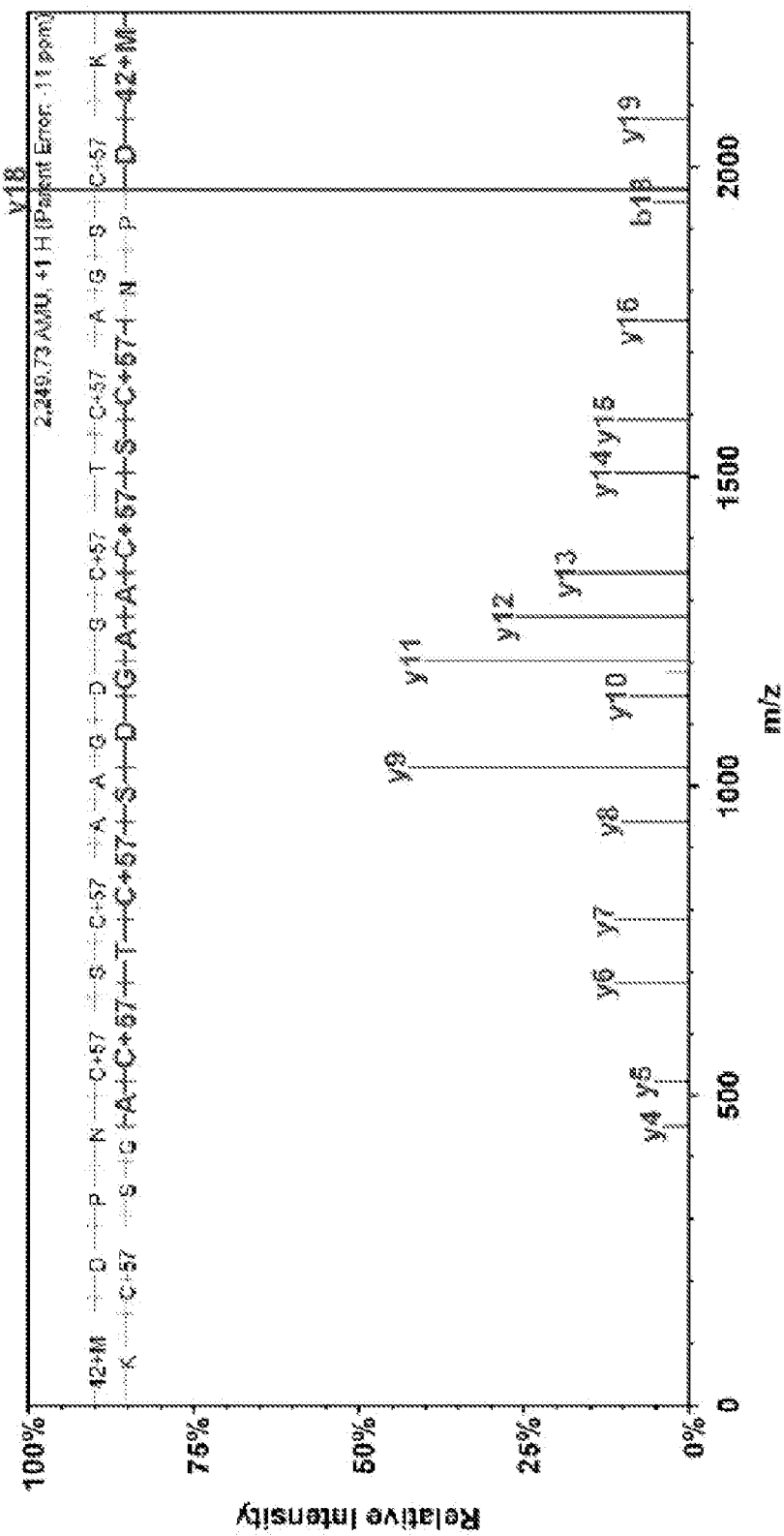

The identities of each peptide were confirmed by MSMS (FIGS. 6-23). FIGS. 6-23 show the resulting MSMS spectra of the N-terminal acetylated tryptic peptide from each metallothionein isoform along with their fragmentation tables. The fragmentation table is table of ions that can result when each metallothionein isoform precursor peptide (the N-terminal acetylated tryptic peptide) is fragmented. The shaded masses (numbers) are the b and y ions that were experimentally detected in MSMS. When peptides fragment in MSMS, the cleavage is typically at the peptide bond. N-terminal (b) and C-terminal (y) fragment are generated. The difference in mass in any b or y ion series is equivalent to the mass of the amino acid(s) in the peptide sequence. The more b and y ions detected, the higher the confidence in the sequence identification for each peptide. For example, FIG. 7B is the fragmentation table of the tryptic peptide of heavy-labeled MT-1E, which is 20 amino acids in length. The y ion column shows the theoretical masses of the fragmented ions that should be observed when this peptide is fragmented using MSMS. The shaded numbers are the actual experimental ions observed in the experiment. As shown, almost the complete y ion series was observed and including the 1 b ion (b18).

As shown in Table 2, the ionization intensities of these peptides were comparable when analyzed in the same experiment. In particular, Table 2 lists the total ionization of 0.25 μg (calculated by area under the curve analysis through reversed phase HPLC) reference metallothionein peptides after labeling and purification. Final purity levels are estimated to be >95% for each isoform.

TABLE 2

| Isoform | Initial Purity (%) | Total Ionization | Normalized Ionization |
|---|---|---|---|
| MT-3 | 73.32 | 265429.84 | 0.81 |
| MT-1L | 34.52 | 294155.78 | 0.90 |
| MT-1X | 90.28 | 325968.10 | 1.00 |
| MT-1H | 17.65 | 234696.60 | 0.72 |
| MT-1E | 44.86 | 273031.63 | 0.84 |
| MT-1B | 34.65 | 273031.63 | 0.84 |
| MT-2 | 73.27 | 154424.32 | 0.47 |
| MT-1M | 25.69 | 126377.40 | 0.39 |
| MT-1G2 | 10.15 | 138968.18 | 0.43 |
| MT-1F | 12.84 | 163048.02 | 0.50 |
| MT-1A | 11.01 | 110516.85 | 0.34 |

These results demonstrate that all metallothionein protein isoforms can be detected that are expressed in detectable amounts in biological sample.

Identification of Endogenous N-Terminal Metallothionein Peptides after Enrichment.

Optimized one-dimensional reversed-phase chromatography followed by mass spectrometry was sufficient to identify seven metallothionein isoforms in Cd-induced HK-2 human kidney epithelial cell cytosol (FIG. 1D and FIGS. 17-23).

Figure 24:
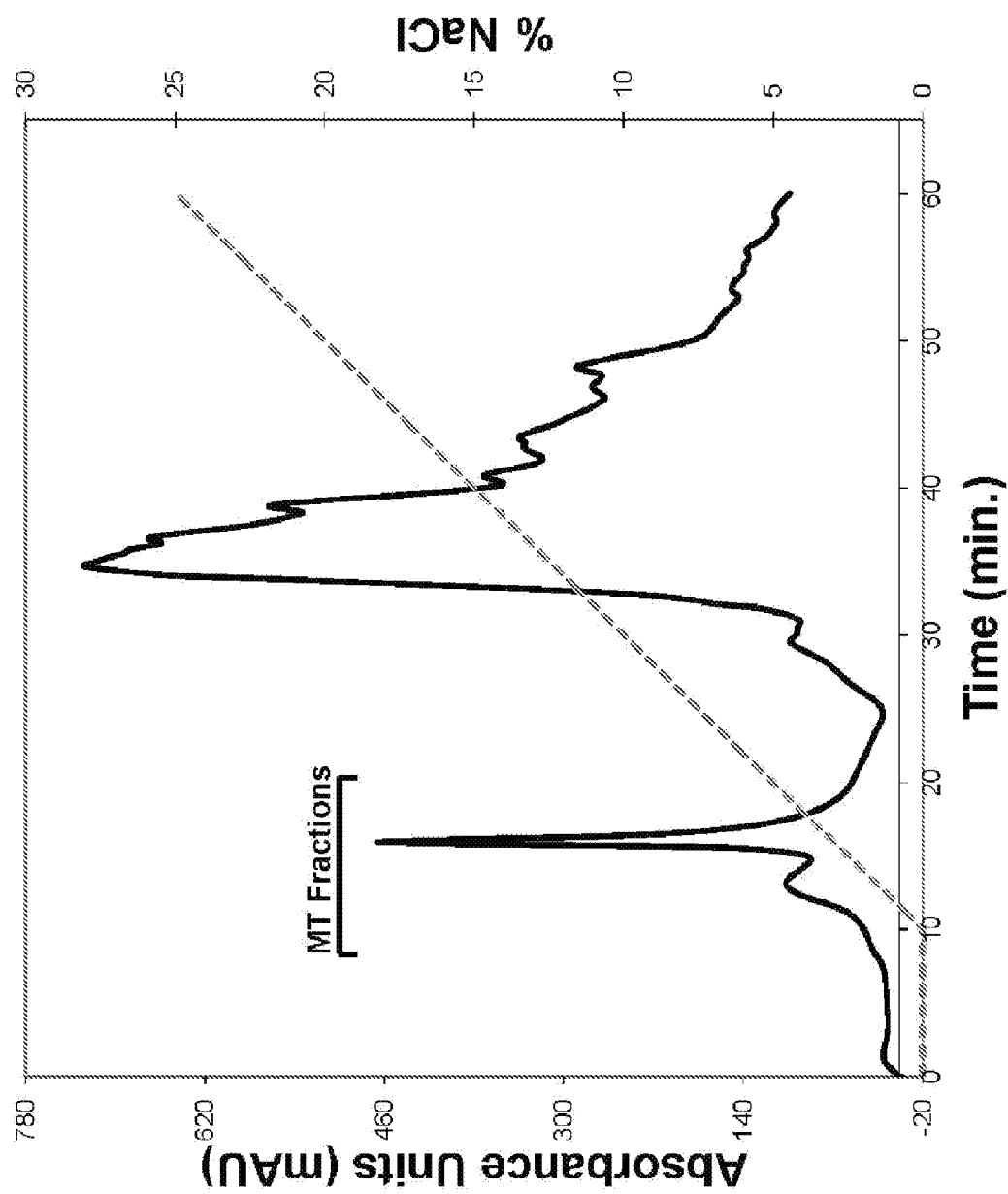
FIG. 24 illustrates optimized strong cation exchange (SCX) chromatography of tryptic digested cytosolic lysate with ~100 pmol/isoform pure acetylated N-term metallothionein peptide standards added. Fractions two and three (7-21 minutes) contain the acetylated N-term tryptic metallothionein peptides along with other non-metallothionein 0 and +1 charged peptides. The dashed grey line indicates NaCl gradient. The black line indicates the point of the tryptic peptide absorbance at 214 nm. The acetylated N-term metallothionein peptides elute with ~20-25 mM NaCl.

Reversed-phase chromatography conditions, optimized to capture and analyze these peptides by MALDI MS, revealed that all peptides were separable, yet clustered in a defined region of high m/z early-eluting precursor ions referred to as the metallothionein zone. The fully alkylated peptides were unusually hydrophilic for their size range, which was between 2200 and 2500 m/z. Heat maps showed that the metallothionein peptides were remarkably segregated almost completely from the typical smaller early-eluting and larger more hydrophobic peptides (data not shown). Only three isoforms could be detected in cytosol from uninduced cells and their signals were very weak (not shown). A second chromatography step was used to reduce sample complexity and get better sampling depth. Strong cation exchange (SCX) chromatography effectively separated the metallothionein peptides, which eluted early in the gradient away from the bulk of tryptic peptides (FIG. 24). The two-dimensional separation of uninduced HK-2 samples increased the sensitivity sufficiently to detect all of the metallothioneins found in the Cd-induced sample except MT-1M. Increasing the starting amount of cytosol from 300 µg to 800 µg did not allow detection of additional N-terminal MT peptides.

N-Terminal Modifications of Endogenous Metallothioneins.

Almost all N-terminal peptides from endogenous metallothioneins were N-acetylated. A small amount of unacetylated MT-2 (10% or less of total MT-2 signal; not shown) was routinely detected in one-dimensional separation of Cd-induced HK-2 cytosol. A trace amount of unacetylated MT-1E was observed once, but not for any of the other metallothioneins.

In addition to acetylation, early experiments showed some truncations of the N-termini—most notably the loss of the acetyl-Met-Asp dipeptide (not shown). Refinement of the isolation and enrichment strategy greatly reduced the relative intensities of these truncated precursors, suggesting that they may have been artifacts of sample preparation. The acetyl-Met-Asp dipeptide of mammalian metallothioneins precedes a proline residue. The Asp-Pro bond in general and that of mammalian metallothioneins in particular are acid labile (Landon, *Meth Enzymol* 47:145-149 (1977); Kojima et al., *Proc Natl Acad Sci USA* 73:3413-3417 (1976); Kissling & Kagi, *FEBS Lett* 82:274-250 (1977)). This susceptibility to cleavage may explain in part why multiple N-terminal truncations of metallothioneins are observed in the PeptideAtlas database (Desiere et al., *Genome Biol* 6:R9 (2004); Desiere et al., *Nucl Acids Res* 34:D655-D658 (2006).

As much as 40% of the total ion signal for a given N-terminal metallothionein peptide was in the methionine sulfoxide form. This is considered a high degree of oxidation based on a recent quantitative proteomic study of intracellular methionine oxidation in human Jurkat cells (Ghesquiére et al., *Molec Cell Proteomics* 10:1-12 (2011). Though N-terminal metallothionein peptides were not detected in this study the acetyl-Met-Asp-Pro sequence of metallothionein N-termini would classify it as highly susceptible to oxidation based on sequence preferences revealed by this study. The susceptibility of these peptides to oxidation was reinforced by the observation that addition of synthetic metallothionein peptides to cytosol caused them to achieve a similar degree of oxidation as the corresponding endogenous peptides. This oxidation appeared to occur before the chromatography steps.

For purposes of quantification, it was important to control the variability in methionine oxidation of metallothioneins. Reduction with dimethyl sulfide quantitatively reverted methionine sulfoxides to methionine, and collapsed the metallothionein zone into single dominant precursors for each isoform.

Validation of $^{14}$N and $^{15}$N Iodoacetamide for Quantitation of N-Terminal Metallothionein Peptides.

The enhanced sensitivity gained with two-dimensional LC and the simplification of precursor ion complexity with dimethyl sulfide treatment set the stage for quantitative profiling of metallothionein isoforms. $^{15}$N-iodoacetamide was selected as a stable isotope labeled compound because it is commercially available, gives a cumulative mass shift of 5 Da for N-terminal metallothionein peptides, and is well-characterized for its cysteine-specific reactivity in peptides. This reagent has probably not been used previously in stable isotope labeling experiments because a single Dalton mass shift would complicate quantitation due to the high degree of isotopic envelope overlap.

The commercially available $^{13}C_2$-iodoacetic acid was also tested. This compound gave a cumulative mass shift and no isotope effects were observed (not shown). The increased hydrophilicity introduced by the carboxylates weakened their retention during reversed phase chromatography sufficiently to compromise reproducible quantitation. Accordingly, $^{15}$N-iodoacetamide was a better reagent.

Figure 1B:
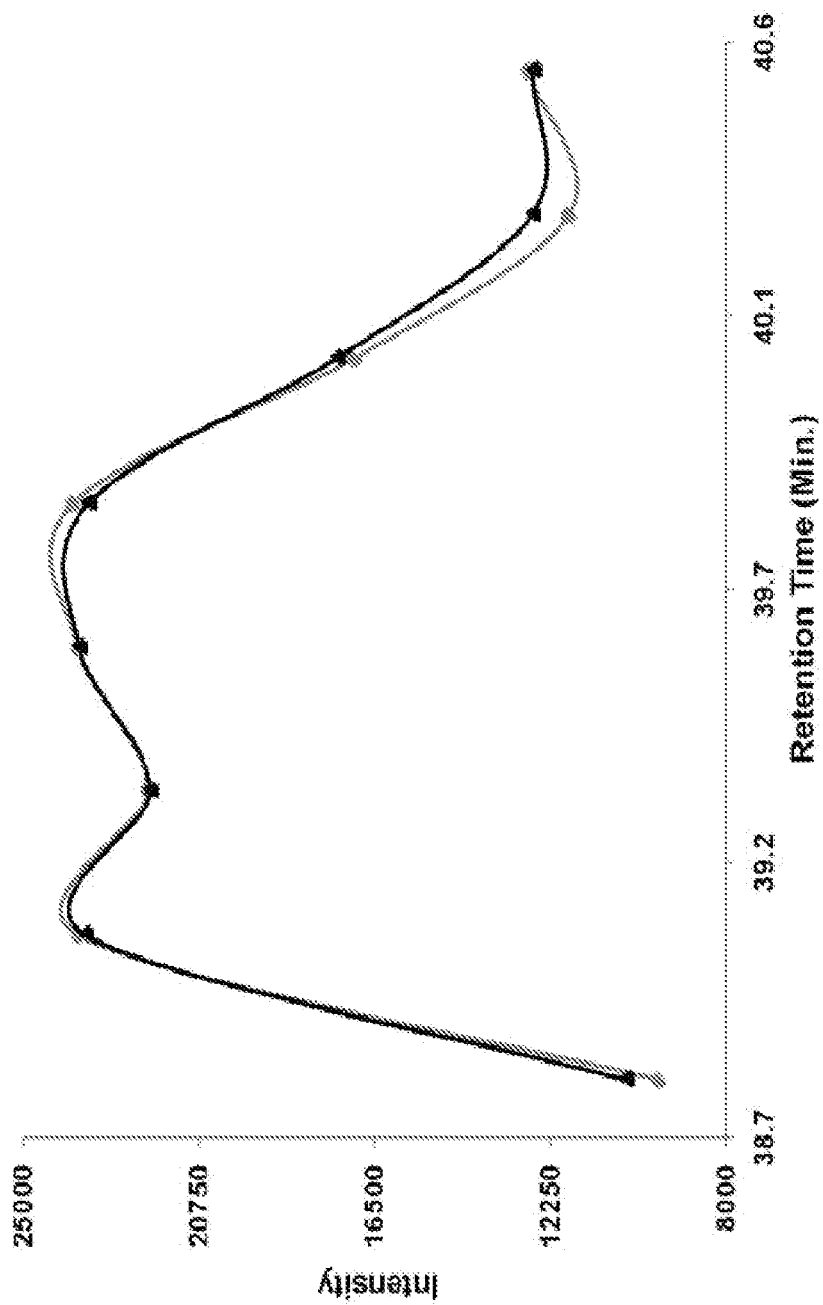
Figure 1C:
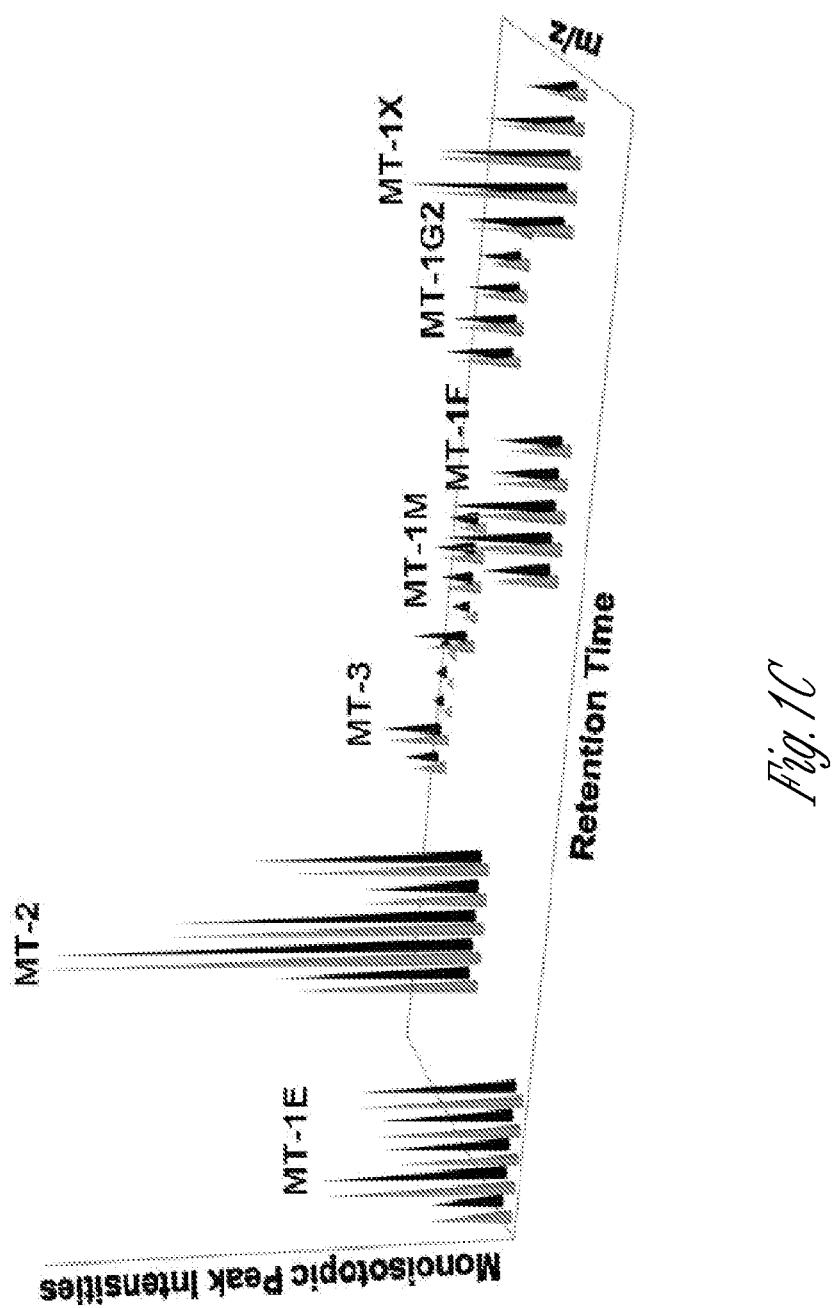

Cytosols from control and Cd-induced HK-2 cells were alkylated with $^{14}$N-iodoacetamide (light) and the Cd-induced sample is alkylated with $^{15}$N-iodoacetamide (heavy) respectively. Equal amounts were mixed and proteins were digested with trypsin. The N-terminal metallothionein peptides were enriched as described in the methods (Example 1) and analyzed by MALDI-TOF/TOF MS. FIG. 1A illustrates the isotopic envelopes for the light ($^{14}$N, grey lines) and heavy labeled ($^{15}$N, black lines) N-terminal acetylated tryptic peptides of MT-2 precursor ions. As expected, a 5 Da shift between the light (m/z 2250.7) and heavy (m/z 2255.7) monoisotopic peaks was observed. The monoisotopic peak intensities for the light and heavy precursors were plotted after correcting for isotopic overlap and purity of the $^{15}$N label (FIG. 1B). The 1:1 ratio of light to heavy monoisotopic peak intensities across the entire MT2 peak indicates that there is no isotope effect on the chromatographic behavior of the light and heavy-labeled metallothionein peptides. This reproducibility was maintained for all observed N-terminal metallothionein peptides (FIG. 1C).

Figure 2:
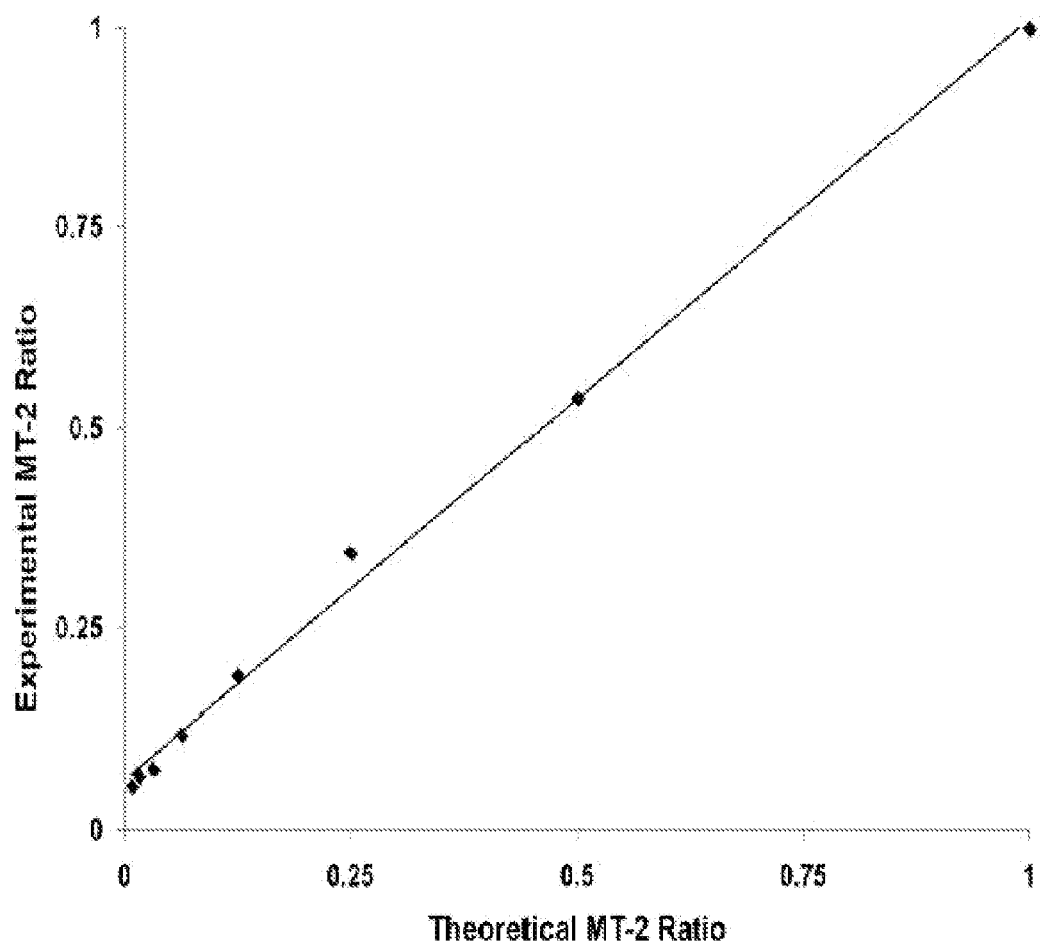
FIG. 2 illustrates the sensitivity and dynamic range of the relative quantitation of MT-2. A serial dilution of the light labeled MT-2 peptide was performed while constant levels of heavy-labeled MT-2 peptide were maintained to show the detection limits of the metallothionein quantitation assay. Two orders of magnitude were achieved. Dilution series consisted of: 1:1, 1:2, 1:4, 1:8, 1:16, 1:32, 1:64, and 1:128.
Figure 3A:
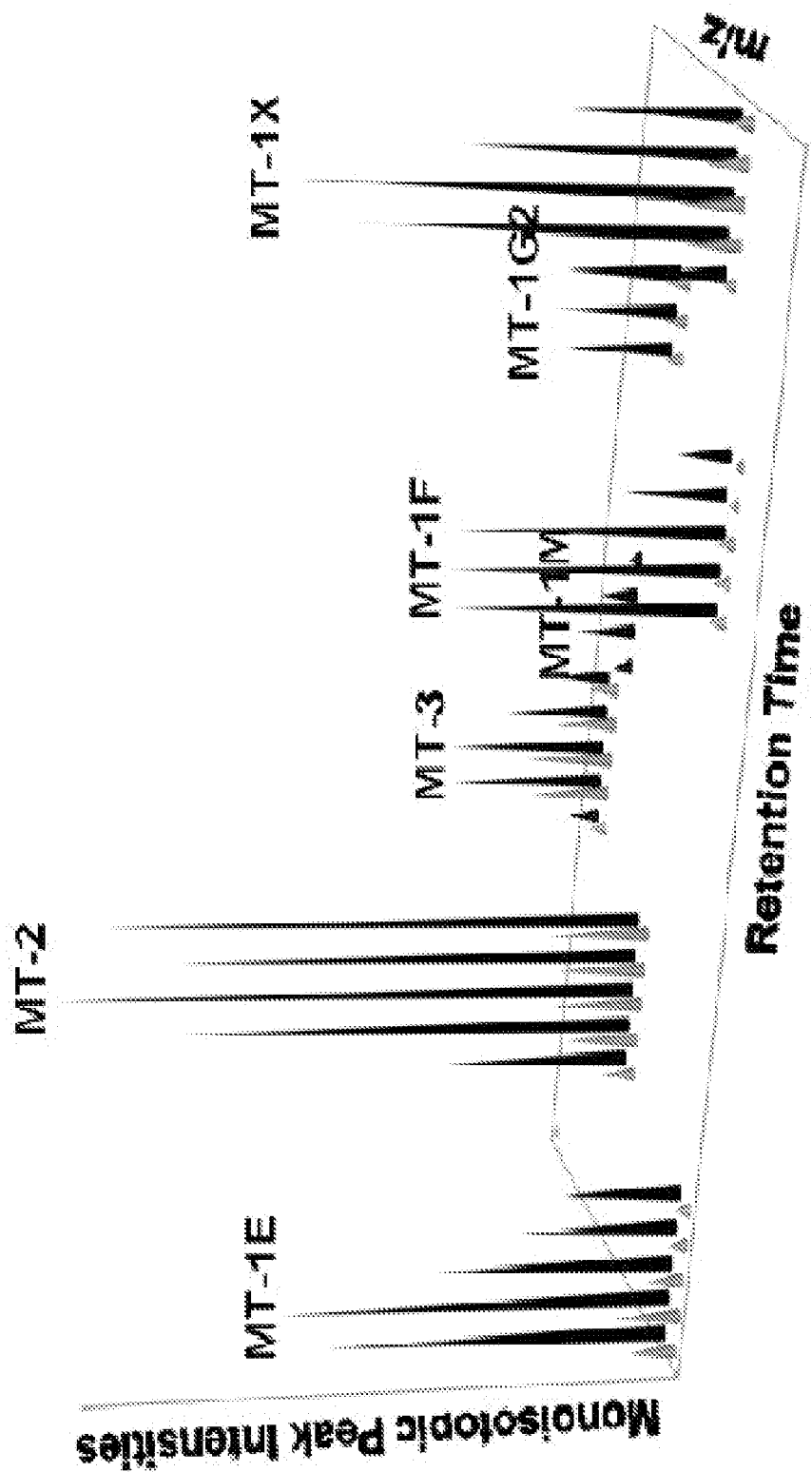
FIG. 3A-3B illustrates induction of metallothioneins in HK-2 MT-3 cells after three days of exposure to 9 µM Cd treatment.
Figure 3B:
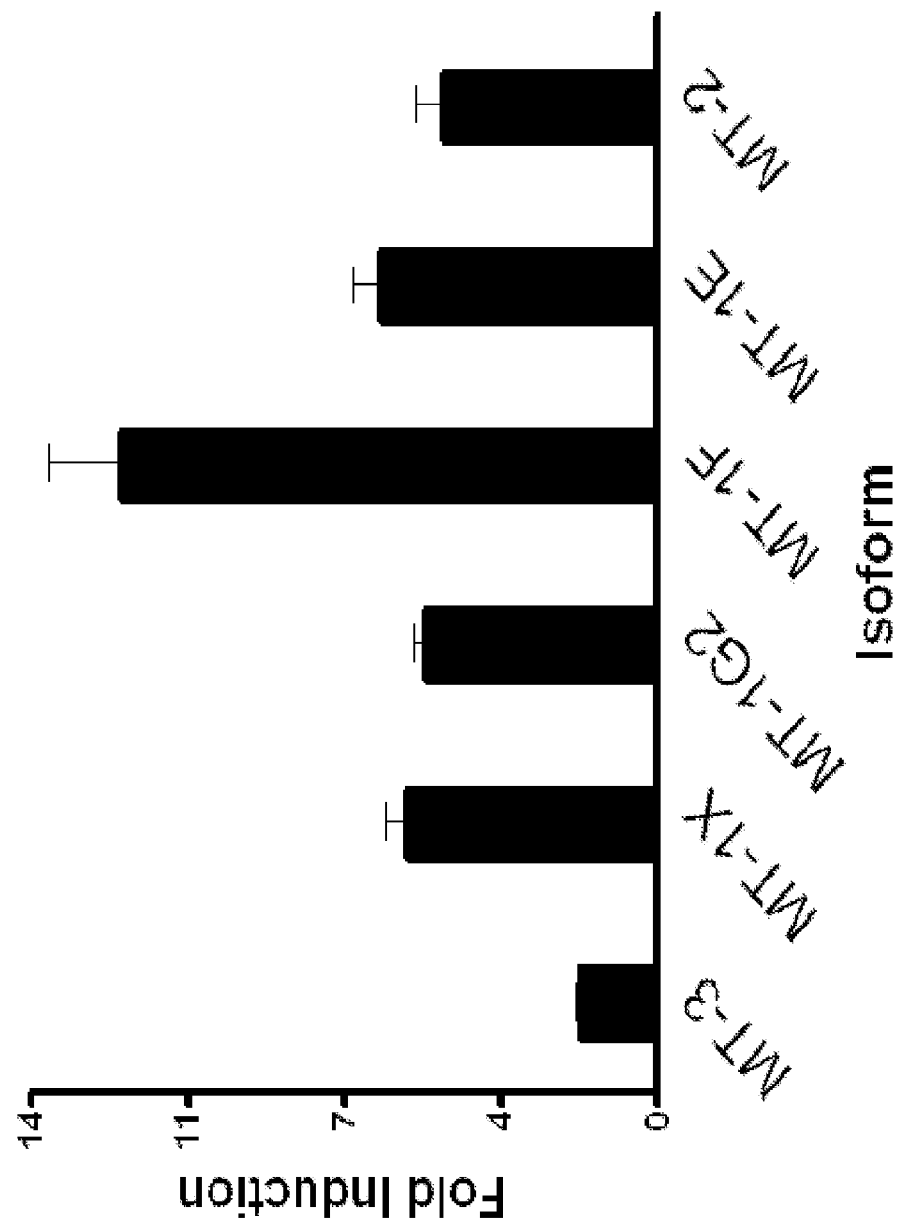

The sensitivity and dynamic range of the relative quantitation assay was determined next. A serial dilution of light cytosol was mixed with a constant amount of heavy cytosol and the samples were digested, fractionated and analyzed as before. A 1:1 correlation was observed for experimental vs. theoretical light/heavy MT2 ratio over two orders of magnitude (FIG. 2). The signal-to-noise ratio for these samples ranged from 3.24 to 109.33.

Quantitation of Metallothionein mRNA and Protein Expression in $Cd^{2+}$-Exposed HK-2 Cells.

Metallothioneins in the kidney, and in particular the proximal tubule epithelia, are highly responsive to $Cd^{2+}$ exposure. Consequently, there has been much effort to evaluate metallothioneins as potential biomarkers for heavy metal toxicity. The immortalized HK-2 human proximal epithelial cell line is a convenient model for studying proximal tubule cell function (Ryan et al., *Kidney Int* 45:48-57 (1994)). In contrast to human proximal tubule cells, HK-2 cells have lost expression of MT-3. Restoration of this gene causes the cells to dome and exhibit vectorial active transport similar to human proximal tubule (HPT) cells grown in culture (Kim et al., Kidney Int. 61: 464-472

(2002)). The mRNA expression of human proximal tubule cells have been qualitatively evaluated by reverse transcription PCR (Hoey et al., Toxicol Lett 92:149-160 (1997); Garrett et al., Environ Health Perspect 106:587-595 (1998)) and Northern blot analysis (Bylander et al., Toxicol Lett 71:111-122 (1994); Bylander et al., Toxicol Lett 76:209-217 (1995)). Combined, these studies paint a broad picture of metallothionein isoform mRNA expression of MT-3, MT-2A, MT-1A, MT-1E, MT-1F, and MT-1X, and possibly MT-1G. Of these, at least MT-1A, MT-1E are induced by $Cd^{2+}$ exposure. Protein expression is induced at least 30-fold upon three-day exposure to $Cd^{2+}$. However, prior protein determination methods could not distinguish between isoforms to ascertain which ones contribute to overall metallothionein protein levels.

Real-time quantitative PCR and the mass spectrometry-based metallothionein isoform assay described herein were used to quantitatively evaluate metallothionein mRNA and protein levels in HK-2 cells.

Figure 4A:
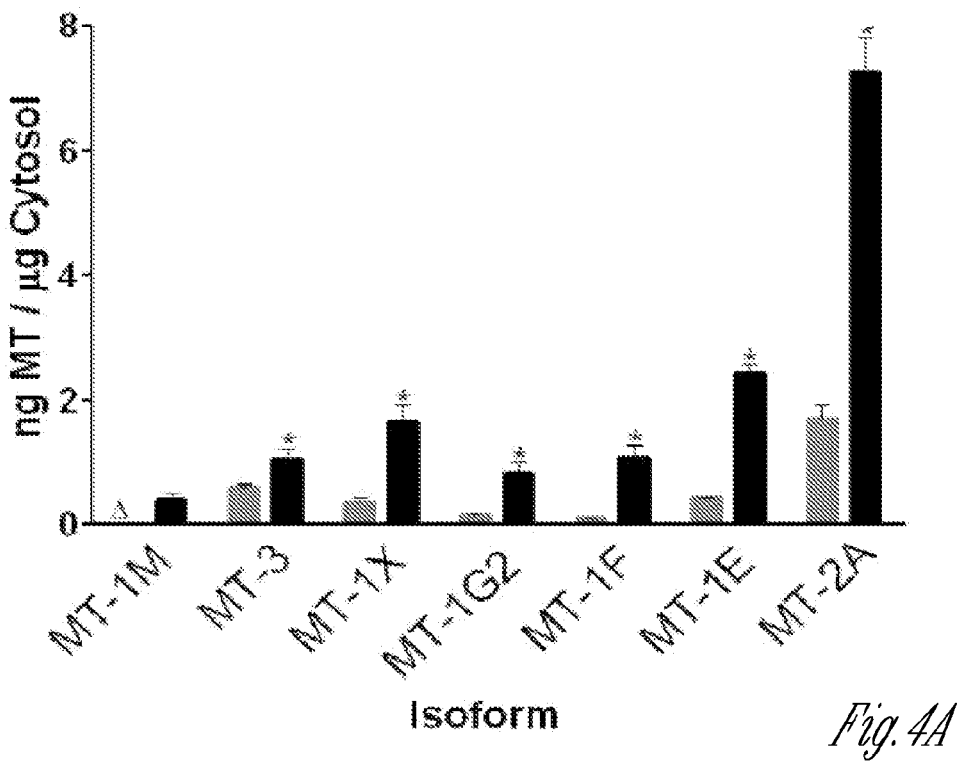
FIG. 4A-4B graphically illustrate the absolute levels of metallothionein protein and mRNA transcript levels three days after treatment of HK-2 MT-3 cells with 9 µM Cd.
Figure 4B:
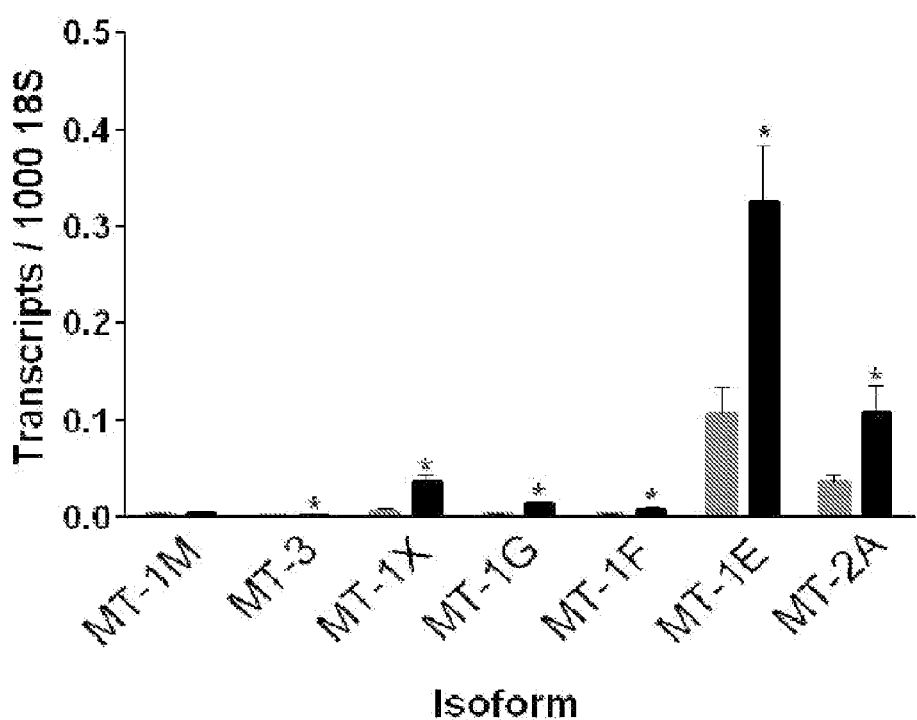

FIG. 4B shows the mRNA expression levels of human metallothionein isoforms in HK-2 MT-3 cells as determined by quantitative real-time PCR. Table 3 shows the absolute normalized mRNA levels for each metallothionein isoform detected in control and Cd-induced HK-2 MT-3 cells. The values shown are the average metallothionein transcripts/ 1000 18S rRNA ±S.D. and represent three biological replicates. Fold inductions were calculated by comparing levels of each MT isoform from Cd-treated cells to that of the metallothionein levels found in the control.

TABLE 3 mRNA Expression Levels

| | Control | Cd-treated | Fold Induction |
|---|---|---|---|
| MT-1M | 0.0021 ± .0006 | 0.0031 ± .0001 | 1.5 |
| MT-3 | 0.0013 ± .0002 | 0.0022 ± .0002 | 1.7 |
| MT-1X | 0.0069 ± .0023 | 0.0351 ± .0084 | 5.1 |
| MT-1G2 | 0.0027 ± .0003 | 0.0135 ± .0008 | 4.9 |
| MT-1F | 0.0027 ± .0004 | 0.0085 ± .0021 | 3.1 |
| MT-1E | 0.1078 ± .0259 | 0.3265 ± .0572 | 3.0 |
| MT-2 | 0.0352 ± .0091 | 0.1090 ± .0265 | 3.1 |

As shown in FIG. 4B MT1-E and MT-2A were the most abundant mRNA species detected in HK-2 MT-3 cells. These results are consistent with prior analyses of metallothionein mRNA expression in proximal human tubule cells with respect to MT1-E and MT-2A being the most abundant mRNA species. However, unlike previous studies, MT-1A was not observed in the quantitative real-time PCR performed as described herein. In addition, unlike previous studies, low levels of MT-1M mRNA were detected in uninduced cells.

However, MT-1M protein was not detected in uninduced HK-2 MT-3 cells (FIG. 4A), suggesting that MT-1M may be translated at levels below the threshold of detection. Moreover, the relative order of metallothionein isoform abundance differs when evaluating mRNA and protein expression. For example, MT1E is the most abundant mRNA while MT2 is the most abundant protein (compare FIGS. 4A and 4B). Cadmium-induced mRNA and protein levels were comparable for MT1G2, MT1X, MT2 and MT3, but protein induction was substantially greater than mRNA induction for MT1E and MT1F (Table 4).

TABLE 4

Comparison of Metallothionein mRNA and Protein Levels

| | Protein | | mRNA |
|---|---|---|---|
| Isoform | Absolute Fold Induction | Relative Fold Induction | Transcripts Fold Induction |
| MT-3 | 1.7 ± 0.1 | 1.8 ± 0.2 | 1.7 ± 0.1 |
| MT-1X | 5.6 ± 0.9 | 4.7 ± 1.8 | 5.1 ± 0.4 |
| MT-1G2 | 5.2 ± 0.5 | 5.4 ± 1.3 | 4.9 ± 0.6 |
| MT-1F | 12.0 ± 2.8 | 9.9 ± 1.9 | 3.1 ± 0.3 |
| MT-1E | 6.2 ± 1.1 | 5.9 ± 0.5 | 3.0 ± 0.4 |
| MT-2 | 4.8 ± 1.1 | 4.3 ± 0.9 | 3.1 ± 0.9 |

These results indicate that metallothionein isoforms may exhibit differential post-transcriptional mRNA stability, differential translation, or differential protein degradation upon metal induction.

MT Isoform Expression in HK-2 MT-3 Cells: Absolute Quantitation.

The $^{15}N$-labeled synthetic MT peptides described earlier were used as internal standards to determine the absolute amount of human MT isoforms in HK-2 MT-3 cells. A cocktail containing seven N-terminal MT peptides observed in HK-2 MT-3 cells was added to cytosols that had been alkylated with $^{14}N$-iodoacetamide. The spiked cytosols were then trypsin-digested and the N-terminal MT peptides were enriched and analyzed as above. Metallothionein isoforms were quantified for both control and Cd-induced cells. Table 5 provides absolute metallothionein protein levels for each isoform detected in control and Cd-induced HK-2 MT-3 cells. Fold inductions were calculated by comparing levels of each metallothionein isoform from Cd-treated cells to that of the metallothionein levels found in the control.

TABLE 5

Absolute Metallothionein Protein Levels

| | Control | Cd-treated | Fold Induction |
|---|---|---|---|
| MT-1M | Δ | 0.3757 ± .1257 | — |
| MT-3 | 0.6013 ± .0431 | 1.0544 ± .1550 | 1.8 |
| MT-1X | 0.3486 ± .0639 | 1.6396 ± .2841 | 4.7 |
| MT-1G2 | 0.1513 ± .0212 | 0.8253 ± .1717 | 5.5 |
| MT-1F | 0.1083 ± .0030 | 1.0742 ± .1912 | 9.9 |
| MT-1E | 0.4150 ± .0181 | 2.4364 ± .1187 | 5.9 |
| MT-2 | 1.6955 ± .2169 | 7.2757 ± .5457 | 4.3 |

The values in Table 5 are the average ng/μg±S.D. and represent three biological replicates. The symbol Δ indicates no isoform was detected.

The fold-induction values for individual metallothionein isoforms determined by the absolute method (Table 5) were comparable to those measured by the relative method (Table 4). The 300 μg of total cytosolic protein used for each experiment was equivalent to the cytosolic protein content of ~3.7×10$^6$ cells. Assuming a volume of 0.1 pL per cell, the intracellular concentration for the seven detected metallothionein isoforms ranged from 0.03 for MT-1F in uninduced cells to 2 mM for MT-2 in $Cd^{2+}$-induced cells (0.11 and 7.28 ng per μg total protein respectively). The six metallothioneins detected in the uninduced cells accounted for 0.33% of total protein whereas the seven metallothioneins detected in Cd-induced cells accounted for 1.46% of the total cytosolic protein.

Quantitation of Metallothionein Isoforms in Human Breast Epithelial Cancer Cells.

Previous studies have shown that the expression of metallothionein mRNA was limited to MT-2, MT-1E and MT-1X in human breast ductal epithelia and from spontaneously immortalized and cancer cell lines derived from human breast epithelia (Friedline et al. Am J Pathol 152: 23-27 (1998); Gurel et al., Toxicol Sci 85:906-915 (2005)). Cancer cell lines were further distinguished by the much higher expression of these isoforms in estrogen receptor-negative cells compared to estrogen receptor-positive cells (Friedline et al 1998). Antibody-based methods showed a similar increase in general MT1/2 protein expression. These mRNA and protein expression results were semi-quantitative. This cancer model system was selected as a test case to compare quantities of metallothionein isoform-specific mRNA and protein expression.

Figure 5A:
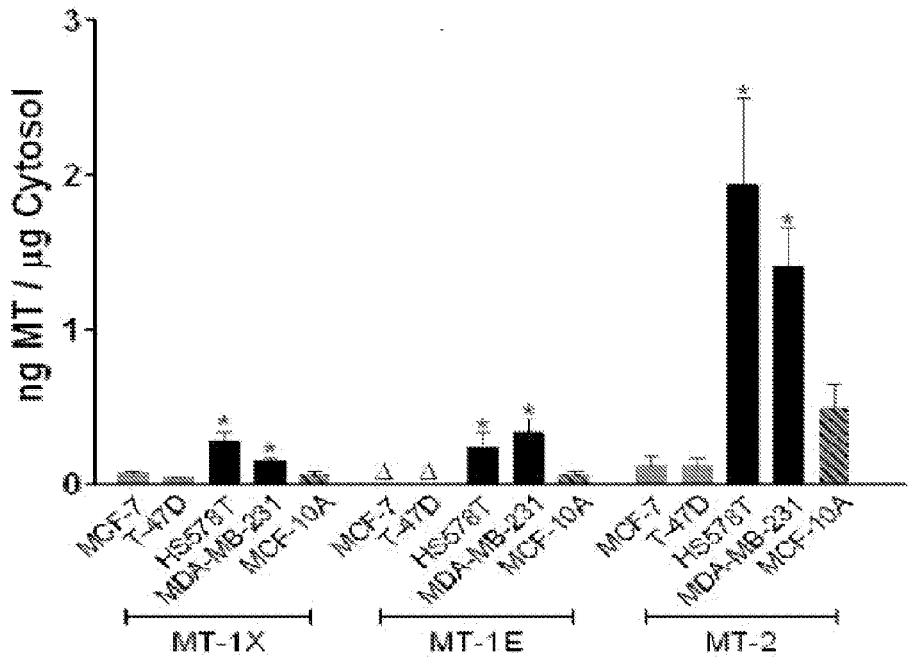
FIG. 5A-5B illustrates absolute protein and mRNA transcript levels of metallothioneins in malignant and non-malignant breast cells.
Figure 5B:
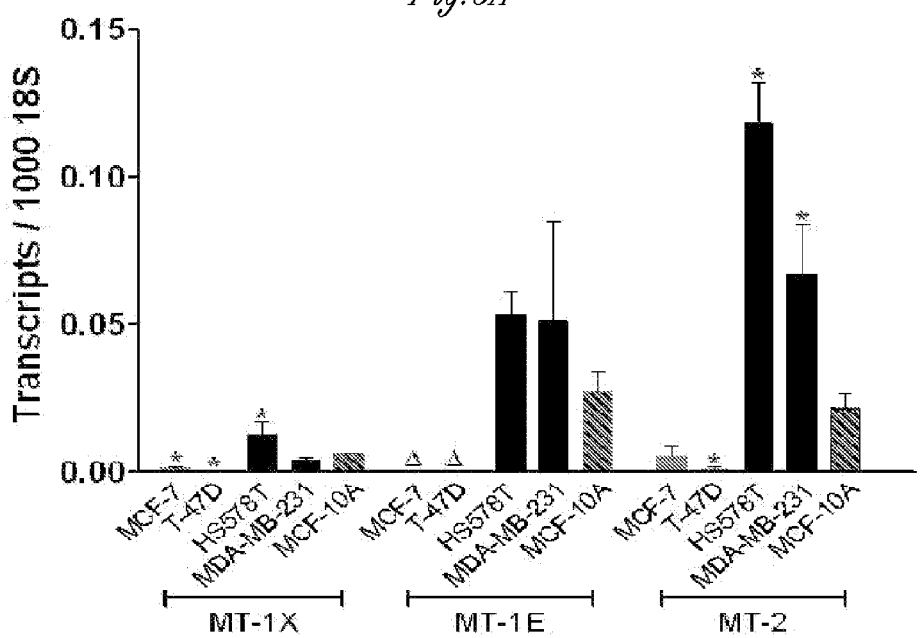
Figure 6A:
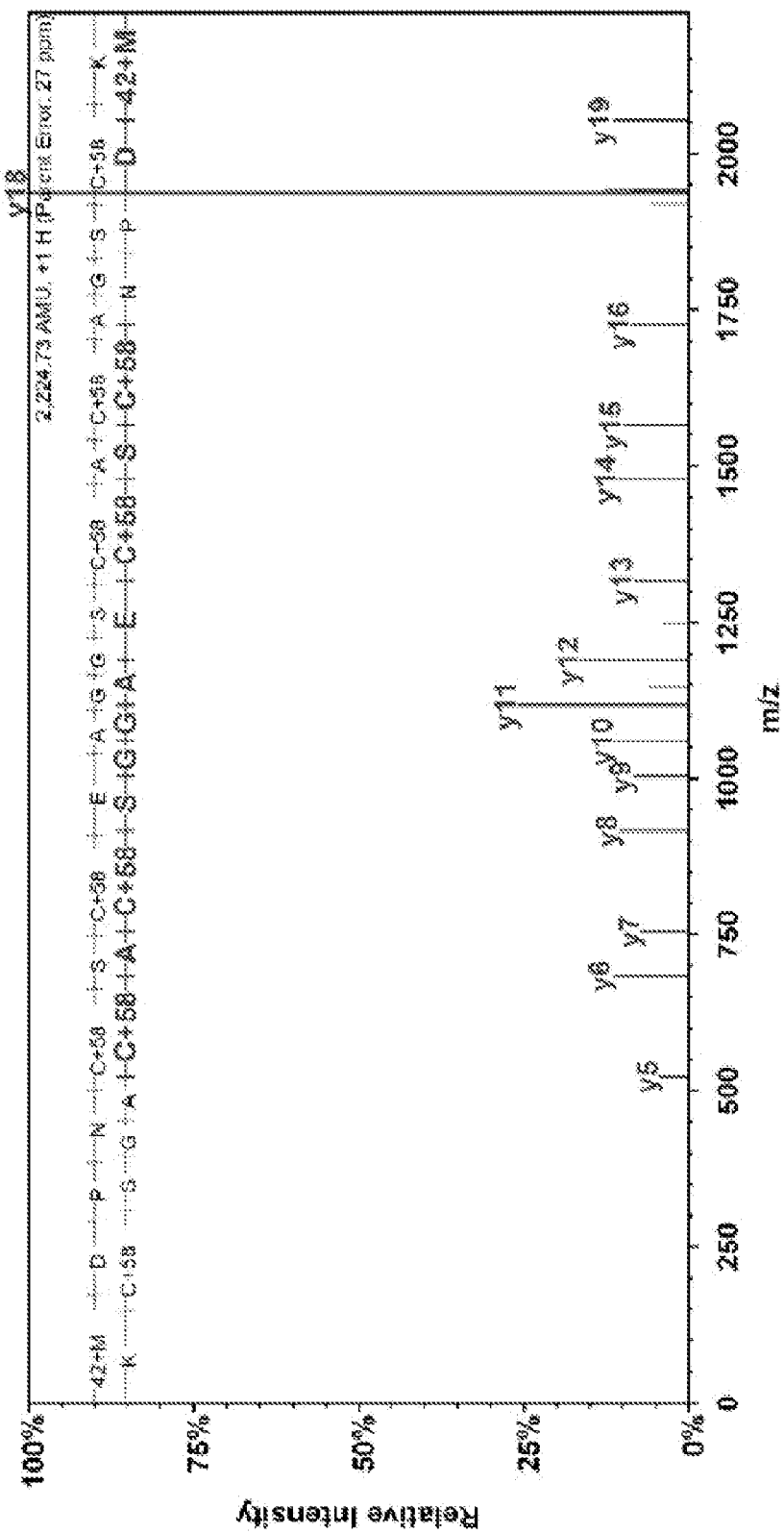

Quantitative real-time PCR showed that mRNA expression was limited to MT-2, MT-1E and MT-1X in the estrogen receptor-negative Hs-578T and MDA-MB-231 cancer cell lines and in the spontaneously immortalized non-tumorigenic MCF-10A cells (FIG. 5B, Table 6).

TABLE 6

Metallothionein mRNA Expression in Cancer Cells

| | MT-1X | Fold Change | MT-1E | Fold Change | MT-2A | Fold Change |
|---|---|---|---|---|---|---|
| MCF-7 | 0.0016 ± .0006 | 0.3 | Δ | — | 0.0058 ± .0030 | 0.3 |
| T-47 | 0.0003 ± .0002 | 0.1 | Δ | — | 0.0012 ± .0009 | 0.1 |
| HS578T | 0.0131 ± .0040 | 2.0 | 0.0535 ± .0075 | 2.0 | 0.1183 ± .0138 | 5.4 |
| 231 | 0.0044 ± .0009 | 0.7 | 0.0513 ± .0338 | 1.9 | 0.0670 ± .0170 | 3.0 |
| MCF-10A | 0.0065 ± .0002 | 1.0 | 0.0272 ± .0068 | 1.0 | 0.0220 ± .0048 | 1.0 |

Transcript levels in this study spanned a 400-fold dynamic range. However, only MT-2 mRNA and MT-1X mRNA were detected in estrogen receptor-positive MCF-7 and T47D cell lines. The estrogen receptor-negative cell lines had characteristically more metallothionein mRNA expression than their estrogen-receptor-positive counterparts. These general observations are consistent with the previously published qualitative data on the same cell lines (Friedline et al 1998; Gurel et al 2005).

Preliminary screening for N-terminal metallothionein peptides by mass spectrometry revealed the same metallothionein isoforms might be detected as protein as were detected as mRNA, including the restriction of MT-1E expression to estrogen receptor-negative cell lines. Hence, the MT-2, MT-1E, and MT-1X isoforms were quantified using $^{15}$N-labeled MT-2, MT-1E, and MT-1X peptides as internal standards (FIG. 5A, Table 7).

TABLE 7

Metallothionein Protein Expression in Cancer Cells

| | MT-1X | Fold Change | MT-1E | Fold Change | MT-2A | Fold Change |
|---|---|---|---|---|---|---|
| MCF-7 | 0.0754 ± .0079 | 1.1 | Δ | — | 0.1354 ± .0520 | 0.3 |
| T-47D | 0.0500 ± .0020 | 0.8 | Δ | — | 0.1350 ± .0409 | 0.3 |

TABLE 7-continued

Metallothionein Protein Expression in Cancer Cells

| | MT-1X | Fold Change | MT-1E | Fold Change | MT-2A | Fold Change |
|---|---|---|---|---|---|---|
| HS578T | 0.2888 ± .0564 | 4.4 | 0.2441 ± .1003 | 3.5 | 1.9436 ± .5578 | 3.9 |
| 231 | 0.1602 ± .0172 | 2.4 | 0.3387 ± .0956 | 4.8 | 1.4163 ± .2516 | 2.8 |
| MCF-10A | 0.0663 ± .0188 | 1.0 | 0.0707 ± .0130 | 1.0 | 0.5022 ± .1556 | 1.0 |

The dynamic range of individual metallothionein isoform expression was 38-fold. The dynamic range of total metallothionein isoform expression was 13-fold. This is seven times greater than the 1.8-fold dynamic range in MT-1/2 expression observed earlier with antibody-based methods (Friedline et al 1998).

Even though the dynamic range of protein expression is greatly increased with mass spectrometry-based quantitation, it is still much less than the mRNA dynamic range. This appears to be due primarily to the much lower protein-to-transcript ratio of MT-1E compared to either MT-1X or to MT-2A. Normalizing these ratios to MT-2A and taking the mean of ratios across all cell lines tested shows that the MT-1X ratio is comparable to that of MT-2A (1.4±0.23, n=5). In contrast, the relative translational efficiency of MT-1E is one-sixth that of MT-1X (0.23±0.09, n=3). The MT-1E isoform represents 30 to 50% of all metallothionein transcripts but only 10 to 18% of all MT protein in estrogen receptor-negative cell lines.

In conclusion, MT-1E is not translated into protein in estrogen-responsive cells, but is actively transcribed in estrogen receptor-negative cells. The expression efficiency of MT-1E protein relative to mRNA is therefore reduced relative to the two other metallothionein isoforms that are expressed in all breast cancer cell lines tested.

REFERENCES

1. Laukens D, Waeytens A, De Bleser, P, Cuvelier C, De Vos, Martin. (2009). Human metallothionein expression under normal and pathological conditions: mechanisms of gene regulation based on in silico promoter analysis. Crit Rev Eukary Gene Express 19:301-317.
2. Andrews G K. (2000). Regulation of metallothionein gene expression by oxidative stress and metal ions. Biochem Pharmacol 59:95-104.
3. Hamer D H. (1986). Metallothionein. Ann Rev Biochem 55:913-951.
4. Sakurai A, Hara S, Okano N, Kondo Y, Inoue J, Imura N. (1999). Regulatory role of metallothionein in NF-kappaB activation. FEBS Lett 455:55-58.
5. Kim C H, Kim J H, Lee J, Ahn Y S. (2003). Zinc-induced NF-kappaB inhibition can be modulated by changes in the intracellular metallothionein level. Toxicol Appl Pharmacol 190:189-196.
6. Ostrakhovitch E A, Olsson P E, Jiang S, Cherian M G. (2006). Interaction of metallothionein with tumor suppressor p53 protein. FEBS Left 580:1235-1238.
7. Zeng J, Heuchel R, Schaffner W, Kagi J H. (1991). Thionein (apometallothionein) can modulate DNA binding and transcriptional activation by zinc finger containing factor Sp1. FEBS Lett 279:310-312.
8. Schmidt C J, Jubier M F, Hamer D H. (1985). Structure and expression of two human metallothionein-I isoform genes and a related pseudogene. J Biol Chem 260:7731-7737.

9. Garrett S H, Sens M A, Todd J H, Somji S, Sens D A. (1999). Expression of MT-3 protein in the human kidney. Toxicol Lett 105:207-214.
10. Jasani B, Schmid K W. (1997). Significance of metallothionein overexpression in human tumours. Histopathology 31:211-214.
11. Theocharis S E, Margeli, A P, Klijanienko J T, Kouraklis G P. (2004). Metallothionein expression in human neoplasia. Histopathology 45:103-118.
12. Namdarghanbari M, Wobig W, Krezoski S, Tabatabai N M, Petering D H. (2011). Mammalian metallothionein in toxicology, cancer, and cancer chemotherapy. J Biol Inorgan Chem 16:1087-1101.
13. Midididoddi S, McGuirt J P, Sens M A, Todd J H, Sens D A (1996). Isoform-specific expression of metallothionein mRNA in the developing and adult human kidney. Toxicol Lett 85:17-27.
14. Arriaga J M, Levy E S, Bravo A I, Bayo S M, Amat M, Aris M, Hannois A, Bruno L, Roberti M P, Loria F S, Pairola A, Huertas E, Mordon J, Bianchini M. (2011). Metallothionein expression in colorectal cancer: relevance fo different isoforms for tumor progression and patient survivial. Human Pathol 43:197-208.
15. Wang R, Sens D A, Albrecht A, Garrett S, Somji S, Sens M A, and Lu X (2007) Simple method for identification for metallothionein isoforms in cultured human prostate cells by MALDI-TOF/TOF mass spectrometry. Anal Chem 79:4433-4441.
16. Huang I-Y, Kimura M, Hata A, Tsunoo H and Yoshida A (1981) Complete amino acid sequence of mouse liver metallothionein-II. J Biochem 89:1839-1845.
17. Huang I-Y, Yoshida A, Tsunoo H, and Nakajima H (1977) Mouse liver metallothioneins: comlete amino acid sequence of Metallothionein-I. J Biol Chem 252:8217-8221.
18. Kissling M M and Kägi J H R (1977) Primary structure of human hepatic metallothionein. FEBS Lett 82:274-250.
19. Kojima Y, Berger C, Vallee B L and Kägi J H R (1976) Amino acid sequence of equine renal metallothionein-1B. Proc Natl Acad Sci USA 73:3413-3417.
20. Winge D R, Nielson K B, Zeikus R D, and Gray W R (1984) Structural characterization of the isoforms of neonatal and adult rat liver metallothionein. J Biol Chem 259:11419-11425.
21. Boissel J-P, Kasper T, and Bunn H F (1988) Cotranslational amino-terminal processing of cytosolic proteins: cell-free expression of site-directed mutants of human hemoglobin. J Biol Chem 263:8443-8449.
22. Arnesen T, Van Damme P, Polevoda B, Helsens K, Evjenth R, Colaert N, Varhaug J E, Vandekerckhove J, Lillehaug J R, Sherman F, and Gevaert K (2009) Proteomics analyses reveal the evolutionary conservation and divergence of N-terminal acetyltransferases from yeast and humans. Proc Natl Acad Sci USA 106:8157-8162.
23. Helbig A O, Gauci S, Raijmakers R, van Breukelen B, Slijper M, Mohammed S, and Heck A J R (2010) Profiling of N-acetylated protein termini provides in-depth insights into the N-terminal nature of the proteome. Mol Cell Proteomics 9:928-939.
24. Knudsen C B, Bjornsdottir I, Jons O, and Hansen S H (1998) Detection of metallothionein isoforms from three different species using on-line capillary electrophoresis-mass spectrometry. Anal Biochem 265:167-175.
25. Beattie J H, Wood A M, and Duncan G J (1999) Rat metallothionein-2 contains N-acetylated and unacetylated forms. Electrophoresis 20:1613-1618.
26. Van Vyncht G, Bordin A and Rodriguez A R (2000) Rabbit liver metallothionein subisoform characterization using liquid chromatography hyphenated to diode array detection and electrospray ionization mass spectrometry. Chromatographia 52:745-752.
27. Andón B, Barbosa J, Sanz-Nebot V (2006) Separation and characterization of rabbit liver apothioneins by capillary electrophoresis coupled to electrospray ionization time-of-flight mass spectrometry. Electrophoresis 27:3661-3670.
28. Ray W J and Koshland D E (1962) Identification of amino acids involved in phosphoglucomutase action. J Biol Chem 237:2493-2505.
29. Savige W E and Fontana A (1977) Interconversion of methionine and methionine sulfoxide. Meth Enzymol 47:453-459.
30. Gross E (1967) The cyanogen bromide reaction. Meth Enzymol 11:238-255.
31. Alvarez L, Gonzalez-Iglesias H, Garcia M, Ghosh S, Sanz-Medel A, and Coca-Prados M (2012) The stoichiometric transition from $Zn_6Cu_1$-metallothionein to $Zn_7$-metallothionein underlies the up-regulation of metallothionein (MT) expression: quantitative analysis of MT-metal load in eye cells. J Biol Chem 287:28456-28469.
32. Mounicou S, Ouerdane L, L'Azou B, Passagne I, Ohayon-Courtes C, Szpunar J, and Lobinski R (2010) Identification of metallothionein subisoforms in HPLC using accurate mass and online sequencing by electrospray hybrid linear ion trap-orbital ion trap mass spectrometry. Anal Chem 82:6947-6957.
33. Desiere F, Deutsch E W, Nesvizhskii A I, Mallick P, King N L, Eng J K, Adereem A, Boyle R, Brunner E, Donohoe S, Fausto N, Hafen E, Hood L, Katze M G, Kennedy K A, Kregenow F, Lee, H, Lin B, Martin D, Ranish J A, Rawlings D J, Samelson L E, Shiio Y, Watts J D, Wollscheid B, Wright M E, Yan W, Yang L, Yi E C, Zhang H, and Aebersold R (2004) Integration with the human genome of peptide sequences obtained by high-throughput mass spectrometry. Genome Biol 6:R9.
34. Desiere F, Deutsch E W, King N L, Nescishskii A I, Mallick P, Eng J, Chen S, Eddes J, Loevenich S N and Aebersold R (2006) The PeptideAtlas project. Nucl Acids Res 34:D655-D658.
35. Beck M, Schmidt A, Malmstroem J, Claasen M, Ori A, Szymborska A, Herzog F, Rinner O, Ellenberg J, and Aebersold R (2011) The quantitative proteome of a human cell line. Mol Syst Biol 7:549.
36. Geiger T, Wehner A, Schaab C, Cox J, and Mann M (2012) Comparative proteomic analysis of eleven common cell lines reveals ubiquitous but varying expression of most proteins. Mol Cell Proteomics 11:1-11.
37. Munoz J, Low T Y, Kok Y J, Chin A, Frese C K, Ding V, Choo A, and Heck A J R (2011) The quantitative proteomes of human induced pluripotent stem cells and embryonic stem cells. Mol Syst Biol 7:550.
38. Nagaraj N, Wisniewski J R, Geiger T, Cox J, Kircher M, Kelso J, Pääbo S, and Mann M (2011) Deep proteome and transcriptome mapping of a human cancer cell line. Mol Syst Biol 7:548.
39. Phanstiel D H, Brumbaugh J, Wenger C D, Tian S, Probasco M D, Bailey D J, Swaney D L, Tervo M A, Bolin J M, Ruotti V, Stewart R, Thomson J A, and Coon J J (2011) Phosphoproteomic comparison of human ES and iPS cells. Nat Meth 8:821-827.
40. Gevaert, K., Goethals, M., Martens, L., Van Damme, J., Staes, A., Thomas, G. R. and Vandekerckhove, J. (2003)

Exploring proteomes and analyzing protein processing by mass spectrometric identification of sorted N-terminal peptides. *Nat. Biotechnol* 21, 566-569.
41. Sechi, S., Chait, B. T. (1998) Modification of cysteine residues by alkylation. A tool in peptide mapping and protein identification. *Anal. Chem* 70, 5150-5158.
42. Gygi S P, Rist B, Gerber S A, Turecek F, Gelb M H, Aebersold R. (1999) Quantitative analysis of complex protein mixtures using isotope-coded affinity tags. *Nat. Biotechnol* 17:994-999.
43. Niwayama S, Kurono S, and Matsumoto H (2001) Synthesis of d-labeled N-alkylamaleimides and application to quantitative peptide analysis by isotope differential mass spectrometry. *Bioorg Med Chem Lett* 13:2913-2916.
44. Niwayama S, Kurono S, and Matsumoto H (2003) Synthesis of $^{13}$C-labeled iodoacetanilide and application to quantitative peptide analysis by isotope differential mass spectrometry. *Bioorg Med Chem Lett* 11:2257-2261.
45. Sebastiano R, Citterio A, Lapadula M, and Righetti P G (2003) A new deuterated alkylating agent for quantitative proteomics. *Rapid Commun Mass Spec* 17:2380-2386.
46. Shen M, Guo L, Wallace A, Fitzner J, Eisenman J, Jacobson E, and Johnson R S (2003) Isolation and isotope labeling of cysteine- and methionine-containing tryptic peptides. *Mol Cell Proteomics* 2:315-324.
47. Pasquarello C, Sanchez J-C, Hochstraser D F, and Corthals G L (2004) N-t-butyliodoacetamide and iodoacetanilide: two new cysteine alkylating reagents for relative quantitation of proteins. *Rapid Commun Mass Spec* 18:117-127.
48. Niwayama S, Kurono S, Cho H, and Matsumoto H (2006) Synthesis of D-labeled naphthyliodoacetamide and application to quantitative peptide analysis by isotope differential mass spectrometry. *Bioorg Med Chem Lett* 16:6054-6057.49. Zhang R and Regnier F E (2002) Minimizing resolution of isotopically coded peptides in comparative proteomics. *J Proteome Res* 1:139-147.
50. Conrads T P, Alving K, Weenstra T D, Belov M E, Anderson G A, Anderson D J, Lipton M S, Paša-Tolić L, Udseth H R, Chrisler W B, Thrall B D, and Smith R D (2001) Quantitative analysis of bacterial and mammalian proteomes using a combination of cysteine affinity tags and $^{15}$N-metabolic labeling. *Anal Chem* 73:2132-2139.
51. Kim, D., Garrett, S. H., Sens, M. A., Somji, S., and Sens, D. A. (2002). Metallothionein isoform 3 and proximal tubule vectorial active transport. *Kidney Int.* 61, 464-472.
52. Somji, S., Garrett, S. H., Sens, M. A., Gurel, V., and Sens, D. A. (2004). Expression of metallothionein isoform 3 (MT-3) determines the choice between apoptotic or necrotic cell death in $Cd^{+2}$-exposed human proximal tubule cells. *Toxicol. Sci.* 80, 358-366.
53. Shechter Y (1986) Selective oxidation and reduction of methionine residues in peptides and proteins by oxygen exchange between sulfoxide and sulfide. *J Biol Chem* 261:66-70.
54. Dormeyer W, Mohammed S, van Breukelen B, Krijgsveld J, and Heck A J R (2007) Targeted analysis of protein termini. *J Proteome Res* 6:4634-4645.
55. Landon M (1977) Cleavage at aspartyl-prolyl bonds. *Meth Enzymol* 47:145-149.
56. Ghesquiére B, Jonkheere V, Colaert N, Van Durme J, Timmerman E, Goethals M, Schymkowitz J, Rousseau F, Vandekerchkove J, and Gevaert K (2011) Redox proteomics of protein-bound methionine oxidation. *Molec Cell Proteomics* 10:1-12.
57. Lipton S H and Bodwell C E (1976) Specific oxidation of methionine to methionine sulfoxide. *J Agric Food Chem* 24:26-31.
58. Cousins R J (1979) Metallothionein synthesis and degradation: relationship to cadmium metabolism. *Environ Health Persp* 28: 131-136.
59. Monia, B P., Butt, T R., Ecker, D J., Mirabelli, C K., Crooke, S T. (1986) Metallothionein turnover in mammalian cells. *J Biol Chem* 24:10957-10959.
60. Winge, D. R., Miklossy, K. A. (1982) Domain nature of metallothionein. *J. Biol. Chem.* 257, 3471-3476.
61. Nielson, K. B., Winge, D. R. (1983) Order of metal binding in metallothionein. *J. Biol. Chem.* 258, 13063-13069.
62. Nielson, K. B., Atkin, C. L., Winge, D. R. (1985) Distinct metal-binding configurations in metallothionein. *J. Biol. Chem.* 1985, 260, 5342-5350.
63. Friedline J A, Garrett S H, Somji S, Todd J H, and Sens D A (1998) Differential expression of the MT-1E gene in estrogen-receptor-positive and -negative human breast cancer cell lines. Am J Pathol 152:23-27.
64. Gurel V, Sens D A, Somji S, Garrett S H, Weiland T, and Sens M A (2005) Post-transcriptional regulation of metallothionein isoform 1 and 2 expression in the human breast and the MCF-10A cell line. *Toxicol Sci* 85:906-915.
65. Ryan M J, Johnson G, Kirk J, Fuerstenberg, Zager R A, and Torok-Storb B (1994) HK-2: An immortalized proximal tubule epithelial cell line from normal adult human kidney. *Kidney Int* 45:48-57.
66. Detrisac C J, Sens M A, Garvin A J, Spicer S S, and Sens D A (1984) Tissue culture of human kidney epithelial cells of proximal tubule origin. *Kidney Int* 25:383-390.
67. Bylander J E, Li S L, Sens M A, Hazen-Martin D, Re G G, and Sens D A (1994) Induction of metallothionein mRNA and protein following exposure of cultured human proximal tubule cells to cadmium. Toxicol Lett 71:111-122.
68. Bylander J E, Li SLm Sens M A, and Sens D A (1995) Exposure of human proximal tubule cells to cytotoxic levels of CdCl2 induces the additional expression of metallothionein 1A mRNA. Toxicol Lett 76:209-217.
69. Garrett S H, Somji S, Todd J H, and Sens D A (1998) Exposure of human proximal tubule cells to Cd2+, Zn2+, and Cu2+ induces metallothionein protein accumulation but not metallothionein. Environ Health Perspect 106: 587-595.
70. Garrett S H, Somji S, Todd J H, Sens M A, and Sens D A (1998) Differential expression of human metallothionein isoform I mRNA in human proximal tubule cells exposed to metals. Environ Health Perspec 106:825-832.
71. Hoey J G, Garrett S H, Sens M A, Todd J H, and Sens D A (1997) Expression of MT-3 mRNA in human kidney, proximal tubule cell cultures, and renal cell carcinoma. Toxicol Lett 92:149-160.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods, molecules and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention.

The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "an isomer" or "a method" or "a disease" includes a plurality of such isomers, methods or diseases, and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The following statements describe some of the elements or features of the invention.

Statements:
1. A method comprising quantifying an amount of a metallothionein isomer peptide in a test sample by mass spectroscopy, wherein the metallothionein isomer peptide is an N-terminal peptide from cleavage of a metallothionein protein isomer selected from the group consisting of metallothionein-1A, metallothionein-1B, metallothionein-1E, metallothionein-1F, metallothionein-1G1, metallothionein-1G2, metallothionein-1H, metallothionein-1L, metallothionein-1M, metallothionein-1X, metallothionein-2, metallothionein-3, and metallothionein-4.
2. The method of statement 1, wherein the test sample is a tissue sample, cell sample, biological fluid sample, tissue biopsy, cultured cell sample, fixed tissue sample, fixed cell sample, or a combination thereof
3. The method of statement 1 or 2, wherein the test sample is whole blood, bone marrow, blood serum, blood plasma, buffy coat preparations, saliva, cerebrospinal fluid, cellular cytosol, urine, sweat, tears, feces, saliva, seminal plasma, nipple aspirate fluid, nipple discharge, pancreatic juice, or a combination thereof
4. The method of any of statements 1-3, wherein the test sample is a fresh, formalin fixed, frozen or lyophilized sample.
5. The method of any of statements 1-4, wherein proteins in the test sample are denatured before quantifying the amount of a metallothionein isomer peptide in the test sample.
6. The method of any of statements 1-5, wherein proteins in the test sample are denatured with a chaotropic agent before quantifying the amount of a metallothionein isomer peptide in the test sample.
7. The method of any of statements 1-6, wherein proteins in the test sample are denatured with a denaturant selected from the group consisting of urea, a guanidinium salt, an ammonium salt, a lithium salt, a cesium salt, a rubidium salt, a potassium salt, an iodide salt, and any combination thereof, before quantifying the amount of a metallothionein isomer peptide in the test sample.
8. The method of any of statements 1-7, wherein the test sample, or at least one protein from the test sample, is mixed with a reducing agent before quantifying the amount of a metallothionein isomer peptide in the test sample.
9. The method of any of statements 1-8, wherein the test sample, or at least one protein from the test sample, is mixed with a reducing agent selected from the group consisting of dithiothreitol, 2-mercaptoethanol, tris(2-carboxyethyl)phosphine, and any combination thereof, before quantifying the amount of a metallothionein isomer peptide in the test sample.
10. The method of any of statements 1-9, wherein the test sample, or at least one protein from the test sample, is alkylated with an alkylating agent before quantifying the amount of a metallothionein isomer peptide in the test sample.
11. The method of any of statements 1-10, wherein the test sample, or at least one protein from the test sample, is alkylated with an alkylating agent selected from the group consisting of iodoacetamide, iodoacetic acid and a combination thereof, before quantifying the amount of a metallothionein isomer peptide in the test sample.
12. The method of any of statements 1-11, wherein the test sample, or at least one protein from the test sample, is labeled, before quantifying the amount of a metallothionein isomer peptide in the test sample.
13. The method of any of statements 1-12, wherein the test sample, or at least one protein from the test sample, is labeled with a label that shifts the mass of the metallothionein isomer peptide by 1 to 10 daltons per cysteine, or by 1 to 5 daltons per cysteine, or by 1 to 4 daltons per cysteine, or by 1 to 3 daltons per cysteine, or by 1 to 2 daltons per cysteine before quantifying the amount of a metallothionein isomer peptide in the test sample.

14. The method of any of statements 1-13, wherein the test sample, or at least one protein from the test sample, is labeled with a stable isotope selected from the group consisting of $^{13}C$, $^{15}N$, and deuterium, before quantifying the amount of a metallothionein isomer peptide in the test sample.

15. The method of any of statements 1-14, wherein the test sample, or at least one protein from the test sample, is labeled with $^{15}N$, before quantifying the amount of a metallothionein isomer peptide in the test sample.

16. The method of any of statements 1-15, wherein the test sample, or at least one protein from the test sample, is cleaved, before quantifying the amount of a metallothionein isomer peptide in the test sample.

17. The method of any of statements 1-16, wherein the test sample, or at least one protein from the test sample, is cleaved to generate one or more metallothionein isomer peptides, before quantifying the amount of a metallothionein isomer peptide in the test sample.

18. The method of any of statements 1-17, wherein the test sample, or at least one protein from the test sample, is cleaved with an agent selected from the group consisting of trypsin, Lys-C, Lys-N, Glu-C, chymotrypsin, pepsin, thermolysin, papain, Arg-C, Asp-N and cyanogen bromide, to generate one or more metallothionein isomer peptides, before quantifying the amount of a metallothionein isomer peptide in the test sample.

19. The method of any of statements 1-18, wherein the test sample, or at least one protein from the test sample, is cleaved with trypsin, to generate one or more metallothionein isomer peptides, before quantifying the amount of a metallothionein isomer peptide in the test sample.

20. The method of any of statements 1-19, wherein the test sample, or at least one protein or metallothionein isomer peptide from the test sample, is separated from an impurity, before quantifying the amount of a metallothionein isomer peptide in the test sample.

21. The method of any of statements 1-20, wherein the test sample, or at least one protein or metallothionein isomer peptide from the test sample, is separated from an impurity by high pressure liquid chromatography, gel filtration, ion exchange chromatography, affinity chromatography, hydrophobic interaction chromatography, reversed phase chromatography, or a combination thereof, before quantifying the amount of a metallothionein isomer peptide in the test sample.

22. The method of any of statements 1-21, wherein the test sample, or at least one protein or metallothionein isomer peptide from the test sample, is separated from an impurity by high pressure liquid chromatography, ion exchange chromatography, reversed phase chromatography, or a combination thereof, before quantifying the amount of a metallothionein isomer peptide in the test sample.

23. The method of any of statements 1-22, wherein the metallothionein isomer peptide has a sequence selected from any of SEQ ID NO:18-29.

24. The method of any of statements 1-23, wherein the metallothionein isomer peptide is an alkylated peptide, where the peptide portion has a sequence selected from any of SEQ ID NO:18-29.

25. The method of any of statements 1-24, wherein quantifying the amount of a metallothionein isomer peptide in a test sample comprises comparing the metallothionein isomer peptide mass spectrum peak height or size with a control or standard peak height or size.

26. The method of any of statements 1-25, wherein quantifying the amount of a metallothionein isomer peptide in a test sample comprises comparing the metallothionein isomer peptide mass spectrum peak height or size with an unlabeled control peak height or size.

27. The method of any of statements 1-26, wherein quantifying the amount of a metallothionein isomer peptide in a test sample comprises comparing the metallothionein isomer peptide mass spectrum peak height or size with a labeled control peak height or size.

28. The method of any of statements 1-27, further comprising subjecting a control sample to each step performed on the test sample.

29. The method of any of statements 1-28, further comprising subjecting proteins or peptides from a control sample to each step performed on the test sample, or to each step performed on proteins or metallothionein isomer peptides from the test sample.

30. The method of any of statements 1-25, wherein a known amount of a detectable standard is added to the test sample.

31. The method of any of statements 1-25 or 30, wherein quantifying the amount of a metallothionein isomer peptide in a test sample comprises comparing a labeled metallothionein isomer peptide mass spectrum peak height or size with an unlabeled standard peak height or size.

32. The method of any of statements 1-25 or 30, wherein quantifying the amount of a metallothionein isomer peptide in a test sample comprises comparing the metallothionein isomer peptide mass spectrum peak height or size with a labeled standard peak height or size.

33. The method of any of statements 1-32, wherein the amount of more than one metallothionein isomer peptide is quantified.

34. The method of any of statements 1-33, wherein the amounts of two or more metallothionein isomer peptides are simultaneously quantified.

35. The method of any of statements 1-34, wherein the amount of more than one metallothionein protein isomer in the test sample is about 0.05 ng to 10 ng per µg total protein in the test sample.

36. The method of any of statements 1-35, which can quantify as little as 0.05 ng to 2 ng metallothionein protein isomer per µg total protein in the test sample.

37. A method comprising:
 a. alkylating peptide cysteine residues in a test mixture of peptides with an alkylating agent, after reduction of the peptides' disulfide bonds and/or the peptides' oxidized sulfhydryls, to generate alkylated metallothionein isomeric peptides in a mixture of alkylated mixture of peptides;
 b. enriching the alkylated metallothionein isomeric peptides in the alkylated mixture of peptides by removal of undesired peptides to generate an enriched pool of alkylated metallothionein isomeric peptides;

c. quantifying one or more alkylated metallothionein isomeric peptides in the enriched pool of metallothionein isomer peptides by mass spectrometric determination;

wherein the one or more alkylated metallothionein isomeric peptides is an N-terminal peptide from cleavage of an alkylated metallothionein protein isomer selected from the group consisting of metallothionein-1A, metallothionein-1B, metallothionein-1E, metallothionein-1F, metallothionein-1G1, metallothionein-1G2, metallothionein-1H, metallothionein-1L, metallothionein-1M, metallothionein-1X, metallothionein-2, metallothionein-3, metallothionein-4, and a combination thereof 38. The method of statement 37, wherein the alkylating agent is selected from the group consisting of iodoacetamide, iodoacetic acid and a combination thereof 39. The method of any of statements 37-38, wherein removal of undesired peptides comprises ion exchange matrix and/or reverse phase chromatography.

40. The method of any of statements 37-39, wherein removal of undesired peptides comprises retention and/or elution from a strong cation exchange matrix.

41. The method of any of statements 37-40, wherein removal of undesired peptides comprises retention and/or elution from reverse phase chromatography matrix.

42. The method of statement 37 or 38, further comprising labeling peptides during step a.

43. The method of any of statements 37-42, wherein the alkylating agent also labels peptide cysteine residues with a label.

44. The method of any of statements 37-41, further comprising quantifying a labeled standard peptide in step c, where the labeled standard peptide is present in the test mixture of peptides of step a.

45. A method comprising:
a. mass spectroscopy quantification of one or more metallothionein isomeric peptides in a test sample obtained from a subject, to determine a quantified amount of at least one metallothionein protein isomer in the test sample;
b. comparing the quantified amount of at least one metallothionein protein isomer to a healthy control amount of that type of metallothionein protein isomer to determine whether the subject has a disease;
wherein each of the one or more metallothionein isomeric peptides is an N-terminal peptide from cleavage of a metallothionein isomer selected from the group consisting of metallothionein-1A, metallothionein-1B, metallothionein-1E, metallothionein-1F, metallothionein-1G1, metallothionein-1G2, metallothionein-1H, metallothionein-1L, metallothionein-1M, metallothionein-1X, metallothionein-2, metallothionein-3, metallothionein-4, and a combination thereof 46. The method of statement 45, further comprising treating the disease when the quantified amount of metallothionein protein isomer is significantly different from the healthy control amount of that type of metallothionein protein isomer.

47. The method of statement 45 or 46, further comprising treating the disease when the quantified amount of metallothionein protein isomer is at least 10%, or at least 20%, or at least 30%, or at least 40%, or at least 50%, or at least 60%, or at least 70%, or at least 80%, or at least 90% different from the healthy control amount of that type of metallothionein protein isomer.

48. The method of any of statements 45-47, further comprising treating the disease when the quantified amount of metallothionein protein isomer is at least 2-fold, or at least 5-fold different from the healthy control amount of that type of metallothionein protein isomer.

49. The method of any of statements 45-48, wherein the test sample is a tissue sample, cell sample, biological fluid sample, tissue biopsy, cultured cell sample, fixed tissue sample, fixed cell sample, or a combination thereof; and the healthy control is of the same tissue or cell type.

50. The method of any of statements 45-49, wherein the disease is cancer or heavy metal poisoning.

51. The method of any of statements 45-50, wherein the disease is an invasive or metastatic cancer.

52. method of any of statements 45-51, wherein the disease is a breast cancer, colon cancer, lung cancer, prostate cancer, ovarian cancer, bladder cancer, ductal carcinoma, nasopharyngeal carcinoma, colorectal cancer, thyroid carcinoma, hepatocellular carcinoma, leukemia, lymphoma, melanoma, fibrosarcoma, neuroblastoma, autoimmune deficiency syndrome-associated Kaposi's sarcoma, adrenal cortex cancer, pheochromocytoma, cervical cancer, endometrial cancer, esophageal cancer, liver cancer, pancreatic cancer, prostate cancer, thymus cancer, chronic lymphocytic leukemia, Ewing's sarcoma, gestational trophoblastic tumor, hepatoblastoma, multiple myeloma, non-small cell lung cancer, retinoblastoma, or bone cancer.

53. The method of any of statements 37-52, which can identify and quantify as little as 0.05 ng to 2 ng metallothionein protein isomer per µg total protein in the test sample.

54. A kit comprising (a) one or more components, each component comprising one or more reagents for detecting and/or quantifying metallothionein protein isomers, and (b) instructions for using the kit and its components.

55. The kit of statement 54, comprising one or more components selected from one or more components for processing tissues or cells, one or more components for preparing the proteins in a test sample for analysis, and/or one or more components containing a reference peptide or a standard peptide.

56. The kit of statement 54 or 55, wherein the one or more components for processing tissues or cells are selected from tissue or cell stabilizing agents, protease inhibitors, protein denaturing agents (or a mixture of agents for denaturing proteins), reducing agents, buffers, diluents, small spin columns for removal of undesired materials from test samples, or a combination thereof 57. The kit of any of statements 54-56, wherein the one or more components for preparing the proteins in a test sample for analysis are selected from one or more reducing agents, one or more alkylating agents, one or more labeling agents, one or more proteases, one or more small spin columns for removal of undesired impurities, one or more small spin columns for enrichment of metallothionein proteins or peptides, one or more buffers for separation and/or enrichment of metallothionein peptides, one or more chromatography matrices, one or more chromatography columns, and combinations thereof.

58. The kit of any of statements 54-57, wherein the one or more components comprise one or more reference peptides or one or more standard peptides.
59. The kit of any of statements 54-58, wherein the one or more components comprise one or more reference peptides or one or more standard peptides, and at least one reference peptide or at least one standard peptide is labeled.
60. The kit of any of statements 54-59, wherein the one or more components comprise one or more reference peptides or one or more standard peptides, and each reference peptide or standard peptide is provided at a specified concentration (e.g., in solution) or as a specified amount (e.g., in dry form).
61. The kit of any of statements 54-59, wherein the instructions provide information for performing any the methods of statements 1-56.
62. The kit of any of statements 54-61, wherein the instructions provide information for performing test sample isolation, protein denaturation, reduction, alkylation, labeling, protease digestion, peptide separation, metallothionein peptide enrichment, quantitative mass spectrometry, use of reference or standard peptides, and combinations of such steps.
63. The kit of any of statements 54-62, wherein the instructions provide information for identifying or distinguishing one or more metallothionein protein or one or more peptide isomer from another.
64. The kit of any of statements 54-63, wherein the instructions provide information for identifying or distinguishing each metallothionein protein or peptide isomer from another peptide isomer or all other peptide isomers in a test sample.
65. The kit of any of statements 54-64, wherein the instructions provide information for diagnosing disease.
66. The kit of any of statements 54-65, wherein the instructions provide information for identifying and/or diagnosing cancer or heavy metal toxicity when one or more metallothionein protein isomers is detected in a test sample, or when a specified amount or concentration of one or more protein metallothionein protein isomers is detected in a test sample.
67. The kit of any of statements 54-66, wherein the kit serves as a companion diagnostic for detection or monitoring of diseases such as cancer, toxic exposure, heavy metal poisoning, or the development of metal toxicity induced by platinum-based chemotherapies.
68. The kit of any of statements 54-67, wherein each component is a separate vial or container.

What is claimed is:

1. A method comprising:

isolating total protein from a biological test sample;

reducing proteins in the isolated total protein;

alkylating proteins in the isolated total protein with an alkylating agent to generate alkylated proteins;

cleaving the alkylated proteins to generate alkylated peptides;

mixing the alkylated peptides with a known amount of labeled standard metallothionein peptide to generate a peptide mixture;

separating labeled standard metallothionein peptide and metallothionein isomer peptides from the peptide mixture by methods comprising weak retention on strong cation exchange (SCX) chromatography to generate a metallothionein peptide-containing fraction;

reducing methionine sulfoxides in the metallothionein peptide-containing fraction to generate reduced peptides;

separating the reduced peptides from impurities by reversed phase high pressure liquid chromatography (HPLC); and quantifying an amount of a metallothionein isomer peptide in the test sample by determining the quantity of metallothionein isomer peptide(s) in the sample relative to the known amount of labeled standard metallothionein peptide using mass spectroscopy, wherein the metallothionein isomer peptide is an N-terminal peptide from cleavage of a metallothionein protein isomer selected from the group consisting of metallothionein-1A, metallothionein-1B, metallothionein-1E, metallothionein-1F, metallothionein-1G1, metallothionein-1G2, metallothionein-1H, metallothionein-1L, metallothionein-1M, metallothionein-1X, metallothionein-2, metallothionein-3, and metallothionein-4.

2. The method of claim 1, wherein the test sample is a tissue sample, cell sample, biological fluid sample, tissue biopsy, cultured cell sample, fixed tissue sample, fixed cell sample, or a combination thereof.

3. The method of claim 1, wherein proteins in the test sample are denatured before reducing proteins in the total protein.

4. The method of claim 1, wherein the labeled standard peptide has a shift in mass of the metallothionein isomer peptide by 1 to 10 daltons per cysteine.

5. The method of claim 1, wherein the labeled alkylating agent comprises a stable isotope selected from the group consisting of $^{13}C$, $^{15}N$, and deuterium.

6. The method of claim 1, wherein the metallothionein isomer peptide has a sequence selected from any of SEQ ID NO:18-29.

7. The method of claim 1, wherein quantifying the amount of a metallothionein isomer peptide in a test sample comprises comparing the metallothionein isomer peptide mass spectrum peak height or size with the labeled standard peptide peak height or size.

8. The method of claim 1, further comprising subjecting a control sample to each step performed on the test sample.

9. The method of claim 1, wherein the amount of more than one metallothionein isomer peptide is quantified.

10. A method comprising:
  a. alkylating peptide cysteine residues in a test mixture of peptides with an alkylating agent, after reduction of the peptides' disulfide bonds and/or the peptides' oxidized sulfhydryls, to generate alkylated metallothionein isomeric peptides in a mixture of alkylated peptides;
  b. enriching the alkylated metallothionein isomeric peptides in the alkylated mixture of peptides by removal of undesired peptides to generate an enriched pool of alkylated metallothionein isomeric peptides;
  c. quantifying one or more alkylated metallothionein isomeric peptides in the enriched pool of metallothionein isomer peptides by mass spectrometric determination;

wherein the one or more alkylated metallothionein isomeric peptides is selected from any of SEQ ID NO:18-29.

11. A method comprising:
  a. mass spectroscopy quantification of one or more metallothionein isomeric peptides in a test sample obtained from a subject, to determine a quantified amount of at least one metallothionein protein isomer in the test sample;
  b. comparing the quantified amount of at least one metallothionein protein isomer to a healthy control amount of that type of metallothionein protein isomer to determine whether the subject has a cancer disease;

wherein each of the one or more metallothionein isomeric peptides is selected from any of SEQ ID NO:18-29.

12. The method of claim 1, further comprising treating a disease when the detected quantified amount of metallothionein protein isomer is significantly different from a healthy control amount of that type of metallothionein protein isomer.

13. The method of claim 12, wherein the disease is cancer or heavy metal poisoning.

14. The method of claim 1, further comprising treating a disease selected from the group consisting of breast cancer, colon cancer, lung cancer, prostate cancer, ovarian cancer, bladder cancer, ductal carcinoma, nasopharyngeal carcinoma, colorectal cancer, thyroid carcinoma, hepatocellular carcinoma, leukemia, lymphoma, melanoma, fibrosarcoma, neuroblastoma, autoimmune deficiency syndrome-associated Kaposi's sarcoma, adrenal cortex cancer, pheochromocytoma, cervical cancer, endometrial cancer, esophageal cancer, liver cancer, pancreatic cancer, prostate cancer, thymus cancer, chronic lymphocytic leukemia, Ewing's sarcoma, gestational trophoblastic tumor, hepatoblastoma, multiple myeloma, non-small cell lung cancer, retinoblastoma, bone cancer, or a combination thereof.

15. The method of claim 1, which can identify and quantify as little as 0.05 ng to 2 ng metallothionein protein isomer per µg total protein in the test sample.

* * * * *

UNITED STATES PATENT AND TRADEMARK OFFICE
CERTIFICATE OF CORRECTION

PATENT NO. : 9,470,693 B2  
APPLICATION NO. : 14/401770  
DATED : October 18, 2016  
INVENTOR(S) : Shabb et al.

Page 1 of 1

It is certified that error appears in the above-identified patent and that said Letters Patent is hereby corrected as shown below:

In the Specification

In Column 1, Lines 18-22, delete "This invention was made with government support by the National Institutes of Health, grant no, P20RR016471 and by the National Institute of General Medical Sciences, grant no. P20 GM103442. The government has certain rights in the invention." and insert --This invention was made with government support under grant numbers P20RR016471 and P20GM103442 awarded by the National Institutes of Health. The government has certain rights in the invention.-- therefor Signed and Sealed this  
Third Day of August, 2021

Drew Hirshfeld  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 42

<210> SEQ ID NO 1
<211> LENGTH: 61
<212> TYPE: PRT
<213> ORGANISM: Homo sapiens

<400> SEQUENCE: 1

Met Asp Pro Asn Cys Ser Cys Ala Thr Gly Gly Ser Cys Thr Cys Thr
 1               5                  10                  15

Gly Ser Cys Lys Cys Lys Glu Cys Lys Cys Thr Ser Cys Lys Lys Ser
             20                  25                  30

Cys Cys Ser Cys Cys Pro Met Ser Cys Ala Lys Cys Ala Gln Gly Cys
         35                  40                  45

Ile Cys Lys Gly Ala Ser Glu Lys Cys Ser Cys Cys Ala
     50                  55                  60

<210> SEQ ID NO 2
<211> LENGTH: 61
<212> TYPE: PRT
<213> ORGANISM: Homo sapiens

<400> SEQUENCE: 2

Met Asp Pro Asn Cys Ser Cys Thr Thr Gly Gly Ser Cys Ala Cys Ala
 1               5                  10                  15

Gly Ser Cys Lys Cys Lys Glu Cys Lys Cys Thr Ser Cys Lys Lys Cys
             20                  25                  30

Cys Cys Ser Cys Cys Pro Val Gly Cys Ala Lys Cys Ala Gln Gly Cys
         35                  40                  45

Val Cys Lys Gly Ser Ser Glu Lys Cys Arg Cys Cys Ala
     50                  55                  60

<210> SEQ ID NO 3
<211> LENGTH: 61
<212> TYPE: PRT
<213> ORGANISM: Homo sapiens
```

```
<400> SEQUENCE: 3

Met Asp Pro Asn Cys Ser Cys Ala Thr Gly Gly Ser Cys Thr Cys Ala
1               5                   10                  15

Gly Ser Cys Lys Cys Lys Glu Cys Lys Cys Thr Ser Cys Lys Lys Ser
                20                  25                  30

Cys Cys Ser Cys Cys Pro Val Gly Cys Ala Lys Cys Ala Gln Gly Cys
            35                  40                  45

Val Cys Lys Gly Ala Ser Glu Lys Cys Ser Cys Cys Ala
50                  55                  60

<210> SEQ ID NO 4
<211> LENGTH: 61
<212> TYPE: PRT
<213> ORGANISM: Homo sapiens

<400> SEQUENCE: 4

Met Asp Pro Asn Cys Ser Cys Ala Ala Gly Val Ser Cys Thr Cys Ala
1               5                   10                  15

Gly Ser Cys Lys Cys Lys Glu Cys Lys Cys Thr Ser Cys Lys Lys Ser
                20                  25                  30

Cys Cys Ser Cys Cys Pro Val Gly Cys Ser Lys Cys Ala Gln Gly Cys
            35                  40                  45

Val Cys Lys Gly Ala Ser Glu Lys Cys Ser Cys Cys Asp
50                  55                  60

<210> SEQ ID NO 5
<211> LENGTH: 62
<212> TYPE: PRT
<213> ORGANISM: Homo sapiens

<400> SEQUENCE: 5

Met Asp Pro Asn Cys Ser Cys Ala Ala Gly Val Ser Cys Thr Cys
1               5                   10              15

Ala Ser Ser Cys Lys Cys Lys Glu Cys Lys Cys Thr Ser Cys Lys Lys
                20                  25                  30

Ser Cys Cys Ser Cys Cys Pro Val Gly Cys Ala Lys Cys Ala Gln Gly
            35                  40                  45

Cys Ile Cys Lys Gly Ala Ser Glu Lys Cys Ser Cys Cys Ala
50                  55                  60

<210> SEQ ID NO 6
<211> LENGTH: 61
<212> TYPE: PRT
<213> ORGANISM: Homo sapiens

<400> SEQUENCE: 6

Met Asp Pro Asn Cys Ser Cys Ala Ala Gly Val Ser Cys Thr Cys Ala
1               5                   10                  15

Ser Ser Cys Lys Cys Lys Glu Cys Lys Cys Thr Ser Cys Lys Lys Ser
                20                  25                  30

Cys Cys Ser Cys Cys Pro Val Gly Cys Ala Lys Cys Ala Gln Gly Cys
            35                  40                  45

Ile Cys Lys Gly Ala Ser Glu Lys Cys Ser Cys Cys Ala
50                  55                  60

<210> SEQ ID NO 7
<211> LENGTH: 61
<212> TYPE: PRT
```

-continued

<213> ORGANISM: Homo sapiens

<400> SEQUENCE: 7

Met Asp Pro Asn Cys Ser Cys Glu Ala Gly Ser Cys Ala Cys Ala
1               5                   10                  15

Gly Ser Cys Lys Cys Lys Lys Cys Lys Cys Thr Ser Cys Lys Lys Ser
            20                  25                  30

Cys Cys Ser Cys Cys Pro Leu Gly Cys Ala Lys Cys Ala Gln Gly Cys
        35                  40                  45

Ile Cys Lys Gly Ala Ser Glu Lys Cys Ser Cys Cys Ala
    50                  55                  60

<210> SEQ ID NO 8
<211> LENGTH: 61
<212> TYPE: PRT
<213> ORGANISM: Homo sapiens

<400> SEQUENCE: 8

Met Asp Pro Asn Cys Ser Cys Ala Thr Gly Gly Ser Cys Ser Cys Ala
1               5                   10                  15

Ser Ser Cys Lys Cys Lys Glu Cys Lys Cys Thr Ser Cys Lys Lys Ser
            20                  25                  30

Cys Cys Ser Cys Cys Pro Met Gly Cys Ala Lys Cys Ala Gln Gly Cys
        35                  40                  45

Val Cys Lys Gly Ala Ser Glu Lys Cys Ser Cys Cys Ala
    50                  55                  60

<210> SEQ ID NO 9
<211> LENGTH: 61
<212> TYPE: PRT
<213> ORGANISM: Homo sapiens

<400> SEQUENCE: 9

Met Asp Pro Asn Cys Ser Cys Thr Thr Gly Val Ser Cys Ala Cys Thr
1               5                   10                  15

Gly Ser Cys Lys Cys Lys Glu Cys Lys Cys Thr Ser Cys Lys Lys Ser
            20                  25                  30

Cys Cys Ser Cys Cys Pro Val Gly Cys Ala Lys Cys Ala His Gly Cys
        35                  40                  45

Val Cys Lys Gly Thr Leu Glu Asn Cys Ser Cys Cys Ala
    50                  55                  60

<210> SEQ ID NO 10
<211> LENGTH: 61
<212> TYPE: PRT
<213> ORGANISM: Homo sapiens

<400> SEQUENCE: 10

Met Asp Pro Asn Cys Ser Cys Ser Pro Val Gly Ser Cys Ala Cys Ala
1               5                   10                  15

Gly Ser Cys Lys Cys Lys Glu Cys Lys Cys Thr Ser Cys Lys Lys Ser
            20                  25                  30

Cys Cys Ser Cys Cys Pro Val Gly Cys Ala Lys Cys Ala Gln Gly Cys
        35                  40                  45

Ile Cys Lys Gly Thr Ser Asp Lys Cys Ser Cys Cys Ala
    50                  55                  60

<210> SEQ ID NO 11
<211> LENGTH: 61

<212> TYPE: PRT
<213> ORGANISM: Homo sapiens

<400> SEQUENCE: 11

Met Asp Pro Asn Cys Ser Cys Ala Ala Gly Asp Ser Cys Thr Cys Ala
1               5                   10                  15

Gly Ser Cys Lys Cys Lys Glu Cys Lys Cys Thr Ser Cys Lys Lys Ser
                20                  25                  30

Cys Cys Ser Cys Cys Pro Val Gly Cys Ala Lys Cys Ala Gln Gly Cys
            35                  40                  45

Ile Cys Lys Gly Ala Ser Asp Lys Cys Ser Cys Cys Ala
        50                  55                  60

<210> SEQ ID NO 12
<211> LENGTH: 68
<212> TYPE: PRT
<213> ORGANISM: Homo sapiens

<400> SEQUENCE: 12

Met Asp Pro Glu Thr Cys Pro Cys Pro Ser Gly Gly Ser Cys Thr Cys
1               5                   10                  15

Ala Asp Ser Cys Lys Cys Glu Gly Cys Lys Cys Thr Ser Cys Lys Lys
                20                  25                  30

Ser Cys Cys Ser Cys Cys Pro Ala Glu Cys Glu Lys Cys Ala Lys Asp
            35                  40                  45

Cys Val Cys Lys Gly Gly Glu Ala Ala Glu Ala Glu Ala Glu Lys Cys
        50                  55                  60

Ser Cys Cys Gln
65

<210> SEQ ID NO 13
<211> LENGTH: 62
<212> TYPE: PRT
<213> ORGANISM: Homo sapiens

<400> SEQUENCE: 13

Met Asp Pro Arg Glu Cys Val Cys Met Ser Gly Gly Ile Cys Met Cys
1               5                   10                  15

Gly Asp Asn Cys Lys Cys Thr Thr Cys Asn Cys Lys Thr Cys Arg Lys
                20                  25                  30

Ser Cys Cys Pro Cys Cys Pro Pro Gly Cys Ala Lys Cys Ala Arg Gly
            35                  40                  45

Cys Ile Cys Lys Gly Gly Ser Asp Lys Cys Ser Cys Cys Pro
        50                  55                  60

<210> SEQ ID NO 14
<211> LENGTH: 14
<212> TYPE: DNA
<213> ORGANISM: Homo sapiens

<400> SEQUENCE: 14
gggcctagca gtcg                                                     14

<210> SEQ ID NO 15
<211> LENGTH: 18
<212> TYPE: DNA
<213> ORGANISM: Homo sapiens

<400> SEQUENCE: 15
tggctcagta tcgtattg                                                 18

<210> SEQ ID NO 16
<211> LENGTH: 20
<212> TYPE: DNA
<213> ORGANISM: Homo sapiens

<400> SEQUENCE: 16
cgccgctaga ggtgaaattc                                              20

<210> SEQ ID NO 17
<211> LENGTH: 19
<212> TYPE: DNA
<213> ORGANISM: Homo sapiens

<400> SEQUENCE: 17
ttggcaaatg ctttcgctc                                               19

<210> SEQ ID NO 18
<211> LENGTH: 20
<212> TYPE: PRT
<213> ORGANISM: Homo sapiens

<400> SEQUENCE: 18

Met Asp Pro Asn Cys Ser Cys Ala Thr Gly Gly Ser Cys Thr Cys Thr
1               5                   10                  15

Gly Ser Cys Lys
            20

<210> SEQ ID NO 19
<211> LENGTH: 20
<212> TYPE: PRT
<213> ORGANISM: Homo sapiens

<400> SEQUENCE: 19

Met Asp Pro Asn Cys Ser Cys Thr Thr Gly Gly Ser Cys Ala Cys Ala
1               5                   10                  15

Gly Ser Cys Lys
            20

<210> SEQ ID NO 20
<211> LENGTH: 20
<212> TYPE: PRT
<213> ORGANISM: Homo sapiens

<400> SEQUENCE: 20

Met Asp Pro Asn Cys Ser Cys Ala Thr Gly Gly Ser Cys Thr Cys Ala
1               5                   10                  15

Gly Ser Cys Lys
            20

<210> SEQ ID NO 21
<211> LENGTH: 20
<212> TYPE: PRT
<213> ORGANISM: Homo sapiens

<400> SEQUENCE: 21

Met Asp Pro Asn Cys Ser Cys Ala Ala Gly Val Ser Cys Thr Cys Ala
1               5                   10                  15

Gly Ser Cys Lys
            20

<210> SEQ ID NO 22

<211> LENGTH: 21
<212> TYPE: PRT
<213> ORGANISM: Homo sapiens

<400> SEQUENCE: 22

Met Asp Pro Asn Cys Ser Cys Ala Ala Ala Gly Val Ser Cys Thr Cys
1               5                   10                  15

Ala Ser Ser Cys Lys
            20

<210> SEQ ID NO 23
<211> LENGTH: 20
<212> TYPE: PRT
<213> ORGANISM: Homo sapiens

<400> SEQUENCE: 23

Met Asp Pro Asn Cys Ser Cys Ala Ala Gly Val Ser Cys Thr Cys Ala
1               5                   10                  15

Ser Ser Cys Lys
        20

<210> SEQ ID NO 24
<211> LENGTH: 20
<212> TYPE: PRT
<213> ORGANISM: Homo sapiens

<400> SEQUENCE: 24

Met Asp Pro Asn Cys Ser Cys Glu Ala Gly Gly Ser Cys Ala Cys Ala
1               5                   10                  15

Gly Ser Cys Lys
        20

<210> SEQ ID NO 25
<211> LENGTH: 20
<212> TYPE: PRT
<213> ORGANISM: Homo sapiens

<400> SEQUENCE: 25

Met Asp Pro Asn Cys Ser Cys Ala Thr Gly Gly Ser Cys Ser Cys Ala
1               5                   10                  15

Ser Ser Cys Lys
        20

<210> SEQ ID NO 26
<211> LENGTH: 20
<212> TYPE: PRT
<213> ORGANISM: Homo sapiens

<400> SEQUENCE: 26

Met Asp Pro Asn Cys Ser Cys Thr Thr Gly Val Ser Cys Ala Cys Thr
1               5                   10                  15

Gly Ser Cys Lys
        20

<210> SEQ ID NO 27
<211> LENGTH: 20
<212> TYPE: PRT
<213> ORGANISM: Homo sapiens

<400> SEQUENCE: 27

Met Asp Pro Asn Cys Ser Cys Ser Pro Val Gly Ser Cys Ala Cys Ala
1               5                   10                  15

```
Gly Ser Cys Lys
        20

<210> SEQ ID NO 28
<211> LENGTH: 20
<212> TYPE: PRT
<213> ORGANISM: Homo sapiens

<400> SEQUENCE: 28

Met Asp Pro Asn Cys Ser Cys Ala Ala Gly Asp Ser Cys Thr Cys Ala
1               5                   10                  15

Gly Ser Cys Lys
        20

<210> SEQ ID NO 29
<211> LENGTH: 21
<212> TYPE: PRT
<213> ORGANISM: Homo sapiens

<400> SEQUENCE: 29

Met Asp Pro Glu Thr Cys Pro Cys Pro Ser Gly Gly Ser Cys Thr Cys
1               5                   10                  15

Ala Asp Ser Cys Lys
        20

<210> SEQ ID NO 30
<211> LENGTH: 61
<212> TYPE: PRT
<213> ORGANISM: Homo sapiens

<400> SEQUENCE: 30

Met Asp Pro Asn Cys Ser Cys Ala Thr Gly Gly Ser Cys Thr Cys Thr
1               5                   10                  15

Gly Ser Cys Lys Cys Lys Glu Cys Lys Cys Thr Ser Cys Lys Lys Ser
                20                  25                  30

Cys Cys Ser Cys Cys Pro Met Ser Cys Ala Lys Cys Ala Gln Gly Cys
                35                  40                  45

Ile Cys Lys Gly Ala Ser Glu Lys Cys Ser Cys Ala
        50                  55                  60

<210> SEQ ID NO 31
<211> LENGTH: 61
<212> TYPE: PRT
<213> ORGANISM: Homo sapiens

<400> SEQUENCE: 31

Met Asp Pro Asn Cys Ser Cys Ala Thr Gly Gly Ser Cys Ser Cys Ala
1               5                   10                  15

Ser Ser Cys Lys Cys Lys Glu Cys Lys Cys Thr Ser Cys Lys Lys Ser
                20                  25                  30

Cys Cys Ser Cys Cys Pro Met Gly Cys Ala Lys Cys Ala Gln Gly Cys
                35                  40                  45

Val Cys Lys Gly Ala Ser Glu Lys Cys Ser Cys Ala
        50                  55                  60

<210> SEQ ID NO 32
<211> LENGTH: 61
<212> TYPE: PRT
<213> ORGANISM: Homo sapiens

<400> SEQUENCE: 32
```

Met Asp Pro Asn Cys Ser Cys Ala Thr Gly Ser Cys Thr Cys Ala
1               5                   10                  15

Gly Ser Cys Lys Cys Lys Glu Cys Lys Cys Thr Ser Cys Lys Lys Ser
            20                  25                  30

Cys Cys Ser Cys Cys Pro Val Gly Cys Ala Lys Cys Ala Gln Gly Cys
        35                  40                  45

Val Cys Lys Gly Ala Ser Glu Lys Cys Ser Cys Ala
50                  55                  60

<210> SEQ ID NO 33
<211> LENGTH: 62
<212> TYPE: PRT
<213> ORGANISM: Homo sapiens

<400> SEQUENCE: 33

Met Asp Pro Asn Cys Ser Cys Ala Ala Ala Gly Val Ser Cys Thr Cys
1               5                   10                  15

Ala Ser Ser Cys Lys Cys Lys Glu Cys Lys Cys Thr Ser Cys Lys Lys
            20                  25                  30

Ser Cys Cys Ser Cys Cys Pro Val Gly Cys Ala Lys Cys Ala Gln Gly
        35                  40                  45

Cys Ile Cys Lys Gly Ala Ser Glu Lys Cys Ser Cys Ala
50                  55                  60

<210> SEQ ID NO 34
<211> LENGTH: 61
<212> TYPE: PRT
<213> ORGANISM: Homo sapiens

<400> SEQUENCE: 34

Met Asp Pro Asn Cys Ser Cys Ala Ala Gly Val Ser Cys Thr Cys Ala
1               5                   10                  15

Ser Ser Cys Lys Cys Lys Glu Cys Lys Cys Thr Ser Cys Lys Lys Ser
            20                  25                  30

Cys Cys Ser Cys Cys Pro Val Gly Cys Ala Lys Cys Ala Gln Gly Cys
        35                  40                  45

Ile Cys Lys Gly Ala Ser Glu Lys Cys Ser Cys Ala
50                  55                  60

<210> SEQ ID NO 35
<211> LENGTH: 61
<212> TYPE: PRT
<213> ORGANISM: Homo sapiens

<400> SEQUENCE: 35

Met Asp Pro Asn Cys Ser Cys Ala Ala Gly Val Ser Cys Thr Cys Ala
1               5                   10                  15

Gly Ser Cys Lys Cys Lys Glu Cys Lys Cys Thr Ser Cys Lys Lys Ser
            20                  25                  30

Cys Cys Ser Cys Cys Pro Val Gly Cys Ser Lys Cys Ala Gln Gly Cys
        35                  40                  45

Val Cys Lys Gly Ala Ser Glu Lys Cys Ser Cys Asp
50                  55                  60

<210> SEQ ID NO 36
<211> LENGTH: 61
<212> TYPE: PRT
<213> ORGANISM: Homo sapiens

<400> SEQUENCE: 36

Met Asp Pro Asn Cys Ser Cys Ala Ala Gly Asp Ser Cys Thr Cys Ala
1               5                   10                  15

Gly Ser Cys Lys Cys Lys Glu Cys Lys Cys Thr Ser Cys Lys Lys Ser
                20                  25                  30

Cys Cys Ser Cys Cys Pro Val Gly Cys Ala Lys Cys Ala Gln Gly Cys
            35                  40                  45

Ile Cys Lys Gly Ala Ser Asp Lys Cys Ser Cys Ala
    50                  55                  60

<210> SEQ ID NO 37
<211> LENGTH: 61
<212> TYPE: PRT
<213> ORGANISM: Homo sapiens

<400> SEQUENCE: 37

Met Asp Pro Asn Cys Ser Cys Glu Ala Gly Gly Ser Cys Ala Cys Ala
1               5                   10                  15

Gly Ser Cys Lys Cys Lys Lys Cys Lys Cys Thr Ser Cys Lys Lys Ser
                20                  25                  30

Cys Cys Ser Cys Cys Pro Leu Gly Cys Ala Lys Cys Ala Gln Gly Cys
            35                  40                  45

Ile Cys Lys Gly Ala Ser Glu Lys Cys Ser Cys Ala
    50                  55                  60

<210> SEQ ID NO 38
<211> LENGTH: 61
<212> TYPE: PRT
<213> ORGANISM: Homo sapiens

<400> SEQUENCE: 38

Met Asp Pro Asn Cys Ser Cys Ser Pro Val Gly Ser Cys Ala Cys Ala
1               5                   10                  15

Gly Ser Cys Lys Cys Lys Glu Cys Lys Cys Thr Ser Cys Lys Lys Ser
                20                  25                  30

Cys Cys Ser Cys Cys Pro Val Gly Cys Ala Lys Cys Ala Gln Gly Cys
            35                  40                  45

Ile Cys Lys Gly Thr Ser Asp Lys Cys Ser Cys Ala
    50                  55                  60

<210> SEQ ID NO 39
<211> LENGTH: 61
<212> TYPE: PRT
<213> ORGANISM: Homo sapiens

<400> SEQUENCE: 39

Met Asp Pro Asn Cys Ser Cys Thr Thr Gly Gly Ser Cys Ala Cys Ala
1               5                   10                  15

Gly Ser Cys Lys Cys Lys Glu Cys Lys Cys Thr Ser Cys Lys Lys Cys
                20                  25                  30

Cys Cys Ser Cys Cys Pro Val Gly Cys Ala Lys Cys Ala Gln Gly Cys
            35                  40                  45

Val Cys Lys Gly Ser Ser Glu Lys Cys Arg Cys Ala
    50                  55                  60

<210> SEQ ID NO 40
<211> LENGTH: 61
<212> TYPE: PRT
<213> ORGANISM: Homo sapiens

```
<400> SEQUENCE: 40

Met Asp Pro Asn Cys Ser Cys Thr Thr Gly Val Ser Cys Ala Cys Thr
1               5                   10                  15

Gly Ser Cys Thr Cys Lys Glu Cys Lys Cys Thr Ser Cys Lys Lys Ser
            20                  25                  30

Cys Cys Ser Cys Cys Pro Val Gly Cys Ala Lys Cys Ala His Gly Cys
        35                  40                  45

Val Cys Lys Gly Thr Leu Glu Asn Cys Ser Cys Ala
    50                  55                  60

<210> SEQ ID NO 41
<211> LENGTH: 68
<212> TYPE: PRT
<213> ORGANISM: Homo sapiens

<400> SEQUENCE: 41

Met Asp Pro Glu Thr Cys Pro Cys Pro Ser Gly Gly Ser Cys Thr Cys
1               5                   10                  15

Ala Asp Ser Cys Lys Cys Glu Gly Cys Lys Cys Thr Ser Cys Lys Lys
            20                  25                  30

Ser Cys Cys Ser Cys Cys Pro Ala Glu Cys Glu Lys Cys Ala Lys Asp
        35                  40                  45

Cys Val Cys Lys Gly Gly Glu Ala Ala Glu Ala Glu Ala Glu Lys Cys
    50                  55                  60

Ser Cys Cys Gln
65

<210> SEQ ID NO 42
<211> LENGTH: 62
<212> TYPE: PRT
<213> ORGANISM: Homo sapiens

<400> SEQUENCE: 42

Met Asp Pro Arg Glu Cys Val Cys Met Ser Gly Gly Ile Cys Met Cys
1               5                   10                  15

Gly Asp Asn Cys Lys Cys Thr Thr Cys Asn Cys Lys Thr Tyr Trp Lys
            20                  25                  30

Ser Cys Cys Pro Cys Cys Pro Pro Gly Cys Ala Lys Cys Ala Arg Gly
        35                  40                  45

Cys Ile Cys Lys Gly Gly Ser Asp Lys Cys Ser Cys Cys Pro
    50                  55                  60
```